United States Patent [19]
Briggs et al.

[11] Patent Number: 5,817,883
[45] Date of Patent: Oct. 6, 1998

[54] PROCESSES FOR PRODUCING HYDROXYALDEHYDES

[75] Inventors: John Robert Briggs, Charleston; Kurt Damar Olson, Cross Lanes; Erik Bruce Tjaden, Charleston; Anil Sakharam Guram, Hurricane; Diane Lee Packett, South Charleston; Thomas Carl Eisenschmid, Cross Lanes; Elaine Susan Brigham, Charleston, all of W. Va.

[73] Assignee: Union Carbide Chemicals & Plastics Technology Corporation, Danbury, Conn.

[21] Appl. No.: 843,340

[22] Filed: Apr. 15, 1997

Related U.S. Application Data

[60] Provisional application No. 60/016,259 Apr. 24, 1996, and provisional application No. 60/016,379 Apr. 24, 1996, and provisional application No. 60/016,174 Apr. 24, 1996, and provisional application No. 60/016,263 Apr. 24, 1996.

[51] Int. Cl.$^6$ .................................................. C07C 45/50
[52] U.S. Cl. ........................................... 568/454; 568/451
[58] Field of Search ...................................... 568/451, 454

[56] References Cited

U.S. PATENT DOCUMENTS

| | | | |
|---|---|---|---|
| 3,239,566 | 3/1966 | Slaugh et al. | 260/604 |
| 3,660,493 | 5/1972 | Johnson et al. | 260/604 |
| 3,947,503 | 3/1976 | Kummer | 260/635 |
| 4,185,038 | 1/1980 | Carlock | 260/604 |
| 4,189,448 | 2/1980 | Carlock | 260/604 |
| 4,198,352 | 4/1980 | Kim et al. | 260/604 |
| 4,200,591 | 4/1980 | Hignett et al. | 260/604 |
| 4,200,592 | 4/1980 | Hignett et al. | 260/604 |
| 4,214,109 | 7/1980 | Carlock | 568/909 |
| 4,224,255 | 9/1980 | Smith | 568/451 |
| 4,263,449 | 4/1981 | Saito et al. | 560/263 |
| 4,376,212 | 3/1983 | Ohyama et al. | 560/205 |
| 4,409,418 | 10/1983 | Johnson et al. | 585/667 |
| 4,443,638 | 4/1984 | Yates | 568/882 |
| 4,447,661 | 5/1984 | Hoshiyama et al. | 586/882 |
| 4,451,679 | 5/1984 | Knifton et al. | 568/909 |
| 4,482,749 | 11/1984 | Dennis et al. | 568/454 |
| 4,528,404 | 7/1985 | Oswald et al. | 568/454 |
| 4,567,306 | 1/1986 | Dennis et al. | 568/455 |
| 4,625,068 | 11/1986 | Young | 568/454 |
| 4,647,707 | 3/1987 | van Vliet | 568/882 |
| 4,658,068 | 4/1987 | Henin | 568/451 |
| 4,769,498 | 9/1988 | Billig et al. | 568/454 |
| 5,177,228 | 1/1993 | Sato et al. | 554/129 |
| 5,306,848 | 4/1994 | Vargas | 568/883 |
| 5,312,996 | 5/1994 | Packett | 568/454 |
| 5,434,312 | 7/1995 | Fell et al. | 568/454 |
| 5,504,261 | 4/1996 | Mullin et al. | 568/862 |
| 5,583,250 | 12/1996 | Bahrmann et al. | 560/76 |

FOREIGN PATENT DOCUMENTS

| | | |
|---|---|---|
| 0183545 | 6/1986 | European Pat. Off. . |
| 0343819 | 11/1989 | European Pat. Off. . |
| 0420510 | 3/1991 | European Pat. Off. . |
| 0448848 | 10/1991 | European Pat. Off. . |
| 1254222 | 11/1971 | United Kingdom . |
| 1357735 | 6/1974 | United Kingdom . |

OTHER PUBLICATIONS

J.M. Anderson, et al. *Improved regioselectivity in the hydroformylation reaction catalysed by zeolite–encapsulated rhodium(I) species,* Chem. Commun. 1996, pp. 1543–1544.
J.K. MacDougall, et al. *Metal Hydroxycarbene–Like Intermediates in the Hydrocarbonylation of Alekenes to Alcohols Catalysed by Rhodium Compleses,* Polyhedron, vol. 12, No. 23, pp. 2877–2881 (1993).
Chemical Abstract 1972, 77, 125982t.
Chemical Abstract 1969, 71, 1, 812, 504.

*Primary Examiner*—Gary Geist
*Assistant Examiner*—Sreeni Padmanabhan
*Attorney, Agent, or Firm*—Gerald L. Coon

[57] ABSTRACT

This invention relates in part to processes for producing one or more substituted or unsubstituted hydroxyaldehydes, e.g., 6-hydroxyhexanals, which comprise subjecting one or more substituted or unsubstituted alkadienes, e.g., butadiene, to hydrocarbonylation in the presence of a hydrocarbonylation catalyst, e.g., a metal-organophosphorus ligand complex catalyst, and hydroformylation in the presence of a hydroformylation catalyst, e.g., a metal-organophosphorus ligand complex catalyst, to produce one or more substituted or unsubstituted hydroxyaldehydes. The substituted and unsubstituted hydroxyaldehydes produced by the processes of this invention can undergo further reaction(s) to afford desired derivatives thereof, e.g., epsilon caprolactone. This invention also relates in part to reaction mixtures containing one or more substituted or unsubstituted hydroxyaldehydes as principal product(s) of reaction.

27 Claims, No Drawings

3,817,883

PROCESSES FOR PRODUCING HYDROXYALDEHYDES

This application claims the benefit of provisional U.S. patent application Ser. Nos. 60/016259, 60/016378, 60/016174 and 60/016263, all filed Apr. 24, 1996, and all of the disclosures of which are incorporated herein by reference.

BRIEF SUMMARY OF THE INVENTION

1. Technical Field

This invention relates in part to processes for selectively producing one or more substituted or unsubstituted hydroxyaldehydes, e.g., 6-hydroxyhexanals. This invention also relates in part to reaction mixtures containing one or more substituted or unsubstituted hydroxyaldehydes, e.g., 6-hydroxyhexanals, as the principal product(s) of reaction.

2. Background of the Invention

Hydroxyaldehydes, e.g., 6-hydroxyhexanals, are valuable intermediates which are useful, for example, in the production of epsilon caprolactone, epsilon caprolactam, adipic acid and 1, 6-hexanediol. The processes currently used to produce hydroxyaldehydes have various disadvantages. For example, the starting materials used to produce 6-hydroxyhexanals are relatively expensive. In addition, the selectivity to 6-hydroxyhexanals in prior art processes has been low. Accordingly, it would be desirable to selectively produce hydroxyaldehydes from a relatively inexpensive starting material and by a process which can be employed commercially.

DISCLOSURE OF THE INVENTION

It has been discovered that alkadienes or pentenals can be converted to linear hydroxyaldehydes in high selectivities. It has also been discovered that unsaturated alcohols, e.g., alcohols possessing internal olefinic unsaturation, can be hydroformylated to hydroxyaldehydes, e.g., terminal aldehydes, in high normal:branched isomer ratios, e.g., 3-penten-1-ols hydroformylated to 6-hydroxyhexanals in high normal:branched isomer ratios. In particular, it has been surprisingly discovered that butadiene can be converted to linear 6-hydroxyhexanals, e.g., 6-hydroxyhexanal, by employing catalysts having hydrocarbonylation/hydroformylation/isomerization capabilities. It has further been discovered that high selectivities and high normal:branched isomer ratios may result from conducting the hydrocarbonylation in the presence of a metal-ligand complex catalyst and optionally free ligand in which the ligand is preferably of high basicity and low steric bulk and in the presence of a promoter, i.e., an organic or inorganic compound with an ionizable hydrogen of pKa of from about 1 to about 35.

This invention relates to processes for producing one or more substituted or unsubstituted hydroxyaldehydes, e.g., 6-hydroxyhexanals, which comprise subjecting one or more substituted or unsubstituted alkadienes, e.g., butadiene, to hydrocarbonylation in the presence of a hydrocarbonylation catalyst, e.g., a metal-organophosphorus ligand complex catalyst, and hydroformylation in the presence of a hydroformylation catalyst, e.g., a metal-organophosphorus ligand complex catalyst, to produce one or more substituted or unsubstituted hydroxyaldehydes.

This invention also relates to processes for producing one or more substituted or unsubstituted hydroxyaldehydes, e.g., 6-hydroxyhexanals, which comprise subjecting one or more substituted or unsubstituted pentenals to hydrocarbonylation in the presence of a hydrocarbonylation catalyst, e.g., a metal-organophosphorus ligand complex catalyst, to produce one or more substituted or unsubstituted hydroxyaldehydes.

This invention further relates to processes for producing one or more substituted or unsubstituted hydroxyaldehydes, e.g., 6-hydroxyhexanals, which comprise subjecting one or more substituted or unsubstituted unsaturated alcohols, preferably having at least 4 carbon atoms, e.g., penten-1-ols, to hydroformylation in the presence of a hydroformylation catalyst, e.g., a metal-organophosphorus ligand complex catalyst, to produce said one or more substituted or unsubstituted hydroxyaldehydes.

This invention yet further relates to processes for producing one or more substituted or unsubstituted hydroxyaldehydes, e.g., 6-hydroxyhexanals, which comprise: (a) subjecting one or more substituted or unsubstituted alkadienes, e.g., butadiene, to hydrocarbonylation in the presence of a hydrocarbonylation catalyst, e.g., a metal-organophosphorus ligand complex catalyst, to produce one or more substituted or unsubstituted unsaturated alcohols; and (b) subjecting said one or more substituted or unsubstituted unsaturated alcohols to hydroformylation in the presence of a hydroformylation catalyst, e.g., a metal-organophosphorus ligand complex catalyst, to produce said one or more substituted or unsubstituted hydroxyaldehydes. The hydrocarbonylation reaction conditions in step (a) and the hydroformylation reaction conditions in step (b) may be the same or different, and the hydrocarbonylation catalyst in step (a) and the hydroformylation catalyst in step (b) may be the same or different.

This invention also relates to processes for producing one or more substituted or unsubstituted hydroxyaldehydes, e.g., 6-hydroxyhexanals, which comprises reacting one or more substituted or unsubstituted alkadienes, e.g., butadienes, with carbon monoxide and hydrogen in the presence of a metal-ligand complex catalyst, e.g., a metal-organophosphorus ligand complex catalyst, and a promoter and optionally free ligand to produce one or more substituted or unsubstituted unsaturated alcohols, e.g., penten-1-ols, and reacting said one or more substituted or unsubstituted unsaturated alcohols with carbon monoxide and hydrogen in the presence of a metal-ligand complex catalyst, e.g., a metal-organophosphorus ligand complex catalyst, and optionally free ligand to produce said one or more substituted or unsubstituted hydroxyaldehydes. In a preferred embodiment, the metal-ligand complex catalysts are metal-organophosphorus ligand complex catalysts and the promoter is the one or more starting materials, intermediates or products of the process.

This invention further relates to processes for producing one or more substituted or unsubstituted hydroxyaldehydes, e.g., 6-hydroxyhexanals, which comprises reacting one or more substituted or unsubstituted pentenals with carbon monoxide and hydrogen in the presence of a metal-ligand complex catalyst, e.g., a metal-organophosphorus ligand complex catalyst, and a promoter and optionally free ligand to produce one or more substituted or unsubstituted hydroxyaldehydes. In a preferred embodiment, the metal-ligand complex catalyst is a metal-organophosphorus ligand complex catalyst and the promoter is the one or more starting materials, intermediates or products of the process.

This invention yet further relates to processes for producing one or more substituted or unsubstituted hydroxyaldehydes, e.g., 6-hydroxyhexanals, which comprise reacting one or more substituted or unsubstituted unsaturated alcohols, preferably having at least 4 carbon atoms, e.g., penten-1-ols, with carbon monoxide and hydrogen in the presence of a metal-ligand complex catalyst, e.g., a metal-organophosphorus ligand complex catalyst, and optionally free ligand to produce said one or more substituted or unsubstituted hydroxyaldehydes.

This invention also relates to processes for producing one or more substituted or unsubstituted hydroxyaldehydes, e.g., 6-hydroxyhexanals, which comprises: (a) reacting one or more substituted or unsubstituted alkadienes, e.g., butadienes, with carbon monoxide and hydrogen in the presence of a metal-ligand complex catalyst, e.g., a metal-organophosphorus ligand complex catalyst, and a promoter and optionally free ligand to produce one or more substituted or unsubstituted unsaturated alcohols, e.g., penten-1-ols, and (b) reacting said one or more substituted or unsubstituted unsaturated alcohols with carbon monoxide and hydrogen in the presence of a metal-ligand complex catalyst, e.g., a metal-organophosphorus ligand complex catalyst, and optionally free ligand to produce said one or more substituted or unsubstituted hydroxyaldehydes. The hydrocarbonylation reaction conditions in step (a) and the hydroformylation reaction conditions in step (b) may be the same or different, and the hydrocarbonylation catalyst in step (a) and the hydroformylation catalyst in step (b) may be the same or different.

This invention further relates in part to a process for producing a batchwise or continuously generated reaction mixture comprising:

(1) one or more substituted or unsubstituted 6-hydroxyhexanals, e.g., 6-hydroxyhexanal;

(2) optionally one or more substituted or unsubstituted penten-1-ols, e.g., cis-2-penten-1-ol, trans-2-penten-1-ol, cis-3-penten-1-ol, trans-3-penten-1-ol and/or 4-penten-1-ol;

(3) optionally one or more substituted or unsubstituted 5-hydroxypentanals and/or cyclic lactol derivatives thereof, e.g., 2-methyl-5-hydroxypentanal;

(4) optionally one or more substituted or unsubstituted 4-hydroxybutanals and/or cyclic lactol derivatives thereof, e.g., 2-ethyl-4-hydroxybutanal;

(5) optionally one or more substituted or unsubstituted pentan-1-ols;

(6) optionally one or more substituted or unsubstituted valeraldehydes;

(7) optionally one or more substituted or unsubstituted pentenals, e.g., cis-2-pentenal, trans-2-pentenal, cis-3-pentenal, trans-3-pentenal and/or 4-pentenal;

(8) optionally one or more substituted or unsubstituted 1,6-hexanedials, e.g., adipaldehyde;

(9) optionally one or more substituted 1, 5-pentanedials, e.g., 2-methylglutaraldehyde;

(10) optionally one or more substituted 1,4-butanedials, e.g., 2,3-dimethylsuccinaldehyde and 2-ethylsuccinaldehyde; and

(11) one or more substituted or unsubstituted butadienes, e.g., butadiene;

wherein the weight ratio of component (1) to the sum of components (2), (3), (4), (5), (6), (7), (8), (9) and (10) is greater than about 0.1, preferably greater than about 0.25, more preferably greater than about 1.0; and the weight ratio of component (11) to the sum of components (1), (2), (3), (4), (5), (6), (7), (8), (9) and (10) is about 0 to about 100, preferably about 0.001 to about 50;

which process comprises reacting one or more substituted or unsubstituted butadienes, e.g., butadiene, with carbon monoxide and hydrogen in the presence of a metal-ligand complex catalyst, e.g., a metal-organophosphorus ligand complex catalyst, and a promoter and optionally free ligand to produce one or more substituted or unsubstituted penten-1-ols and reacting said one or more substituted or unsubstituted penten-1-ols with carbon monoxide and hydrogen in the presence of a metal-ligand complex catalyst, e.g., a metal-organophosphorus ligand complex catalyst, and optionally free ligand to produce said batchwise or continuously generated reaction mixture. In a preferred embodiment, the metal-ligand complex catalysts are metal-organophosphorus ligand complex catalysts and the promoter is the one or more starting materials, intermediates or products of the process.

This invention yet further relates in part to a process for producing a batchwise or continuously generated reaction mixture comprising:

(1) one or more substituted or unsubstituted 6-hydroxyhexanals, e.g., 6-hydroxyhexanal;

(2) optionally one or more substituted or unsubstituted penten-1-ols, e.g., cis-2-penten-1-ol, trans-2-penten-1-ol, cis-3-penten-1-ol, trans-3-penten-1-ol and/or 4-penten-1-ol;

(3) optionally one or more substituted or unsubstituted 5-hydroxypentanals and/or cyclic lactol derivatives thereof, e.g., 2-methyl-5-hydroxypentanal;

(4) optionally one or more substituted or unsubstituted 4-hydroxybutanals and/or cyclic lactol derivatives thereof, e.g., 2-ethyl-4-hydroxybutanal;

(5) optionally one or more substituted or unsubstituted pentan-1-ols;

(6) optionally one or more substituted or unsubstituted valeraldehydes; and (7) one or more substituted or unsubstituted pentenals, e.g., cis-2-pentenal, trans-2-pentenal, cis-3-pentenal, trans-3-pentenal and/or 4-pentenal;

wherein the weight ratio of component (1) to the sum of components (2), (3), (4), (5) and (6) is greater than about 0.1, preferably greater than about 0.25, more preferably greater than about 1.0; and the weight ratio of component (7) to the sum of components (1), (2), (3), (4), (5) and (6) is about 0 to about 100, preferably about 0.001 to about 50; which process comprises reacting one or more substituted or unsubstituted pentenals with carbon monoxide and hydrogen in the presence of a metal-ligand complex catalyst, e.g., a metal-organophosphorus ligand complex catalyst, and a promoter and optionally free ligand to produce said batchwise or continuously generated reaction mixture. In a preferred embodiment, the metal-ligand complex catalyst is a metal-organophosphorus ligand complex catalyst and the promoter is the one or more starting materials, intermediates or products of the process.

This invention also relates in part to a process for producing a batchwise or continuously generated reaction mixture comprising:

(1) one or more substituted or unsubstituted 6-hydroxyhexanals, e.g., 6-hydroxyhexanal;

(2) one or more substituted or unsubstituted penten-1-ols, e.g., cis-2-penten-1-ol, trans-2-penten-1-ol, cis-3-penten-1-ol, trans-3-penten-1-ol and/or 4-penten-1-ol;

(3) optionally one or more substituted or unsubstituted 5-hydroxypentanals and/or cyclic lactol derivatives thereof, e.g., 2-methyl-5-hydroxypentanal;

(4) optionally one or more substituted or unsubstituted 4-hydroxybutanals and/or cyclic lactol derivatives thereof, e.g., 2-ethyl-4-hydroxybutanal; and (5) optionally one or more substituted or unsubstituted valeraldehydes;

wherein the weight ratio of component (1) to the sum of components (3), (4) and (5) is greater than about 0.1, preferably greater than about 0.25, more preferably greater than about 1.0; and the weight ratio of component (2) to the sum of components (1), (3), (4) and (5) is about 0 to about 100, preferably about 0.001 to about 50;

which process comprises reacting one or more substituted or unsubstituted penten-1-ols with carbon monoxide and hydrogen in the presence of a metal-ligand complex catalyst, e.g., a metal-organophosphorus ligand complex catalyst, and optionally free ligand to produce said batchwise or continuously generated reaction mixture.

This invention further relates in part to a process for producing a batchwise or continuously generated reaction mixture comprising:

(1) one or more substituted or unsubstituted 6-hydroxyhexanals, e.g., 6-hydroxyhexanal;

(2) optionally one or more substituted or unsubstituted penten-1-ols, e.g., cis-2-penten-1-ol, trans-2-penten-1-ol, cis-3-penten-1-ol, trans-3-penten-1-ol and/or 4-penten-1-ol;

(3) optionally one or more substituted or unsubstituted 5-hydroxypentanals and/or cyclic lactol derivatives thereof, e.g., 2-methyl-5-hydroxypentanal;

(4) optionally one or more substituted or unsubstituted 4-hydroxybutanals and/or cyclic lactol derivatives thereof, e.g., 2-ethyl-4-hydroxybutanal;

(5) optionally one or more substituted or unsubstituted pentan-1-ols;

(6) optionally one or more substituted or unsubstituted valeraldehydes;

(7) optionally one or more substituted or unsubstituted pentenals, e.g., cis-2-pentenal, trans-2-pentenal, cis-3-pentenal, trans-3-pentenal and/or 4-pentenal;

(8) optionally one or more substituted or unsubstituted 1,6-hexanedials, e.g., adipaldehyde;

(9) optionally one or more substituted 1,5-pentanedials, e.g., 2-methylglutaraldehyde;

(10) optionally one or more substituted 1,4-butanedials, e.g., 2,3-dimethylsuccinaldehyde and 2-ethylsuccinaldehyde; and

(11) one or more substituted or unsubstituted butadienes, e.g., butadiene;

wherein the weight ratio of component (1) to the sum of components (2), (3), (4), (5), (6), (7), (8), (9) and (10) is greater than about 0.1, preferably greater than about 0.25, more preferably greater than about 1.0; and the weight ratio of component (11) to the sum of components (1), (2), (3), (4), (5), (6), (7), (8), (9) and (10) is about 0 to about 100, preferably about 0.001 to about 50;

which process comprises: (a) reacting one or more substituted or unsubstituted butadienes, e.g., butadiene, with carbon monoxide and hydrogen in the presence of a metal-ligand complex catalyst, e.g., a metal-organophosphorus ligand complex catalyst, and a promoter and optionally free ligand to produce one or more substituted or unsubstituted penten-1-ols, and (b) reacting said one or more substituted or unsubstituted penten-1-ols with carbon monoxide and hydrogen in the presence of a metal-ligand complex catalyst, e.g., a metal-organophosphorus ligand complex catalyst, and optionally free ligand to produce said batchwise or continuously generated reaction mixture. The hydrocarbonylation reaction conditions in step (a) and the hydroformylation reaction conditions in step (b) may be the same or different, and the hydrocarbonylation catalyst in step (a) and the hydroformylation catalyst in step (b) may be the same or different.

This invention yet further relates to a process for producing a reaction mixture comprising one or more substituted or unsubstituted hydroxyaldehydes, e.g., 6-hydroxyhexanals, which process comprises reacting one or more substituted or unsubstituted alkadienes, e.g., butadienes, with carbon monoxide and hydrogen in the presence of a metal-ligand complex catalyst, e.g., a metal-organophosphorus ligand complex catalyst, and a promoter and optionally free ligand to produce one or more substituted or unsubstituted unsaturated alcohols, e.g., penten-1-ols, and reacting said one or more substituted or unsubstituted unsaturated alcohols with carbon monoxide and hydrogen in the presence of a metal-ligand complex catalyst, e.g., a metal-organophosphorus ligand complex catalyst, and optionally free ligand to produce said reaction mixture comprising one or more substituted or unsubstituted hydroxyaldehydes. In a preferred embodiment, the metal-ligand complex catalysts are metal-organophosphorus ligand complex catalysts and the promoter is the one or more starting materials, intermediates or products of the process.

This invention also relates to a process for producing a reaction mixture comprising one or more substituted or unsubstituted hydroxyaldehydes, e.g., 6-hydroxyhexanals, which process comprises reacting one or more substituted or unsubstituted pentenals with carbon monoxide and hydrogen in the presence of a metal-ligand complex catalyst, e.g., a metal-organophosphorus ligand complex catalyst, and a promoter and optionally free ligand to produce said reaction mixture comprising one or more substituted or unsubstituted hydroxyaldehydes. In a preferred embodiment, the metal-ligand complex catalyst is a metal-organophosphorus ligand complex catalyst and the promoter is the one or more starting materials, intermediates or products of the process.

This invention further relates to a process for producing a reaction mixture comprising one or more substituted or unsubstituted hydroxyaldehydes, e.g., 6-hydroxyhexanals, which process comprises reacting one or more substituted or unsubstituted unsaturated alcohols, preferably having at least 4 carbon atoms, e.g., penten-1-ols, with carbon monoxide and hydrogen in the presence of a metal-ligand complex catalyst, e.g., a metal-organophosphorus ligand complex catalyst, and optionally free ligand to produce said reaction mixture comprising one or more substituted or unsubstituted hydroxyaldehydes.

This invention yet further relates to a process for producing a reaction mixture comprising one or more substituted or unsubstituted hydroxyaldehydes, e.g., 6-hydroxyhexanals, which process comprises: (a) reacting one or more substituted or unsubstituted alkadienes, e.g., butadienes, with carbon monoxide and hydrogen in the presence of a metal-ligand complex catalyst, e.g., a metal-organophosphorus ligand complex catalyst, and a promoter and optionally free ligand to produce one or more substituted or unsubstituted unsaturated alcohols, e.g., penten-1-ols, and (b) reacting said one or more substituted or unsubstituted unsaturated alcohols with carbon monoxide and hydrogen in the presence of a metal-ligand complex catalyst, e.g., a metal-organophosphorus ligand complex catalyst, and optionally free ligand to produce said reaction mixture comprising one or more substituted or unsubstituted hydroxyaldehydes. The hydrocarbonylation reaction conditions in step (a) and the hydroformylation reaction conditions in step (b) may be the same or different, and the hydrocarbonylation catalyst in step (a) and the hydroformylation catalyst in step (b) may be the same or different.

The processes of this invention can achieve high selectivities of alkadienes, pentenals and penten-1-ols to 6-hydroxyhexanals, i.e., selectivities of penten-1-ols to 6-hydroxyhexanals of at least 10% by weight and up to 85% by weight or greater may be achieved by the processes of this invention. Also, the processes of this invention can achieve high normal:branched isomer ratios, e.g., butadiene hydrocarbonylated/hydroformylated to 6-hydroxyhexanals in high normal:branched isomer ratios.

This invention also relates in part to a batchwise or continuously generated reaction mixture comprising:

(1) one or more substituted or unsubstituted 6-hydroxyhexanals, e.g., 6-hydroxyhexanal;

(2) one or more substituted or unsubstituted penten-1-ols, e.g., cis-2-penten-1-ol, trans-2-penten-1-ol, cis-3-penten-1-ol, trans-3-penten-1-ol and/or 4-penten-1-ol;

(3) optionally one or more substituted or unsubstituted 5-hydroxypentanals and/or cyclic lactol derivatives thereof, e.g., 2-methyl-5-hydroxypentanal;

(4) optionally one or more substituted or unsubstituted 4-hydroxybutanals and/or cyclic lactol derivatives thereof, e.g., 2-ethyl-4-hydroxybutanal; and (5) optionally one or more substituted or unsubstituted valeraldehydes;

wherein the weight ratio of component (1) to the sum of components (3), (4) and (5) is greater than about 0.1, preferably greater than about 0.25, more preferably greater than about 1.0; and the weight ratio of component (2) to the sum of components (1), (3), (4) and (5) is about 0 to about 100, preferably about 0.001 to about 50.

This invention further relates in part to a batchwise or continuously generated reaction mixture comprising:

(1) one or more substituted or unsubstituted 6-hydroxyhexanals, e.g., 6-hydroxyhexanal;

(2) optionally one or more substituted or unsubstituted penten-1-ols, e.g., cis-2-penten-1-ol, trans-2-penten-1-ol, cis-3-penten-1-ol, trans-3-penten-1-ol and/or 4-penten-1-ol;

(3) optionally one or more substituted or unsubstituted 5-hydroxypentanals and/or cyclic lactol derivatives thereof, e.g., 2-methyl-5-hydroxypentanal;

(4) optionally one or more substituted or unsubstituted 4-hydroxybutanals and/or cyclic lactol derivatives thereof, e.g., 2-ethyl-4-hydroxybutanal;

(5) optionally one or more substituted or unsubstituted pentan-1-ols;

(6) optionally one or more substituted or unsubstituted valeraldehydes; and (7) optionally one or more substituted or unsubstituted pentenals, e.g., cis-2-pentenal, trans-2-pentenal, cis-3-pentenal, trans-3-pentenal and/or 4-pentenal;

wherein the weight ratio of component (1) to the sum of components (2), (3), (4), (5) and (6) is greater than about 0.1, preferably greater than about 0.25, more preferably greater than about 1.0; and the weight ratio of component (7) to the sum of components (1), (2), (3), (4), (5) and (6) is about 0 to about 100, preferably about 0.001 to about 50.

This invention yet further relates in part to a batchwise or continuously generated reaction mixture comprising:

(1) one or more substituted or unsubstituted 6-hydroxyhexanals, e.g., 6-hydroxyhexanal;

(2) optionally one or more substituted or unsubstituted penten-1-ols, e.g., cis-2-penten-1-ol, trans-2-penten-1-ol, cis-3-penten-1-ol, trans-3-penten-1-ol and/or 4-penten-1-ol;

(3) optionally one or more substituted or unsubstituted 5-hydroxypentanals and/or cyclic lactol derivatives thereof, e.g., 2-methyl-5-hydroxypentanal;

(4) optionally one or more substituted or unsubstituted 4-hydroxybutanals and/or cyclic lactol derivatives thereof, e.g., 2-ethyl-4-hydroxybutanal;

(5) optionally one or more substituted or unsubstituted pentan-1-ols;

(6) optionally one or more substituted or unsubstituted valeraldehydes;

(7) optionally one or more substituted or unsubstituted pentenals, e.g., cis-2-pentenal, trans-2-pentenal, cis-3-pentenal, trans-3-pentenal and/or 4-pentenal;

(8) optionally one or more substituted or unsubstituted 1,6-hexanedials, e.g., adipaldehyde;

(9) optionally one or more substituted 1,5-pentanedials, e.g., 2-methylglutaraldehyde;

(10) optionally one or more substituted 1,4-butanedials, e.g., 2,3-dimethylsuccinaldehyde and 2-ethylsuccinaldehyde; and

(11) one or more substituted or unsubstituted butadienes, e.g., butadiene;

wherein the weight ratio of component (1) to the sum of components (2), (3), (4), (5), (6), (7), (8), (9) and (10) is greater than about 0.1, preferably greater than about 0.25, more preferably greater than about 1.0; and the weight ratio of component (11) to the sum of components (1), (2), (3), (4), (5), (6), (7), (8), (9) and (10) is about 0 to about 100, preferably about 0.001 to about 50.

This invention also relates in part to a reaction mixture comprising one or more substituted or unsubstituted hydroxyaldehydes, e.g., 6-hydroxyhexanals, in which said reaction mixture is prepared by a process which comprises reacting one or more substituted or unsubstituted alkadienes, e.g., butadienes, with carbon monoxide and hydrogen in the presence of a metal-ligand complex catalyst, e.g., a metal-organophosphorus ligand complex catalyst, and a promoter and optionally free ligand to produce one or more substituted or unsubstituted unsaturated alcohols, e.g., penten-1-ols, and reacting said one or more substituted or unsubstituted unsaturated alcohols with carbon monoxide and hydrogen in the presence of a metal-ligand complex catalyst, e.g., a metal-organophosphorus ligand complex catalyst, and optionally free ligand to produce said reaction mixture comprising one or more substituted or unsubstituted hydroxyaldehydes. In a preferred embodiment, the metal-ligand complex catalysts are metal-organophosphorus ligand complex catalysts and the promoter is the one or more starting materials, intermediates or products of the process.

This invention further relates in part to a reaction mixture comprising one or more substituted or unsubstituted hydroxyaldehydes, e.g., 6-hydroxyhexanals, in which said reaction mixture is prepared by a process which comprises reacting one or more substituted or unsubstituted pentenals with carbon monoxide and hydrogen in the presence of a metal-ligand complex catalyst, e.g., a metal-organophosphorus ligand complex catalyst, and a promoter and optionally free ligand to produce said reaction mixture comprising one or more substituted or unsubstituted hydroxyaldehydes. In a preferred embodiment, the metal-ligand complex catalyst is a metal-organophosphorus ligand complex catalyst and the promoter is the one or more starting materials, intermediates or products of the process.

This invention yet further relates in part to a reaction mixture comprising one or more substituted or unsubstituted hydroxyaldehydes, e.g., 6-hydroxyhexanals, in which said reaction mixture is prepared by a process which comprises reacting one or more substituted or unsubstituted unsaturated alcohols, preferably having at least 4 carbon atoms, e.g., penten-1-ols, with carbon monoxide and hydrogen in the presence of a metal-ligand complex catalyst, e.g., a metal-organophosphorus ligand complex catalyst, and optionally free ligand to produce said reaction mixture comprising one or more substituted or unsubstituted hydroxyaldehydes.

This invention also relates in part to a reaction mixture comprising one or more substituted or unsubstituted hydroxyaldehydes, e.g., 6-hydroxyhexanals, in which said reaction mixture is prepared by a process which comprises: (a) reacting one or more substituted or unsubstituted alkadienes, e.g., butadienes, with carbon monoxide and hydrogen in the presence of a metal-ligand complex catalyst, e.g., a metal-organophosphorus ligand complex catalyst, and a promoter and optionally free ligand to produce one or more substituted or unsubstituted unsaturated alcohols, e.g., penten-1-ols, and (b) reacting said one or more substituted or unsubstituted unsaturated alcohols with carbon monoxide and hydrogen in the presence of a metal-ligand complex catalyst, e.g., a metal-organophosphorus ligand complex catalyst, and optionally free ligand to produce said reaction mixture comprising one or more substituted or unsubstituted hydroxyaldehydes. The hydrocarbonylation reaction conditions in step (a) and the hydroformylation reaction conditions in step (b) may be the same or different, and the hydrocarbonylation catalyst in step (a) and the hydroformylation catalyst in step (b) may be the same or different.

The reaction mixtures of this invention are distinctive insofar as the processes for their preparation achieve the generation of high selectivities of 6-hydroxyhexanals in a manner which can be suitably employed in a commercial process for the manufacture of 6-hydroxyhexanals. In particular, the reaction mixtures of this invention are distinctive insofar as the processes for their preparation allow for the production of 6-hydroxyhexanals in relatively high yields without generating large amounts of byproducts, e.g., pentanols and valeraldehyde.

Detailed Description
Hydrocarbonylation Stage or Step

The hydrocarbonylation stage or step of this invention involves converting one or more substituted or unsubstituted alkadienes to one or more substituted or unsubstituted unsaturated alcohols and/or converting one or more substituted or unsubstituted pentenals to one or more substituted or unsubstituted hydroxyaldehydes. The hydrocarbonylation stage or step of this invention may be conducted in one or more steps or stages, preferably a one step process. As used herein, the term "hydrocarbonylation" is contemplated to include all permissible hydrocarbonylation processes which involve converting one or more substituted or unsubstituted alkadienes to one or more substituted or unsubstituted unsaturated alcohols and/or converting one or more substituted or unsubstituted pentenals to one or more substituted or unsubstituted hydroxyaldehydes. In general, the hydrocarbonylation step or stage comprises reacting one or more substituted or unsubstituted alkadienes, e.g., butadienes, with carbon monoxide and hydrogen in the presence of a metal-ligand complex catalyst, e.g., a metal-organophosphorus ligand complex catalyst, and a promoter and optionally free ligand to produce one or more substituted or unsubstituted unsaturated alcohols, e.g., penten-1-ols and/or reacting one or more substituted or unsubstituted pentenals with carbon monoxide and hydrogen in the presence of a metal-ligand complex catalyst, e.g., a metal-organophosphorus ligand complex catalyst, and a promoter and optionally free ligand to produce one or more substituted or unsubstituted hydroxyaldehydes, e.g., 6-hydroxyhexanal. A preferred hydrocarbonylation process useful in this invention is disclosed in U.S. patent application Ser. No. (D-17761), filed on an even date herewith, the disclosure of which is incorporated herein by reference.

The hydrocarbonylation stage or step involves the production of unsaturated alcohols or hydroxyaldehydes by reacting an alkadiene or pentenals with carbon monoxide and hydrogen in the presence of a metal-ligand complex catalyst and optionally free ligand in a liquid medium that also contains a promoter. The reaction may be carried out in a continuous single pass mode in a continuous gas recycle manner or more preferably in a continuous liquid catalyst recycle manner as described below. The hydrocarbonylation processing techniques employable herein may correspond to any known processing techniques.

The hydrocarbonylation process mixtures employable herein includes any solution derived from any corresponding hydrocarbonylation process that may contain at least some amount of four different main ingredients or components, i.e., the unsaturated alcohol or hydroxyaldehyde product, a metal-ligand complex catalyst, a promoter and optionally free ligand, said ingredients corresponding to those employed and/or produced by the hydrocarbonylation process from whence the hydrocarbonylation process mixture starting material may be derived. By "free ligand" is meant organophosphorus ligand that is not complexed with (tied to or bound to) the metal, e.g., rhodium atom, of the complex catalyst. It is to be understood that the hydrocarbonylation process mixture compositions employable herein can and normally will contain minor amounts of additional ingredients such as those which have either been deliberately employed in the hydrocarbonylation process or formed in situ during said process. Examples of such ingredients that can also be present include unreacted alkadiene or pentenal starting materials, carbon monoxide and hydrogen gases, and in situ formed type products, such as saturated alcohols and/or unreacted isomerized olefins corresponding to the alkadiene or pentenal starting materials, and high boiling liquid byproducts, as well as other inert co-solvent type materials or hydrocarbon additives, if employed.

The catalysts useful in the hydrocarbonylation stage or step include metal-ligand complex catalysts. The permissible metals which make up the metal-ligand complexes include Group 8, 9 and 10 metals selected from rhodium (Rh), cobalt (Co), iridium (Ir), ruthenium (Ru), iron (Fe), nickel (Ni), palladium (Pd), platinum (Pt), osmium (Os) and mixtures thereof, with the preferred metals being rhodium, cobalt, iridium and ruthenium, more preferably rhodium, cobalt and ruthenium, especially rhodium. The permissible ligands include, for example, organophosphorus, organoarsenic and organoantimony ligands, or mixtures thereof, preferably organophosphorus ligands. The permissible organophosphorus ligands which make up the metal-organophosphorus ligand complexes and free organophosphorus ligand include mono-, di-, tri- and higher poly-(organophosphorus) compounds, preferably those of high basicity and low steric bulk. Illustrative permissible organophosphorus ligands include, for example, organophosphines, organophosphites, organophosphonites, organophosphinites, organophosphorus nitrogen-containing ligands, organophosphorus sulfur-containing ligands, organophosphorus silicon-containing ligands and the like. Other permissible ligands include, for example, heteroatom-containing ligands such as described in U.S. patent application Ser. No. (D-17646-1), filed Mar. 10, 1997, the disclosure of which is incorporated herein by reference. Mixtures of such ligands may be employed if desired in the metal-ligand complex catalyst and/or free ligand and such mixtures may be the same or different. It is to be noted that the successful practice of this invention does not depend and is not predicated on the exact structure of the metal-ligand complex species, which may be present in their mononuclear, dinuclear and/or higher nuclearity forms. Indeed, the exact structure is not known. Although it is not intended herein to be bound to any theory or mechanistic discourse, it appears that the catalytic species may in its simplest form consist essentially of the metal in complex combination with the ligand and carbon monoxide when used.

The term "complex" as used herein and in the claims means a coordination compound formed by the union of one or more electronically rich molecules or atoms capable of independent existence with one or more electronically poor molecules or atoms, each of which is also capable of independent existence. For example, the ligands employable herein, i.e., organophosphorus ligands, may possess one or more phosphorus donor atoms, each having one available or unshared pair of electrons which are each capable of forming a coordinate covalent bond independently or possibly in concert (e.g., via chelation) with the metal. Carbon monoxide (which is also properly classified as a ligand) can also be present and complexed with the metal. The ultimate composition of the complex catalyst may also contain an additional ligand, e.g., hydrogen or an anion satisfying the coordination sites or nuclear charge of the metal. Illustrative additional ligands include, e.g., halogen (Cl, Br, I), alkyl, aryl, substituted aryl, acyl, $CF_3$, $C_2F_5$, CN, $(R)_2PO$ and $RP(O)(OH)O$ (wherein each R is the same or different and is a substituted or unsubstituted hydrocarbon radical, e.g., the alkyl or aryl), acetate, acetylacetonate, $SO_4$, $BF_4$, $PF_6$, $NO_2$, $NO_3$, $CH_3O$, $CH_2=CHCH_2$, $CH_3CH=CHCH_2$, $C_6H_5CN$, $CH_3CN$, NO, $NH_3$, pyridine, $(C_2H_5)_3N$, mono-olefins, diolefins and triolefins, tetrahydrofuran, and the like. It is of course to be understood that the complex species are preferably free of any additional organic ligand or anion that might poison the catalyst and have an undue adverse effect on catalyst performance. It is preferred in the metal-ligand complex catalyzed hydrocarbonylation process that the active catalysts be free of halogen and sulfur directly bonded to the metal, although such may not be absolutely necessary. Preferred metal-ligand complex catalysts include rhodium-organophosphine ligand complex catalysts.

The number of available coordination sites on such metals is well known in the art. Thus the catalytic species may comprise a complex catalyst mixture, in their monomeric, dimeric or higher nuclearity forms, which are preferably characterized by at least one phosphorus-containing molecule complexed per metal, e.g., rhodium. As noted above, it is considered that the catalytic species of the preferred catalyst employed in the hydrocarbonylation process may be complexed with carbon monoxide and hydrogen in addition to the organophosphorus ligands in view of the carbon monoxide and hydrogen gas employed by the hydrocarbonylation process.

Among the organophosphines that may serve as the ligand of the metal-organophosphine complex catalyst and/or free organophosphine ligand of the hydrocarbonylation process mixture starting materials are mono-, di-, tri- and poly-(organophosphines) such as triorganophosphines, trialkylphosphines, alkyldiarylphosphines, dialkylarylphosphines, dicycloalkylarylphosphines, cycloalkyldiarylphosphines, triaralkylphosphines, tricycloalkylphosphines, and triarylphosphines, alkyl and/or aryl diphosphines and bisphosphine mono oxides, as well as ionic triorganophosphines containing at least one ionic moiety selected from the salts of sulfonic acid, of carboxylic acid, of phosphonic acid and of quaternary ammonium compounds, and the like. Of course any of the hydrocarbon radicals of such tertiary non-ionic and ionic organophosphines may be substituted if desired, with any suitable substitutent that does not unduly adversely affect the desired result of the hydrocarbonylation process. The organophosphine ligands employable in the hydrocarbonylation process and/or methods for their preparation are known in the art.

Illustrative triorganophosphine ligands may be represented by the formula:

wherein each $R^1$ is the same or different and is a substituted or unsubstituted monovalent hydrocarbon radical, e.g., an alkyl, cycloalkyl or aryl radical. In a preferred embodiment, each $R^1$ is the same or different and is selected from primary alkyl, secondary alkyl, tertiary alkyl and aryl. Suitable hydrocarbon radicals may contain from 1 to 24 carbon atoms or greater. Illustrative substituent groups that may be present on the hydrocarbon radicals include, e.g., substituted or unsubstituted alkyl radicals, substituted or unsubstituted alkoxy radicals, substituted or unsubstituted silyl radicals such as $—Si(R^2)_3$; amino radicals such as $—N(R^2)_2$; acyl radicals such as $—C(O)R^2$; carboxy radicals such as $—C(O)OR^2$; acyloxy radicals such as $—OC(O)R^2$; amido radicals such as $—C(O)N(R^2)_2$ and $—N(R^2)C(O)R^2$; ionic radicals such as $—SO_3M$ wherein M represents inorganic or organic cationic atoms or radicals; sulfonyl radicals such as $—SO_2R^2$; ether radicals such as $—OR^2$; sulfinyl radicals such as $—SOR^2$; selenyl radicals such as $—SeR^2$; sulfenyl radicals such as $—SR^2$ as well as halogen, nitro, cyano, trifluoromethyl and hydroxy radicals, and the like, wherein each $R^2$ individually represents the same or different substituted or unsubstituted monovalent hydrocarbon radical, with the proviso that in amino substituents such as $—N(R^2)_2$, each $R^2$ taken together can also represent a divalent bridging group that forms a heterocyclic radical with the nitrogen atom and in amido substituents such as $C(O)N(R^2)_2$ and $—N(R^2)C(O)R^2$ each $—R^2$ bonded to N can also be hydrogen. Illustrative alkyl radicals include, e.g., methyl, ethyl, propyl, butyl, octyl, cyclohexyl, isopropyl and the like. Illustrative aryl radicals include, e.g., phenyl, naphthyl, fluorophenyl, difluorophenyl, benzoyloxyphenyl, carboethoxyphenyl, acetylphenyl, ethoxyphenyl, phenoxyphenyl, hydroxyphenyl; carboxyphenyl, trifluoromethylphenyl, methoxyethylphenyl, acetamidophenyl, dimethylcarbamylphenyl, tolyl, xylyl, 4-dimethylaminophenyl, 2,4,6-trimethoxyphenyl and the like.

Illustrative specific organophosphines include, e.g., trimethylphosphine, triethylphosphine, tributylphosphine, trioctylphosphine, diethylbutylphosphine, diethyl-n-propylphosphine, diethylisopropylphosphine, diethylbenzylphosphine, diethylcyclopentylphosphine, diethylcyclohexylphosphine, triphenylphosphine, tris-p-tolylphosphine, tris-p-methoxyphenylphosphine, tris-dimethylaminophenylphosphine, propyldiphenylphosphine, t-butyldiphenylphosphine, n-butyldiphenylphosphine, n-hexyldiphenylphosphine, cyclohexyldiphenylphosphine, dicyclohexylphenylphosphine, tricyclohexylphosphine, tribenzylphosphine, DIOP, i.e., (4R,5R)-(−)-O-isopropylidene-2,3-dihydroxy- 1,4-bis(diphenylphosphino) butane and/or (4S,5S )-(+)-O-isopropylidene-2,3-dihydroxy-1,4-bis(diphenylphosphino)butane and/or (4S, 5R)-(−)-O-isopropylidene-2,3-dihydroxy-1,4-bis (diphenylphosphino)butane, substituted or unsubstituted bicyclic bisphosphines such as 1,2-bis(1,4-cyclooctylenephosphino)ethane, 1,3-bis(1,4-cyclooctylenephosphino)propane, 1,3-bis(1,5-cyclooctylenephosphino)propane and 1,2-bis(2,6-dimethyl-1,4-cyclooctylenephosphino)ethane, substituted or unsubstituted bis(2,2'-diphenylphosphinomethyl)biphenyl such as bis(2,2'-diphenylphosphinomethyl)biphenyl and bis [2,2'-di(4-fluorophenyl )phosphinomethyl)biphenyl, MeC (CH$_2$PPh$_2$)$_3$ (triphos), NaO$_3$S(C$_6$H$_4$)CH$_2$C(CH$_2$PPh$_2$)$_3$ (sulphos), bis(diphenylphosphino)ferrocene, bis (diisopropylphosphino)ferrocene, bis(diphenylphosphino) ruthenocene, as well as the alkali and alkaline earth metal salts of sulfonated triphenylphosphines, e.g., of (tri-m-sulfophenyl)phosphine and of (m-sulfophenyl)diphenyl-phosphine and the like.

The preferred organophosphorus ligands which make up the metal-organophosphorus ligand complex catalysts and free organophosphorus ligands are high basicity ligands. In general, the basicity of the organophosphorus ligands should be greater than or equal to the basicity of triphenylphosphine (pKb of 2.74), e.g., from about 2.74 to about 15. Suitable organophosphorus ligands have a pKb of about 3 or greater, preferably a pKb of about 3 to about 12, and more preferably a pKb of about 5 to about 12. pKb values for illustrative organophosphorus ligands useful in this invention are given in the Table I below. In addition, the organophosphorus ligands useful in this invention have a steric bulk sufficient to promote the hydrocarbonylation reaction. The steric bulk of monodentate organophosphorus ligands should be lower than or equal to a Tolman cone angle of 210°, preferably lower than or equal to the steric bulk of tricyclohexylphosphine (Tolman cone angle=170°). Organophosphorus ligands having desired basicity and steric bulk include, for example, substituted or unsubstituted tri-primary-alkylphosphines (e.g., trioctylphosphine, diethylbutylphosphine, diethylisobutylphosphine), di-primary-alkylarylphosphines (e.g., diethylphenylphosphine, diethyl-p-N,N-dimethylphenylphosphine), di-primary-alkyl-mono-secondary-alkylphosphines (e.g., diethylisopropylphosphine, diethylcyclohexylphosphine), di-primary-alkyl-tert-alkylphosphines (e.g., diethyl-tert-butylphosphine), mono-primary-alkyl-diarylphosphines (e.g., diphenylmethylphosphine), mono-primary-alkyl-di-secondary-alkylphosphines (e.g., dicyclohexylethylphosphine), triarylphosphines (e.g., tri-para-N,N-dimethylaminophenylphosphine), tri-secondaryalkylphosphines (e.g., tricyclohexylphosphine), mono-primaryalkyl-mono-secondaryalkyl-mono-tertiary alkylphosphines (e.g., ethylisopropyltert-butylphosphine) and the like. The permissible organophosphorus ligands may be substituted with any suitable functionalities and may include the promoter as described hereinbelow.

TABLE I

| Organophosphorus Ligand | pKb |
|---|---|
| Trimethylphosphine | 8.7 |
| Triethylphosphine | 8.7 |
| Tri-n-propylphosphine | 8.7 |
| Tri-n-butylphosphine | 8.4 |
| Tri-n-octylphosphine | 8.4 |
| Tri-tert-butylphosphine | 11.4 |
| Diethyl-tert-butylphosphine | 10.1 |
| Tricyclohexylphosphine | 10 |
| Diphenylmethylphosphine | 4.5 |
| Diethylphenylphosphine | 6.4 |
| Diphenylcyclohexylphosphine | 5 |
| Diphenylethylphosphine | 4.9 |
| Tri(p-methoxyphenyl)phosphine | 4.6 |
| Triphenylphosphine | 2.74 |
| Tri(p-N,N-dimethylaminophenyl)phosphine | 8.65 |
| Tri(p-methylphenyl)phosphine | 3.84 |

More particularly, illustrative metal-organophosphine complex catalysts and illustrative free organophosphine ligands include, for example, those disclosed in U.S. Pat. Nos. 3,239,566, 3,527,809; 4,148,830; 4,247,486; 4,283, 562; 4,400,548; 4,482,749, 4,861,918 and U.S. patent application Ser. No. (D-17459-1), filed on an even date herewith, the disclosures of which are incorporated herein by reference.

Other illustrative permissible organophosphorus ligands which may make up the metal-organophosphorus ligand complexes and free organophosphorus ligands include, for example, those disclosed in U.S. Pat. Nos. 4,567,306, 4,599, 206, 4,668,651, 4,717,775, 3,415,906, 4,567,306, 4,599,206, 4,748,261, 4,769,498, 4,717,775, 4,885,401, 5,202,297, 5,235,113, 5,254,741, 5,264,616, 5,312,996, 5,364,950 and 5,391,801, the disclosures of which are incorporated herein by reference. Still other illustrative permissible organophosphorus ligands which may make up the metal-organophosphorus ligand complexes and free organophosphorus ligands include those described in the hydroformylation section below.

The metal-ligand complex catalysts employable in the hydrocarbonylation step or stage may be formed by methods more fully disclosed in the hydroformylation section hereinbelow. The metal-ligand complex catalysts may be in homogeneous or heterogeneous form as more fully disclosed in the hydroformylation section hereinbelow.

As noted the hydrocarbonylation stage or step involves the use of a metal-ligand complex catalyst as described herein. Of course mixtures of such catalysts can also be employed if desired. The amount of metal-ligand complex catalyst present in the reaction medium of a given hydrocarbonylation process need only be that minimum amount necessary to provide the given metal concentration desired to be employed and which will furnish the basis for at least the catalytic amount of metal necessary to catalyze the particular hydrocarbonylation process involved such as disclosed, for example, in the above-mentioned patents. In general, the catalyst concentration can range from several parts per million to several percent by weight. Organophosphorus ligands can be employed in the above-mentioned catalysts in a molar ratio of generally from about 0.5:1 or less to about 1000:1 or greater. The catalyst concentration will be dependent on the hydrocarbonylation process conditions and solvent employed.

In general, the organophosphorus ligand concentration in hydrocarbonylation process mixtures may range from between about 0.005 and 25 weight percent based on the total weight of the reaction mixture. Preferably the ligand concentration is between 0.01 and 15 weight percent, and more preferably is between about 0.05 and 10 weight percent on that basis.

In general, the concentration of the metal in the hydrocarbonylation process mixtures may be as high as about 2000 parts per million by weight or greater based on the weight of the reaction mixture. Preferably the metal concentration is between about 50 and 1500 parts per million by weight based on the weight of the reaction mixture, and more preferably is between about 70 and 1200 parts per million by weight based on the weight of the reaction mixture.

In addition to the metal-ligand complex catalyst, free ligand (i.e., ligand that is not complexed with the rhodium metal) may also be present in the hydrocarbonylation stage or step medium. The free ligand may correspond to any of the above-defined phosphorus-containing ligands discussed above as employable herein. It is preferred that the free ligand be the same as the ligand of the metal-ligand complex catalyst employed. However, such ligands need not be the same in any given process. The hydrocarbonylation process may involve up to 100 moles, or higher, of free ligand per mole of metal in the hydrocarbonylation process medium. Preferably the hydrocarbonylation stage or step is carried out in the presence of from about 1 to about 50 moles of coordinatable phosphorus, more preferably from about 1 to about 20 moles of coordinatable phosphorus, and most preferably from about 1 to about 8 moles of coordinatable phosphorus, per mole of metal present in the reaction medium; said amounts of coordinatable phosphorus being the sum of both the amount of coordinatable phosphorus that is bound (complexed) to the rhodium metal present and the amount of free (non-complexed) coordinatable phosphorus present. Of course, if desired, make-up or additional coordinatable phosphorus can be supplied to the reaction medium of the hydrocarbonylation process at any time and in any suitable manner, e.g. to maintain a predetermined level of free ligand in the reaction medium.

The substituted and unsubstituted alkadiene starting materials useful in the hydrocarbonylation stage or step include, but are not limited to, conjugated aliphatic diolefins represented by the formula:

(IA)

wherein $R_1$ and $R_2$ are the same or different and are hydrogen, halogen or a substituted or unsubstituted hydrocarbon radical. The alkadienes can be linear or branched and can contain substituents (e.g., alkyl groups, halogen atoms, amino groups or silyl groups). Illustrative of suitable alkadiene starting materials are butadiene, isoprene, dimethyl butadiene, cyclopentadiene and chloroprene. Most preferably, the alkadiene starting material is butadiene itself ($CH_2=CH-CH=CH_2$). For purposes of this invention, the term "alkadiene" is contemplated to include all permissible substituted and unsubstituted conjugated diolefins, including all permissible mixtures comprising one or more substituted and unsubstituted conjugated diolefins. Illustrative of suitable substituted and unsubstituted alkadienes (including derivatives of alkadienes) include those permissible substituted and unsubstituted alkadienes described in Kirk-Othmer, Encyclopedia of Chemical Technology, Fourth Edition, 1996, the pertinent portions of which are incorporated herein by reference.

Illustrative substituted and unsubstituted pentenal starting materials that can be used in the processes of this invention include one or more of the following: cis-2-pentenal, trans-2-pentenal, cis-3-pentenal, trans-3-pentenal, and/or 4-pentenal, including mixtures of one or more of the above pentenals. Illustrative of suitable substituted and unsubstituted pentenals (including derivatives of pentenals) include those permissible substituted and unsubstituted pentenals which are described in Kirk-Othmer, Encyclopedia of Chemical Technology, Fourth Edition, 1996, the pertinent portions of which are incorporated herein by reference.

The particular hydrocarbonylation reaction conditions are not narrowly critical and can be any effective hydrocarbonylation procedures sufficient to produce one or more unsaturated alcohols or hydroxyaldehydes. The exact reaction conditions will be governed by the best compromise between achieving high catalyst selectivity, activity, lifetime and ease of operability, as well as the intrinsic reactivity of the starting materials in question and the stability of the starting materials and the desired reaction product to the reaction conditions. The hydrocarbonylation stage or step conditions may include any suitable type hydrocarbonylation conditions heretofore employed for producing alcohols or hydroxyaldehydes. The total pressure employed in the hydrocarbonylation process may range in general from about 1 to about 10,000 psia, preferably from about 20 to 3000 psia and more preferably from about 50 to about 2000 psia. The total pressure of the hydrocarbonylation process will be dependent on the particular catalyst system employed.

More specifically, the carbon monoxide partial pressure of the hydrocarbonylation process in general may range from about 1 to about 3000 psia, and preferably from about 3 to about 1500 psia, while the hydrogen partial pressure in general may range from about 1 to about 3000 psia, and preferably from about 3 to about 1500 psia. In general, the molar ratio of carbon monoxide to gaseous hydrogen may range from about 100:1 or greater to about 1:100 or less, the preferred carbon monoxide to gaseous hydrogen molar ratio being from about 1:10 to about 10:1. The carbon monoxide and hydrogen partial pressures will be dependent in part on the particular catalyst system employed. It is understood that carbon monoxide and hydrogen can be employed separately, either alone or in mixture with each other, i.e., synthesis gas, or may be produced in situ under reaction conditions and/or be derived from the promoter or solvent (not necessarily involving free hydrogen or carbon monoxide). In an embodiment, the hydrogen partial pressure and carbon monoxide partial pressure are sufficient to prevent or minimize derivatization, e.g., hydrogenation of penten-1-ols or further hydrocarbonylation of penten-1-ols or hydrogenation of alkadienes. The hydrocarbonylation is preferably conducted at a hydrogen partial pressure and carbon monoxide partial pressure sufficient to prevent or minimize formation of substituted or unsubstituted pentan-1-ols, and/or substituted or unsubstituted valeraldehydes.

Further, the hydrocarbonylation process may be conducted at a reaction temperature from about 20° C. to about 200° C., preferably from about 50° C. to about 150° C., and more preferably from about 65° C. to about 115° C. The temperature must be sufficient for reaction to occur (which may vary with catalyst system employed), but not so high that ligand or catalyst decomposition occurs. At high temperatures (which may vary with catalyst system employed), conversion of penten-1-ols to undesired byproducts may occur.

Of course, it is to be also understood that the hydrocarbonylation process conditions employed will be governed by the type of unsaturated alcohol or hydroxyaldehyde product desired.

To enable maximum levels of 3-penten-1-ols and/or 4-penten-1-ols and minimize 2-penten-1-ols, it is desirable to maintain some alkadiene partial pressure or when the alkadiene conversion is complete, the carbon monoxide and hydrogen partial pressures should be sufficient to prevent or minimize derivatization, e.g., hydrogenation of penten-1-ols or further hydrocarbonylation of penten-1-ols or hydrogenation of alkadienes.

In a preferred embodiment, the alkadiene hydrocarbonylation is conducted at an alkadiene partial pressure and/or a carbon monoxide and hydrogen partial pressures sufficient to prevent or minimize derivatization, e.g., hydrogenation of penten-1-ols or further hydrocarbonylation of penten-1-ols or hydrogenation of alkadienes. In a more preferred embodiment, the alkadiene, e.g., butadiene, hydrocarbonylation is conducted at an alkadiene partial pressure of greater than 0 psi, preferably greater than 5 psi, and more preferably greater than 9 psi; at a carbon monoxide partial pressure of greater than 0 psi, preferably greater than 25 psi, and more preferably greater than 40 psi; and at a hydrogen partial pressure of greater than 0 psi, preferably greater than 25 psi, and more preferably greater than 80 psi.

The hydrocarbonylation process is also conducted in the presence of a promoter. As used herein, "promoter" means an organic or inorganic compound with an ionizable hydrogen of pKa of from about 1 to about 35. Illustrative promoters include, for example, protic solvents, organic and inorganic acids, alcohols, water, phenols, thiols, thiophenols, nitroalkanes, ketones, nitriles, amines (e.g., pyrroles and diphenylamine), amides (e.g., acetamide), mono-, di- and trialkylammonium salts, and the like. Approximate pKa values for illustrative promoters useful in this invention are given in the Table II below. The promoter may be present in the hydrocarbonylation reaction mixture either alone or incorporated into the ligand structure, either as the metal-ligand complex catalyst or as free ligand, or into the alkadiene structure. The desired promoter will depend on the nature of the ligands and metal of the metal-ligand complex catalysts. In general, a catalyst with a more basic metal-bound acyl or other intermediate will require a lower concentration and/or a less acidic promoter.

Although it is not intended herein to be bound to any theory or mechanistic discourse, it appears that the promoter may function to transfer a hydrogen ion to or otherwise activate a catalyst-bound acyl or other intermediate. Mixtures of promoters in any permissible combination may be useful in this invention. A preferred class of promoters includes those that undergo hydrogen bonding, e.g., NH, OH and SH-containing groups and Lewis acids, since this is believed to facilitate hydrogen ion transfer to or activation of the metal-bound acyl or other intermediate. In general, the amount of promoter may range from about 10 parts per million or so up to about 99 percent by weight or more based on the total weight of the hydrocarbonylation process mixture starting materials.

TABLE II

| Promoter | pKa |
|---|---|
| ROH (R = alkyl) | 15–19 |
| ROH (R = aryl) | 8–11 |
| RCONHR (R = hydrogen or alkyl, e.g., acetamide) | 15–19 |
| $R_3NH^+$, $R_2NH_2^+$ (R = alkyl) | 10–11 |
| $RCH_2NO_2$ | 8–11 |
| $RCOCH_2R$ (R = alkyl) | 19–20 |
| RSH (R = alkyl) | 10–11 |
| RSH (R = aryl) | 8–11 |
| $CNCH_2CN$ | 11 |

TABLE II-continued

| Promoter | pKa |
|---|---|
| Diarylamine | 21–24 |
| Pyrrole | 20 |
| Pyrrolidine | 34 |

The concentration of the promoter employed will depend upon the details of the catalyst system employed. Without wishing to be bound by theory, the promoter component must be sufficiently acidic and in sufficient concentration to transfer a hydrogen ion to or otherwise activate the catalyst-bound acyl or other intermediate. It is believed that a promoter component acidity or concentration which is insufficient to transfer a hydrogen ion to or otherwise activate the catalyst-bound acyl or other intermediate will result in the formation of pentenal products, rather than the preferred penten-1-ol products. The ability of a promoter component to transfer a hydrogen ion to or otherwise activate the catalyst-bound acyl or other intermediate may be governed by several factors, for example, the concentration of the promoter component, the intrinsic acidity of the promoter component (the pKa), the composition of the reaction medium (e.g., the reaction solvent) and the temperature. Promoters are chosen on the basis of their ability to transfer a hydrogen ion to or otherwise activate such a catalyst-bound acyl or other intermediate under reaction conditions sufficient to result in the formation of alcohol or hydroxyaldehyde products, but not so high as to result in detrimental side reactions of the catalyst, reactants or products. In cases where the promoter component acidity or concentration is insufficient to do so, aldehyde products (e.g., pentenals) are initially formed which may or may not be subsequently converted to unsaturated alcohols, e.g., penten-1-ols, or hydroxyaldehydes, e.g., 6-hydroxyhexanal.

In general, a less basic metal-bound acyl will require a higher concentration of the promoter component or a more acidic promoter component to protonate or otherwise activate it fully, such that the products are more desired penten-1-ols, rather than pentenals. This can be achieved by appropriate choice of promoter component. For example, an enabling concentration of protonated or otherwise activated catalyst-bound acyl or other intermediate can be achieved though the use of a large concentration of a mildly acidic promoter component, or through the use of a smaller concentration of a more acidic component. The promoter component is selected based upon its ability to produce the desired concentration of protonated or otherwise activated catalyst-bound acyl or other intermediate in the reaction medium under reaction conditions. In general, the intrinsic strength of an acidic material is generally defined in aqueous solution as the pKa, and not in reaction media commonly employed in hydrocarbonylation. The choice of the promoter and its concentration is made based in part upon the theoretical or equivalent pH that the promoter alone at such concentration gives in aqueous solution at 22° C. The desired theoretical or equivalent pH of promoter component solutions should be greater than 0, preferably from about 1–12, more preferably from about 2–10 and most preferably from 4–8. The theoretical or equivalent pH can be readily calculated from values of pKa's at the appropriate promoter component concentration by reference to standard tables such as those found in "Ionization Constants of Organic Acids in Aqueous Solution" (IUPAC Chemical Data Series—No. 23) by E. P Serjeant and Boyd Dempsey, Pergamon Press (1979) and "Dissociation Constants of Inorganic Acids and Bases in Aqueous Solution" (IUPAC Chemical Data Series—No. 19, by D. D. Perrin, Pergamon Press.

Depending on the particular catalyst and reactants employed, suitable promoters preferably include solvents, for example, alcohols (e.g., the unsaturated alcohol or hydroxyaldehyde products such as penten-1-ols or 6-hydroxyhexanals), thiols, thiophenols, selenols, tellurols, alkenes, alkynes, aldehydes, higher boiling byproducts, ketones, esters, amides, primary and secondary amines, alkylaromatics and the like. Any suitable promoter which does not unduly adversely interfere with the intended hydrocarbonylation process can be employed. Permissible protic solvents have a pKa of about 1–35, preferably a pKa of about 3–30, and more preferably a pKa of about 5–25. Mixtures of one or more different solvents may be employed if desired.

In general, with regard to the production of unsaturated alcohols or hydroxyaldehydes, it is preferred to employ unsaturated alcohol or hydroxyaldehyde promoters corresponding to the unsaturated alcohol or hydroxyaldehyde products desired to be produced and/or higher boiling byproducts as the main protic solvents. Such byproducts can also be preformed if desired and used accordingly. Illustrative preferred protic solvents employable in the production of unsaturated alcohols, e.g., penten-1-ols, or hydroxyaldehydes, e.g., 6-hydroxyhexanal, include alcohols (e.g., pentenols, octanols, hexanediols), amines, thiols, thiophenols, ketones (e.g. acetone and methylethyl ketone), hydroxyaldehydes (e.g., 6-hydroxyaldehyde), lactols (e.g., 2-methylvalerolactol), esters (e.g. ethyl acetate), hydrocarbons (e.g. diphenylmethane, triphenylmethane), nitrohydrocarbons (e.g. nitromethane), 1,4-butanediols and sulfolane. Suitable protic solvents are disclosed in U.S. Pat. No. 5,312,996.

As indicated above, the promoter may be incorporated into the organophosphorus ligand structure, either as the metal-ligand complex catalyst or as free ligand. Suitable organophosphorus ligand promoters which may be useful in this invention include, for example, tris(2-hydroxyethyl) phosphine, tris(3-hydroxypropyl)phosphine, tris(2-hydroxyphenylphosphine), tris(4-hydroxyphenylphosphine), tris(3-carboxypropyl)phosphine, tris(3-carboxamidopropyl)phosphine, diphenyl(2-hydroxyphenyl)phosphine, diethyl(2-anilinophenyl) phosphine, and tris(3-pyrroyl)phosphine. The use of ligand promoters may by particularly beneficial in those instances when the unsaturated alcohol or hydroxyaldehyde product is not effective as a promoter. As with the organophosphorus ligands which make up the metal-organophosphorus ligand complex catalysts and free organophosphorus ligands, the organophosphorus ligand promoters preferably are high basicity ligands having a steric bulk lower than or equal to a Tolman cone angle of 210°, preferably lower than or equal to the steric bulk of tricyclohexylphosphine (Tolman cone angle=170°). Indeed, the organophosphorus ligand promoters may be employed as organophosphorus ligands which make up the metal-organophosphorus ligand complex catalysts and free organophosphorus ligands. Mixtures of promoters comprising one or more organophosphorus ligand promoters and mixtures comprising one or more organophosphorus ligand promoters and one or more other promoters, e.g., protic solvents, may be useful in this invention.

In an embodiment of the invention, the hydrocarbonylation process mixture may consist of one or more liquid phases, e.g. a polar and a nonpolar phase. Such processes are often advantageous in, for example, separating products from catalyst and/or reactants by partitioning into either phase. In addition, product selectivities dependent upon solvent properties may be increased by carrying out the reaction in that solvent. An application of this technology is the aqueous-phase hydrocarbonylation of alkadienes employing sulfonated phosphine ligands, hydroxylated phosphine ligands and aminated phosphine ligands for the rhodium catalyst. A process carried out in aqueous solvent is particularly advantageous for the preparation of alcohols or hydroxyaldehydes because the products may be separated from the catalyst by extraction into a solvent.

As described herein, the phosphorus-containing ligand for the rhodium hydrocarbonylation catalyst may contain any of a number of substituents, such as cationic or anionic substituents, which will render the catalyst soluble in a polar phase, e.g. water. Optionally, a phase-transfer catalyst may be added to the reaction mixture to facilitate transport of the catalyst, reactants, or products into the desired solvent phase. The structure of the ligand or the phase-transfer catalyst is not critical and will depend on the choice of conditions, reaction solvent, and desired products.

When the catalyst is present in a multiphasic system, the catalyst may be separated from the reactants and/or products by conventional methods such as extraction or decantation. The reaction mixture itself may consist of one or more phases; alternatively, the multiphasic system may be created at the end of the reaction by for example addition of a second solvent to separate the products from the catalyst. See, for example, U.S. Pat. No. 5,180,854, the disclosure of which is incorporated herein by reference.

In an embodiment of this invention, an olefin can be hydrocarbonylated along with an alkadiene or pentenal using the above-described metal-ligand complex catalysts. In such cases, an alcohol derivative of the olefin is also produced along with the unsaturated alcohols, e.g., penten-1-ols, or hydroxyaldehydes, e.g., 6-hydroxyhexanal. Mixtures of such olefinic starting materials are described more fully in the hydroformylation section hereinbelow.

In those instances where the promoter is not the solvent, the hydrocarbonylation process is conducted in the presence of an organic solvent for the metal-ligand complex catalyst and free organophosphorus ligand. The solvent may also contain dissolved water up to the saturation limit. Depending on the particular catalyst and reactants employed, suitable organic solvents include, for example, alcohols, alkanes, alkenes, alkynes, ethers, aldehydes, higher boiling hydrocarbonylation byproducts, ketones, esters, amides, tertiary amines, aromatics and the like. Any suitable solvent which does not unduly adversely interfere with the intended hydrocarbonylation reaction can be employed. Mixtures of one or more different solvents may be employed if desired. Illustrative preferred solvents employable in the production of alcohols or hydroxyaldehydes include ketones (e.g. acetone and methylethyl ketone), esters (e.g. ethyl acetate), hydrocarbons (e.g. toluene), nitrohydrocarbons (e.g. nitrobenzene), ethers (e.g. tetrahydrofuran (THF) and sulfolane. Suitable solvents are disclosed in U.S. Pat. No. 5,312,996. The amount of solvent employed is not critical to the subject invention and need only be that amount sufficient to solubilize the catalyst and free ligand of the hydrocarbonylation reaction mixture to be treated. In general, the amount of solvent may range from about 5 percent by weight up to about 99 percent by weight or more based on the total weight of the hydrocarbonylation reaction mixture starting material.

Illustrative substituted and unsubstituted unsaturated alcohol intermediates/starting materials that can be prepared by and/or used in the processes of this invention include one or more of the following: alkenols such as cis-3-penten-1-ol, trans-3-penten-1-ol, 4-penten-1-ol, cis-2-penten-1-ol and/or trans-2-penten-1-ol, including mixtures comprising one or more of the above unsaturated alcohols. The preferred unsaturated alcohols have at least 4 carbon atoms, preferably 4 to about 30 carbon atoms, and more preferably 4 to about 20 carbon atoms. Illustrative of suitable substituted and unsubstituted unsaturated alcohols (including derivatives of unsaturated alcohols) include those permissible substituted and unsubstituted unsaturated alcohols which are described in Kirk-Othmer, Encyclopedia of Chemical Technology, Fourth Edition, 1996, the pertinent portions of which are incorporated herein by reference.

As indicated above, it is generally preferred to carry out the hydrocarbonylation stage or step in a continuous manner. In general, continuous hydrocarbonylation process may involve: (a) hydrocarbonylating the alkadiene or pentenal starting material(s) with carbon monoxide and hydrogen in a liquid homogeneous reaction mixture comprising a solvent, a metal-ligand complex catalyst, and free ligand; (b) maintaining reaction temperature and pressure conditions favorable to the hydrocarbonylation of the alkadiene or pentenal starting material(s); (c) supplying make-up quantities of the alkadiene or pentenal starting material(s), carbon monoxide and hydrogen to the reaction medium as those reactants are used up; and (d) recovering the desired unsaturated alcohol or hydroxyaldehyde product(s) in any manner desired. The continuous reaction can be carried out in a single pass mode, i.e., wherein a vaporous mixture comprising unreacted alkadiene or pentenal starting material(s) and vaporized alcohol or hydroxyaldehyde product is removed from the liquid reaction mixture from whence the alcohol or hydroxyaldehyde product is recovered and make-up alkadiene or pentenal starting material(s), carbon monoxide and hydrogen are supplied to the liquid reaction medium for the next single pass through without recycling the unreacted alkadiene or pentenal starting material(s). However, it is generally desirable to employ a continuous reaction that involves either a liquid and/or gas recycle procedure. Such types of recycle procedure are known in the art and may involve the liquid recycling of the metal-ligand complex catalyst solution separated from the desired alcohol or hydroxyaldehyde reaction product(s).

As indicated above, the hydrocarbonylation stage or step may involve a liquid catalyst recycle procedure. Such liquid catalyst recycle procedures are known in the art. For instance, in such liquid catalyst recycle procedures it is commonplace to continuously or intermittently remove a portion of the liquid reaction product medium, containing, e.g., the alcohol or hydroxyaldehyde product, the solubilized metal-ligand complex catalyst, free ligand, and organic solvent, as well as byproducts produced in situ by the hydrocarbonylation and unreacted alkadiene or pentenal starting material, carbon monoxide and hydrogen (syn gas) dissolved in said medium, from the hydrocarbonylation reactor, to a distillation zone, e.g., a vaporizer/separator wherein the desired alcohol or hydroxyaldehyde product is distilled in one or more stages under normal, reduced or elevated pressure, as appropriate, and separated from the liquid medium. The vaporized or distilled desired alcohol or hydroxyaldehyde product so separated may then be condensed and recovered in any conventional manner as discussed above. The remaining non-volatilized liquid residue which contains metal-ligand complex catalyst, solvent, free organophosphorus ligand and usually some undistilled alcohol or hydroxyaldehyde product is then recycled back, with or with out further treatment as desired, along with whatever by-product and non-volatilized gaseous reactants that might still also be dissolved in said recycled liquid residue, in any conventional manner desired, to the hydrocarbonylation reactor, such as disclosed e.g., in the above-mentioned patents. Moreover the reactant gases so removed by such distillation from the vaporizer may also be recycled back to the reactor if desired.

Recovery and purification of unsaturated alcohols or hydroxyaldehydes may be by any appropriate means, and may include distillation, phase separation, extraction, precipitation, absorption, crystallization, membrane separation, derivative formation and other suitable means. For example, a crude reaction product can be subjected to a distillation-separation at atmospheric or reduced pressure through a packed distillation column. Reactive distillation may be useful in conducting the hydrocarbonylation reaction. Suitable recovery and purification methods are described more fully in the hydroformylation section hereinbelow. The subsequent hydroformylation of the unsaturated alcohol may be conducted without the need to separate the unsaturated alcohol from the other components of the crude reaction mixtures.

While not wishing to be bound to any particular reaction mechanism, it is believed that the overall hydrocarbonylation reaction generally proceeds in one step, e.g., the one or more substituted or unsubstituted alkadienes (e.g., butadiene) are converted to one or more substituted or unsubstituted unsaturated alcohols (e.g., a 3-pentenol and/or 4-pentenol) either directly or through one or more intermediates (e.g., a 3-pentenal and/or 4-pentenal). This invention is not intended to be limited in any manner by any particular reaction mechanism, but rather encompasses all permissible reaction mechanisms involved in hydrocarbonylating one or more substituted or unsubstituted alkadienes with carbon monoxide and hydrogen in the presence of a metal-ligand complex catalyst and a promoter and optionally free ligand to produce one or more substituted or unsubstituted unsaturated alcohols or hydrocarbonylating one or more substituted or unsubstituted pentenals with carbon monoxide and hydrogen in the presence of a metal-ligand complex catalyst and a promoter and optionally free ligand to produce one or more substituted or unsubstituted hydroxyaldehydes.

Hydroformylation Step or Stage

The hydroformylation step or stage involves the production of hydroxyaldehydes, e.g., 6-hydroxyhexanals, by reacting an olefinic compound, e.g., penten-1-ols, with carbon monoxide and hydrogen in the presence of a metal-ligand complex catalyst and optionally free ligand in a liquid medium that also contains a solvent for the catalyst and ligand or the production of pentenals by reacting an alkadiene compound, e.g., butadiene, with carbon monoxide and hydrogen in the presence of a metal-ligand complex catalyst and optionally free ligand in a liquid medium that also contains a solvent for the catalyst and ligand. The processes may be carried out in a continuous single pass mode in a continuous gas recycle manner or more preferably in a continuous liquid catalyst recycle manner as described below. The hydroformylation processing techniques employable herein may correspond to any known processing techniques such as preferably employed in conventional liquid catalyst recycle hydroformylation reactions. As used herein, the term "hydroformylation" is contemplated to include, but is not limited to, all permissible hydroformylation processes which involve converting one or more substituted or unsubstituted unsaturated alcohols, e.g., alcohols possessing internal olefinic unsaturation, to one or more substituted or unsubstituted hydroxyaldehydes or converting one or more substituted or unsubstituted alkadienes to one or more substituted or unsubstituted pentenals. In general, the hydroformylation step or stage comprises reacting one or more substituted or unsubstituted penten-1-ols with carbon monoxide and hydrogen in the presence of a catalyst to produce one or more substituted or unsubstituted 6-hydroxyhexanals or reacting one or more substituted or unsubstituted alkadienes with carbon monoxide and hydrogen in the presence of a catalyst to produce one or more substituted or unsubstituted pentenals.

The hydroformylation reaction mixtures employable herein include any solution derived from any corresponding hydroformylation process that may contain at least some amount of four different main ingredients or components, i.e., the hydroxyaldehyde or pentenal product, a metal-ligand complex catalyst, optionally free ligand and an organic solubilizing agent for said catalyst and said free ligand, said ingredients corresponding to those employed and/or produced by the hydroformylation process from whence the hydroformylation reaction mixture starting material may be derived. By "free ligand" is meant organophosphorus ligand that is not complexed with (tied to or bound to) the metal, e.g., rhodium atom, of the complex catalyst. It is to be understood that the hydroformylation reaction mixture compositions employable herein can and normally will contain minor amounts of additional ingredients such as those which have either been deliberately employed in the hydroformylation process or formed in situ during said process. Examples of such ingredients that can also be present include unreacted unsaturated alcohol or alkadiene starting material, carbon monoxide and hydrogen gases, and in situ formed type products, such as saturated hydrocarbons and/or unreacted isomerized olefins corresponding to the unsaturated alcohol or alkadiene starting materials, and high boiling liquid aldehyde condensation byproducts, as well as other inert co-solvent type materials or hydrocarbon additives, if employed.

The catalysts useful in the hydroformylation process include metal-ligand complex catalysts. The permissible metals which make up the metal-ligand complexes include Group 8, 9 and 10 metals selected from rhodium (Rh), cobalt (Co), iridium (Ir), ruthenium (Ru), iron (Fe), nickel (Ni), palladium (Pd), platinum (Pt), osmium (Os) and mixtures thereof, with the preferred metals being rhodium, cobalt, iridium and ruthenium, more preferably rhodium, cobalt and ruthenium, especially rhodium. The permissible ligands include, for example, organophosphorus, organoarsenic and organoantimony ligands, or mixtures thereof, preferably organophosphorus ligands. The permissible organophosphorus ligands which make up the metal-ligand complexes include organophosphines, e.g., mono-, di-, tri- and poly-(organophosphines), and organophosphites, e.g., mono-,di-,tri- and poly-(organophosphites). Other permissible organophosphorus ligands include, for example, organophosphonites, organophosphinites, amino phosphines and the like. Still other permissible ligands include, for example, heteroatom-containing ligands such as described in U.S. patent application Ser. No. (D-17646-1), filed Mar. 10, 1997, the disclosure of which is incorporated herein by reference. Mixtures of such ligands may be employed if desired in the metal-ligand complex catalyst and/or free ligand and such mixtures may be the same or different. This invention is not intended to be limited in any manner by the permissible organophosphorus ligands or mixtures thereof. It is to be noted that the successful practice of this invention does not depend and is not predicated on the exact structure of the metal-ligand complex species, which may be present in their mononuclear, dinuclear and/or higher nuclearity forms. Indeed, the exact structure is not known. Although it is not intended herein to be bound to any theory or mechanistic discourse, it appears that the catalytic species may in its simplest form consist essentially of the metal in complex combination with the ligand and carbon monoxide when used.

The term "complex" as used herein and in the claims means a coordination compound formed by the union of one or more electronically rich molecules or atoms capable of independent existence with one or more electronically poor molecules or atoms, each of which is also capable of independent existence. For example, the ligands employable herein, i.e., organophosphorus ligands, may possess one or more phosphorus donor atoms, each having one available or unshared pair of electrons which are each capable of forming a coordinate covalent bond independently or possibly in concert (e.g., via chelation) with the metal. Carbon monoxide (which is also properly classified as a ligand) can also be present and complexed with the metal. The ultimate composition of the complex catalyst may also contain an additional ligand, e.g., hydrogen or an anion satisfying the coordination sites or nuclear charge of the metal. Illustrative additional ligands include, e.g., halogen (Cl, Br, I), alkyl, aryl, substituted aryl, acyl, $CF_3$, $C_2F_5$, CN, $(R)_2PO$ and $RP(O)(OH)O$ (wherein each R is the same or different and is a substituted or unsubstituted hydrocarbon radical, e.g., the alkyl or aryl), acetate, acetylacetonate, $SO_4$, $BF_4$, $PF_6$, $NO_2$, $NO_3$, $CH_3O$, $CH_2=CHCH_2$, $CH_3CH=CHCH_2$, $C_6H_5CN$, $CH_3CN$, NO, $NH_3$, pyridine, $(C_2H_5)_3N$, mono-olefins, diolefins and triolefins, tetrahydrofuran, and the like. It is of course to be understood that the complex species are preferably free of any additional organic ligand or anion that might poison the catalyst and have an undue adverse effect on catalyst performance. It is preferred in the metal-ligand complex catalyzed hydroformylation reactions that the active catalysts be free of halogen and sulfur directly bonded to the metal, although such may not be absolutely necessary. Preferred metal-ligand complex catalysts include rhodium-organophosphine ligand complex catalysts and rhodium-organophosphite ligand complex catalysts.

The number of available coordination sites on such metals is well known in the art. Thus the catalytic species may comprise a complex catalyst mixture, in their monomeric, dimeric or higher nuclearity forms, which are preferably characterized by at least one phosphorus-containing molecule complexed per metal, e.g., rhodium. As noted above, it is considered that the catalytic species of the preferred catalyst employed in the hydroformylation reaction may be complexed with carbon monoxide and hydrogen in addition to the organophosphorus ligands in view of the carbon monoxide and hydrogen gas employed by the hydroformylation reaction.

Among the organophosphines that may serve as the ligand of the metal-organophosphine complex catalyst and/or free organophosphine ligand of the hydroformylation reaction mixture starting materials are triorganophosphines, trialkylphosphines, alkyldiarylphosphines, dialkylarylphosphines, dicycloalkylarylphosphines, cycloalkyldiarylphosphines, triaralkylphosphines, tricycloalkylphosphines, and triarylphosphines, alkyl and/or aryl diphosphines and bisphosphine mono oxides, as well as ionic triorganophosphines containing at least one ionic moiety selected from the salts of sulfonic acid, of carboxylic acid, of phosphonic acid and of quaternary ammonium compounds, and the like. Of course any of the hydrocarbon radicals of such tertiary non-ionic and ionic organophosphines may be substituted if desired, with any suitable substituent that does not unduly adversely affect the desired result of the hydroformylation reaction. The organophosphine ligands employable in the hydroformylation reaction and/or methods for their preparation are known in the art.

Illustrative triorganophosphine ligands may be represented by the formula:

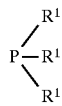  (I)

wherein each $R^1$ is the same or different and is a substituted or unsubstituted monovalent hydrocarbon radical, e.g., an alkyl or aryl radical. Suitable hydrocarbon radicals may contain from 1 to 24 carbon atoms or greater. Illustrative substituent groups that may be present on the aryl radicals include, e.g., alkyl radicals, alkoxy radicals, silyl radicals such as —Si$(R^2)_3$; amino radicals such as —N$(R^2)_2$; acyl radicals such as —C(O)$R^2$; carboxy radicals such as —C(O)O$R^2$; acyloxy radicals such as —OC(O)$R^2$; amido radicals such as —C(O)N$(R^2)_2$ and —N$(R^2)$C(O)$R^2$; ionic radicals such as —$SO_3$M wherein M represents inorganic or organic cationic atoms or radicals; sulfonyl radicals such as —$SO_2R^2$; ether radicals such as —O$R^2$; sulfinyl radicals such as —SO$R^2$; sulfenyl radicals such as —S$R^2$ as well as halogen, nitro, cyano, trifluoromethyl and hydroxy radicals, and the like, wherein each $R^2$ individually represents the same or different substituted or unsubstituted monovalent hydrocarbon radical, with the proviso that in amino substituents such as —N$(R^2)_2$, each $R^2$ taken together can also represent a divalent bridging group that forms a heterocyclic radical with the nitrogen atom and in amido substituents such as C(O)N$(R^2)_2$ and —N$(R^2)$C(O)$R^2$ each —$R^2$ bonded to N can also be hydrogen. Illustrative alkyl radicals include, e.g., methyl, ethyl, propyl, butyl and the like. Illustrative aryl radicals include, e.g., phenyl, naphthyl, diphenyl, fluorophenyl, difluorophenyl, benzoyloxyphenyl, carboethoxyphenyl, acetylphenyl, ethoxyphenyl, phenoxyphenyl, hydroxyphenyl, carboxyphenyl, trifluoromethylphenyl, methoxyethylphenyl, acetamidophenyl, dimethylcarbamylphenyl, tolyl, xylyl, and the like.

Illustrative specific organophosphines include, e.g., triphenylphosphine, tris-p-tolyl phosphine, tris-p-methoxyphenylphosphine, tris-p-fluorophenylphosphine, tris-p-chlorophenylphosphine, tris-dimethylaminophenylphosphine, propyldiphenylphosphine, t-butyldiphenylphosphine, n-butyldiphenylphosphine, n-hexyldiphenylphosphine, cyclohexyldiphenylphosphine, dicyclohexylphenylphosphine, tricyclohexylphosphine, tribenzylphosphine, DIOP, i.e., (4R,5R)-(−)-O-isopropylidene-2,3-dihydroxy-1,4-bis(diphenylphosphino) butane and/or (4S ,5S)-( +)-O-isopropylidene-2,3-dihydroxy-1,4-bis(diphenylphosphino)butane and/or (4S, 5R)-(−)-O-isopropylidene-2,3-dihydroxy-1,4-bis (diphenylphosphino)butane, substituted or unsubstituted bicyclic bisphosphines such as 1,2-bis(1,4-cyclooctylenephosphino)ethane, 1,3-bis(1,4-cyclooctylenephosphino)propane, 1,3-bis(1,5-cyclooctylenephosphino)propane and 1,2-bis(2,6-dimethyl-1,4-cyclooctylenephosphino)ethane, substituted or unsubstituted bis(2,2'-diphenylphosphinomethyl)biphenyl such as bis(2,2'-diphenylphosphinomethyl)biphenyl and bis{2,2'-di(4-fluorophenyl)phosphinomethyl}biphenyl, xantphos, thixantphos, bis(diphenylphosphino)ferrocene, bis(diisopropylphosphino)ferrocene, bis (diphenylphosphino)ruthenocene, as well as the alkali and alkaline earth metal salts of sulfonated triphenylphosphines, e.g., of (tri-m-sulfophenyl)phosphine and of (m-sulfophenyl)diphenyl-phosphine and the like.

More particularly, illustrative metal-organophosphine complex catalysts and illustrative free organophosphine ligands include, e.g., those disclosed in U.S. Pat. Nos. 3,527,809; 4,148,830; 4,247,486; 4,283,562; 4,400,548; 4,482,749, 4,861,918; 4,694,109; 4,742,178; 4,851,581; 4,824,977; 5,332,846; 4,774,362; and WO Patent Application No. 95/30680, published Nov. 16, 1995; the disclosures of which are incorporated herein by reference.

The organophosphites that may serve as the ligand of the metal-organophosphite ligand complex catalyst and/or free ligand of the processes and reaction product mixtures of this invention may be of the achiral (optically inactive) or chiral (optically active) type and are well known in the art.

Among the organophosphites that may serve as the ligand of the metal-organophosphite complex catalyst and/or free organophosphite ligand of the hydroformylation reaction mixture starting materials are monoorganophosphites, diorganophosphites, triorganophosphites and organopolyphosphites. The organophosphite ligands employable in this invention and/or methods for their preparation are known in the art.

Representative monoorganophosphites may include those having the formula:

  (II)

wherein $R^3$ represents a substituted or unsubstituted trivalent hydrocarbon radical containing from 4 to 40 carbon atoms or greater, such as trivalent acyclic and trivalent cyclic radicals, e.g., trivalent alkylene radicals such as those derived from 1,2,2-trimethylolpropane and the like, or trivalent cycloalkylene radicals such as those derived from 1,3,5-trihydroxycyclohexane, and the like. Such monoorganophosphites may be found described in greater detail, e.g., in U.S. Pat. No. 4,567,306, the disclosure of which is incorporated herein by reference.

Representative diorganophosphites may include those having the formula:

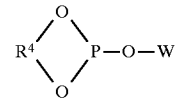  (III)

wherein $R^4$ represents a substituted or unsubstituted divalent hydrocarbon radical containing from 4 to 40 carbon atoms or greater and W represents a substituted or unsubstituted monovalent hydrocarbon radical containing from 1 to 18 carbon atoms or greater.

Representative substituted and unsubstituted monovalent hydrocarbon radicals represented by W in the above formula (III) include alkyl and aryl radicals, while representative substituted and unsubstituted divalent hydrocarbon radicals represented by $R^4$ include divalent acyclic radicals and divalent aromatic radicals. Illustrative divalent acyclic radicals include, e.g., alkylene, alkylene-oxy-alkylene, alkylene-NX-alkylene wherein X is hydrogen or a substituted or unsubstituted monovalent hydrocarbon radical, alkylene-S-alkylene, and cycloalkylene radicals, and the like. The more preferred divalent acyclic radicals are the divalent alkylene radicals such as disclosed more fully, e.g., in U.S. Pat. Nos.

3,415,906 and 4,567,302 and the like, the disclosures of which are incorporated herein by reference. Illustrative divalent aromatic radicals include, e.g., arylene, bisarylene, arylene-alkylene, arylene-alkylene-arylene, arylene-oxy-arylene, arylene-NX-arylene wherein X is as defined above, arylene-S-arylene, and arylene-S-alkylene, and the like. More preferably $R^4$ is a divalent aromatic radical such as disclosed more fully, e.g., in U.S. Pat. Nos. 4,599,206 and 4,717,775, and the like, the disclosures of which are incorporated herein by reference.

Representative of a more preferred class of diorganophosphites are those of the formula:

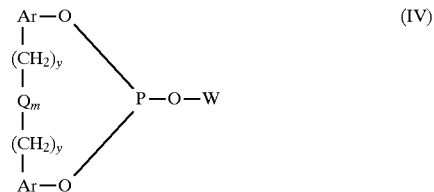

wherein W is as defined above, each Ar is the same or different and represents a substituted or unsubstituted aryl radical, each y is the same or different and is a value of 0 or 1, Q represents a divalent bridging group selected from $-C(R^5)_2-$, $-O-$, $-S-$, $-NR^{6-}$, $Si(R^7)_2-$ and $-CO-$, wherein each $R^5$ is the same or different and represents hydrogen, alkyl radicals having from 1 to 12 carbon atoms, phenyl, tolyl, and anisyl, $R^6$ represents hydrogen or a methyl radical, each $R^7$ is the same or different and represents hydrogen or a methyl radical, and m is a value of 0 or 1. Such diorganophosphites are described in greater detail, e.g., in U.S. Pat. Nos. 4,599,206 and 4,717,775, the disclosures of which are incorporated herein by reference.

Representative triorganophosphites may include those having the formula:

wherein each $R^8$ is the same or different and is a substituted or unsubstituted monovalent hydrocarbon radical, e.g., an alkyl or aryl radical. Suitable hydrocarbon radicals may contain from 1 to 24 carbon atoms or greater and may include those described above for $R^1$ in formula (I).

Representative organopolyphosphites contain two or more tertiary (trivalent) phosphorus atoms and may include those having the formula:

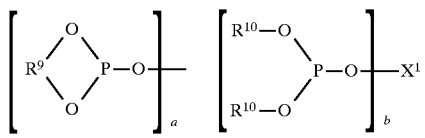

wherein $X^1$ represents a substituted or unsubstituted n-valent hydrocarbon bridging radical containing from 2 to 40 carbon atoms, each $R^9$ is the same or different and is a divalent hydrocarbon radical containing from 4 to 40 carbon atoms, each $R^{10}$ is the same or different and is a substituted or unsubstituted monovalent hydrocarbon radical containing from 1 to 24 carbon atoms, a and b can be the same or different and each have a value of 0 to 6, with the proviso that the sum of a+b is 2 to 6 and n equals a+b. Of course it is to be understood that when a has a value of 2 or more, each $R^9$ radical may be the same or different, and when b has a value of 1 or more, each $R^{10}$ radical may also be the same or different.

Representative n-valent (preferably divalent) hydrocarbon bridging radicals represented by $X^1$, as well as representative divalent hydrocarbon radicals represented by $R^9$ above, include both acyclic radicals and aromatic radicals, such as alkylene, alkylene-$Q_m$-alkylene, cycloalkylene, arylene, bisarylene, arylene-alkylene, and arylene-$(CH_2)_y$-$Q_m$-$(CH_2)_y$-arylene radicals, and the like, wherein Q, m and y are as defined above for formula (IV). The more preferred acyclic radicals represented by $X^1$ and $R^9$ above are divalent alkylene radicals, while the more preferred aromatic radicals represented by $X^1$ and $R^9$ above are divalent arylene and bisarylene radicals, such as disclosed more fully, e.g., in U.S. Pat. Nos. 3,415,906; 4,567,306; 4,599,206; 4,769,498; 4,717,775; 4,885,401; 5,202,297; 5,264,616 and 5,364,950, and the like, the disclosures of which are incorporated herein by reference. Representative monovalent hydrocarbon radicals represented by each $R^{10}$ radical above include alkyl and aromatic radicals.

Illustrative preferred organopolyphosphites may include bisphosphites such as those of formulas (VII) to (IX) below:

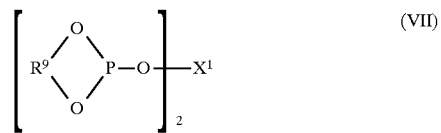

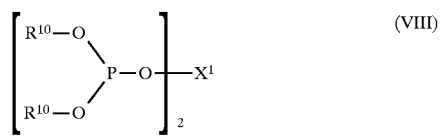

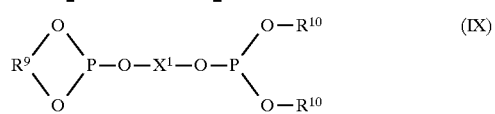

wherein each $R^9$, $R^{10}$ and $X^1$ of formulas (VII) to (IX) are the same as defined above for formula (VI). Preferably, each $R^9$ and $X^1$ represents a divalent hydrocarbon radical selected from alkylene, arylene, arylene-alkylene-arylene, and bisarylene, while each $R^{10}$ represents a monovalent hydrocarbon radical selected from alkyl and aryl radicals. Phosphite ligands of such formulas (VI) to (IX) may be found disclosed, e.g., in said U.S. Pat. Nos. 4,668,651; 4,748,261; 4,769,498; 4,885,401; 5,202,297; 5,235,113; 5,254,741; 5,264,616; 5,312,996; 5,364,950; and 5,391,801; the disclosures of all of which are incorporated herein by reference.

Representative of more preferred classes of organobisphosphites are those of the following formulas (X) to (XII):

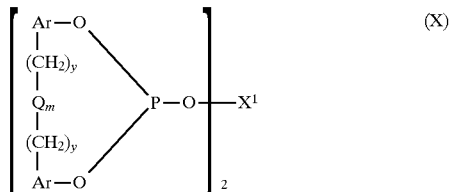

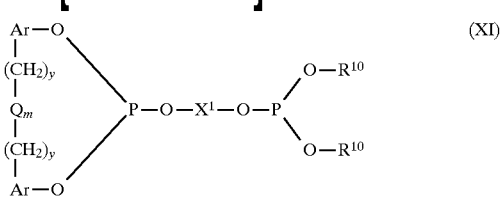

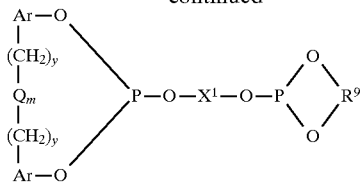

(XII)

wherein Ar, Q, R$^9$, R$^{10}$, X$^1$, m and y are as defined above. Most preferably X$^1$ represents a divalent aryl-(CH$_2$)$_y$—(Q)$_m$—(CH$_2$)$_y$-aryl radical wherein each y individually has a value of 0 or 1; m has a value of 0 or 1 and Q is —O—, —S— or —C(R$^5$)$_2$— wherein each R$^5$ is the same or different and represents a hydrogen or methyl radical. More preferably each alkyl radical of the above defined R$^{10}$ groups may contain from 1 to 24 carbon atoms and each aryl radical of the above-defined Ar, X$^1$, R$^9$ and R$^{10}$ groups of the above formulas (VI) to (XII) may contain from 6 to 18 carbon atoms and said radicals may be the same or different, while the preferred alkylene radicals of X$^1$ may contain from 2 to 18 carbon atoms and the preferred alkylene radicals of R$^9$ may contain from 5 to 18 carbon atoms. In addition, preferably the divalent Ar radicals and divalent aryl radicals of X$^1$ of the above formulas are phenylene radicals in which the bridging group represented by —(CH$_2$)$_y$—(Q)$_m$—(CH$_2$)$_y$— is bonded to said phenylene radicals in positions that are ortho to the oxygen atoms of the formulas that connect the phenylene radicals to their phosphorus atom of the formulas. It is also preferred that any substituent radical when present on such phenylene radicals be bonded in the para and/or ortho position of the phenylene radicals in relation to the oxygen atom that bonds the given substituted phenylene radical to its phosphorus atom.

Moreover, if desired any given organophosphite in the above formulas (VI) to (XII) may be an ionic phosphite, i.e., may contain one or more ionic moieties selected from the group consisting of:

SO$_3$M wherein M represents inorganic or organic cation,

PO$_3$M wherein M represents inorganic or organic cation,

N(R$^{11}$)$_3$X$^2$ wherein each R$^{11}$ is the same or different and represents a hydrocarbon radical containing from 1 to 30 carbon atoms, e.g, alkyl, aryl, alkaryl, aralkyl, and cycloalkyl radicals, and X$^2$ represents inorganic or organic anion, CO$_2$M wherein M represents inorganic or organic cation, as described, e.g., in U.S. Pat. Nos. 5,059,710; 5,113,022, 5,114,473 and 5,449,653, the disclosures of which are incorporated herein by reference. Thus, if desired, such phosphite ligands may contain from 1 to 3 such ionic moieties, while it is preferred that only one such ionic moiety be substituted on any given aryl moiety in the phosphite ligand when the ligand contains more than one such ionic moiety. As suitable counter-ions, M and X$^2$, for the anionic moieties of the ionic phosphites there can be mentioned hydrogen (i.e. a proton), the cations of the alkali and alkaline earth metals, e.g., lithium, sodium, potassium, cesium, rubidium, calcium, barium, magnesium and strontium, the ammonium cation, quaternary ammonium cations, phosphonium cations, arsonium cations and iminium cations. Suitable anionic groups include, for example, sulfate, carbonate, phosphate, chloride, acetate, oxalate and the like.

Of course any of the R$^9$, R$^{10}$, X$^2$ and Ar radicals of such non-ionic and ionic organophosphites of formulas (VI) to (XII) above may be substituted if desired, with any suitable substituent containing from 1 to 30 carbon atoms that does not unduly adversely affect the desired result of the hydroformylation reaction. Substituents that may be on said radicals in addition of course to corresponding hydrocarbon radicals such as alkyl, aryl, aralkyl, alkaryl and cyclohexyl substituents, may include for example silyl radicals such as —Si(R$^{12}$)$_3$; amino radicals such as —N(R$^{12}$)$_2$; phosphine radicals such as -aryl-P(R$^{12}$)$_2$; acyl radicals such as —C(O)R$^{12}$; acyloxy radicals such as —OC(O)R$^{12}$; amido radicals such as —CON(R$^{12}$)$_2$ and —N(R$^{12}$)COR$^{12}$; sulfonyl radicals such as —SO$_2$R$^{12}$; alkoxy radicals such as —OR$^{12}$; sulfinyl radicals such as —SOR$^{12}$; sulfenyl radicals such as —SR$^{12}$; phosphonyl radicals such as —P(O)(R$^{12}$)$_2$; as well as, halogen, nitro, cyano, trifluoromethyl, hydroxy radicals, and the like, wherein each R$^{12}$ radical is the same or different and represents a monovalent hydrocarbon radical having from 1 to 18 carbon atoms (e.g., alkyl, aryl, aralkyl, alkaryl and cyclohexyl radicals), with the proviso that in amino substituents such as —N(R$^{12}$)$_2$ each R$^{12}$ taken together can also represent a divalent bridging group that forms a heterocyclic radical with the nitrogen atom, and in amido substituents such as —C(O)N(R$^{12}$)$_2$ and —N(R$^{12}$)COR$^{12}$ each R$^{12}$ bonded to N can also be hydrogen. Of course it is to be understood that any of the substituted or unsubstituted hydrocarbon radicals groups that make up a particular given organophosphite may be the same or different.

More specifically illustrative substituents include primary, secondary and tertiary alkyl radicals such as methyl, ethyl, n-propyl, isopropyl, butyl, sec-butyl, t-butyl, neo-pentyl, n-hexyl, amyl, sec-amyl, t-amyl, iso-octyl, decyl, octadecyl, and the like; aryl radicals such as phenyl, naphthyl and the like; aralkyl radicals such as benzyl, phenylethyl, triphenylmethyl, and the like; alkaryl radicals such as tolyl, xylyl, and the like; alicyclic radicals such as cyclopentyl, cyclohexyl, 1-methylcyclohexyl, cyclooctyl, cyclohexylethyl, and the like; alkoxy radicals such as methoxy, ethoxy, propoxy, t-butoxy, —OCH$_2$CH$_2$OCH$_3$, —(OCH$_2$CH$_2$)$_2$OCH$_3$, —(OCH$_2$CH$_2$)$_3$OCH$_3$, and the like; aryloxy radicals such as phenoxy and the like; as well as silyl radicals such as —Si(CH$_3$)$_3$, —Si(OCH$_3$)$_3$, —Si(C$_3$H$_7$)$_3$, and the like; amino radicals such as —NH$_2$, —N(CH$_3$)$_2$, —NHCH$_3$, —NH(C$_2$H$_5$), and the like; arylphosphine radicals such as —P(C$_6$H$_5$)$_2$, and the like; acyl radicals such as —C(O)CH$_3$, —C(O)C$_2$H$_5$, —C(O)C$_6$H$_5$, and the like; carbonyloxy radicals such as —C(O)OCH$_3$ and the like; oxycarbonyl radicals such as —O(CO)C$_6$H$_5$, and the like; amido radicals such as —CONH$_2$, —CON(CH$_3$)$_2$, —NHC(O)CH$_3$, and the like; sulfonyl radicals such as —S(O)$_2$C$_2$H$_5$ and the like; sulfinyl radicals such as —S(O)CH$_3$ and the like; sulfenyl radicals such as —SCH$_3$, —SC$_2$H$_5$, —SC$_6$H$_5$, and the like; phosphonyl radicals such as —P(O)(C$_6$H$_5$)$_2$, —P(O)(CH$_3$)$_2$, —P(O)(C$_2$H$_5$)$_2$, —P(O)(C$_3$H$_7$)$_2$, —P(O)(C$_4$H$_9$)$_2$, —P(O)(C$_6$H$_{13}$)$_2$, —P(O)CH$_3$(C$_6$H$_5$), —P(O)(H)(C$_6$H$_5$), and the like.

Specific illustrative examples of such organophosphite ligands include the following:

2-t-butyl-4-methoxyphenyl(3,3'-di-t-butyl-5,5'-dimethoxy-1,1'-biphenyl-2,2'-diyl)phosphite having the formula:

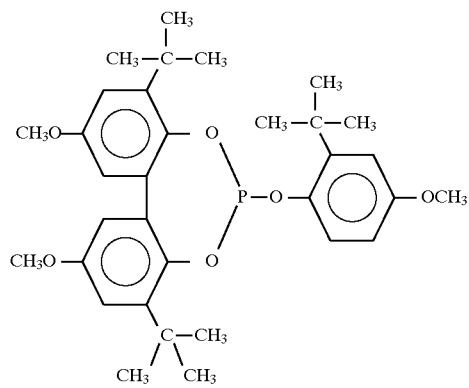

methyl(3,3'-di-t-butyl-5,5'-dimethoxy-1,1'-biphenyl-2,2'-diyl)phosphite having the formula:

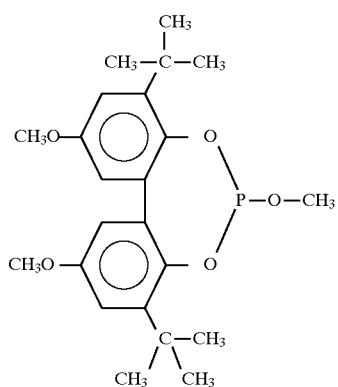

6,6'-[[4,4'-bis(1,1-dimethylethyl)-[1,1'-binaphthyl]-2,2'-diyl]bis(oxy)]bis-dibenzo [d,f][1,3,2]-dioxaphosphepin having the formula:

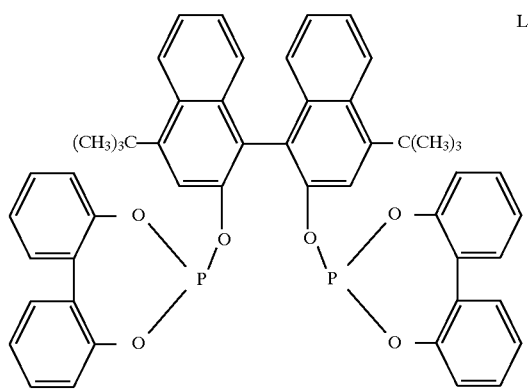

6,6'-[[3,3'-bis(1,1-dimethylethyl)-5,5'-dimethoxy-[1,1'-biphenyl]-2,2'-diyl]bis(oxy)]bis-dibenzo[d,f][1,3,2]dioxaphosphepin having the formula:

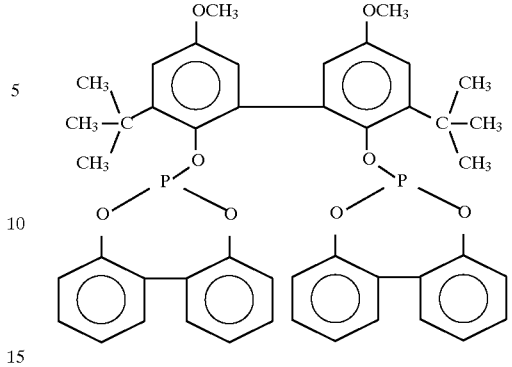

6,6'-[[3,3',5,5'-tetrakis(1,1-dimethylpropyl)-[1,1'-biphenyl]-2,2'-diyl]bis(oxy)]bis-dibenzo [d,f][1,3,2]dioxaphosphepin having the formula:

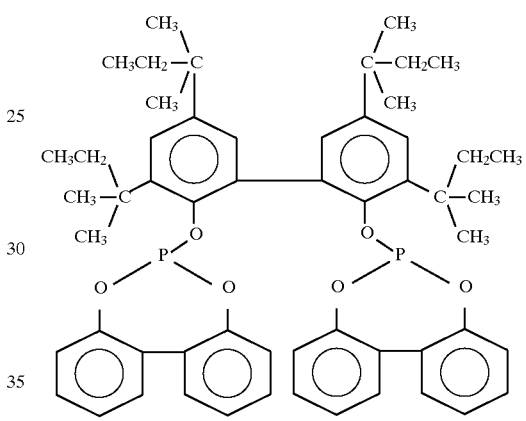

6,6'-[[3,3',5,5'-tetrakis(1,1-dimethylethyl)-1,1'-biphenyl]-2,2'-diyl]bis(oxy)]bis-dibenzo [d,f][1,3,2]-dioxaphosphepin having the formula:

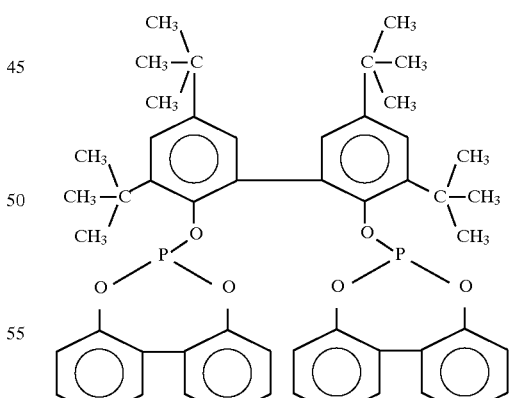

(2R,4R)-di[2,2'-(3,3',5,5'-tetrakis-tert-amyl-1,1'-biphenyl)]-2,4-pentyldiphosphite having the formula:

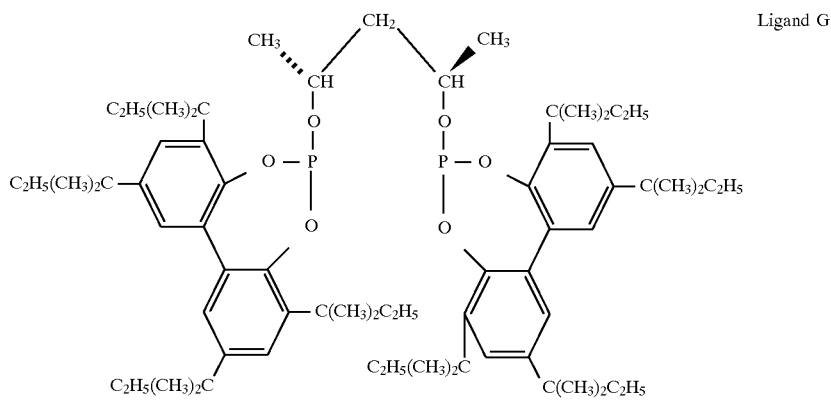
Ligand G
(2R,4R)-di[2,2'-(3,3',5,5'-tetrakis-tert-butyl-1,1'-biphenyl)]-2,4-pentyldiphosphite having the formula:
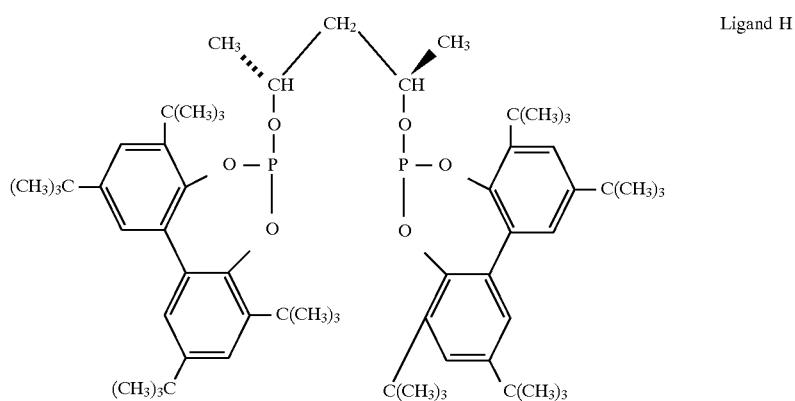
Ligand H
(2R,4R)-di[2,2'-(3,3'-di-amyl-5,5'-dimethoxy-1,1'-biphenyl)]-2,4-pentyldiphosphite having the formula:
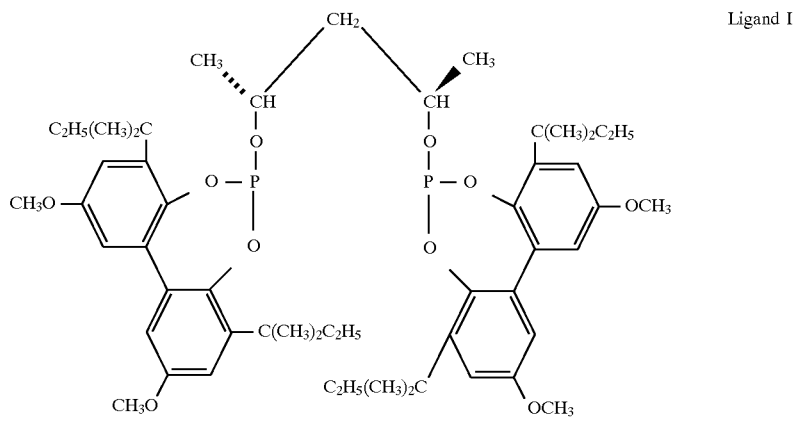
Ligand I
(2R,4R)-di[2,2'-(3,3'-di-tert-butyl-5,5'-dimethyl-1,1'-biphenyl)]-2,4-pentyldiphosphite having the formula:

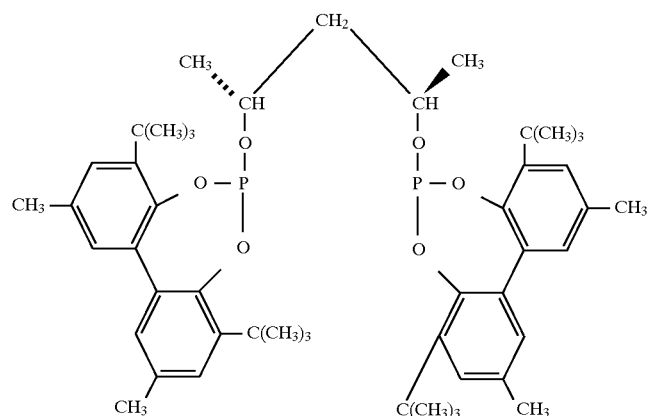
Ligand J
(2R,4R)-di[2,2'-(3,3'-di-tert-butyl-5,5'-diethoxy-1,1'-biphenyl)]-2,4-pentyldiphosphite having the formula:
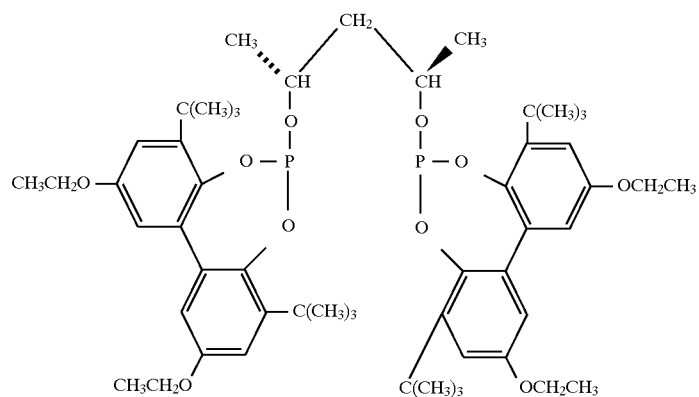
Ligand K
(2R,4R)-di[2,2'-(3,3'-di-tert-butyl-5,5'-diethyl-1,1'-biphenyl)]-2,4-pentyldiphosphite having the formula:
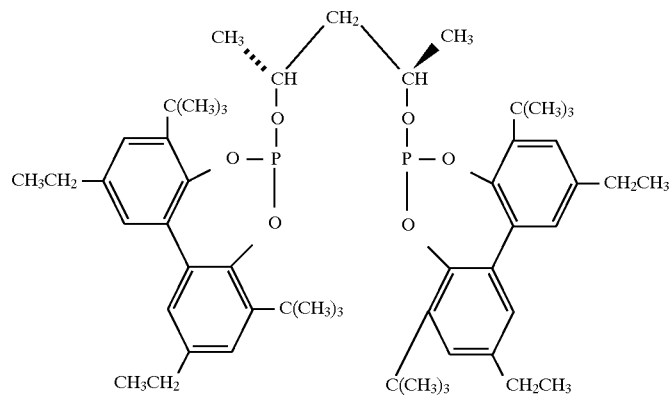
Ligand L
(2R,4R)-di[2,2'-(3,3'-di-tert-butyl-5,5'-dimethoxy-1,1'-biphenyl)]-2,4-pentyldiphosphite having the formula:

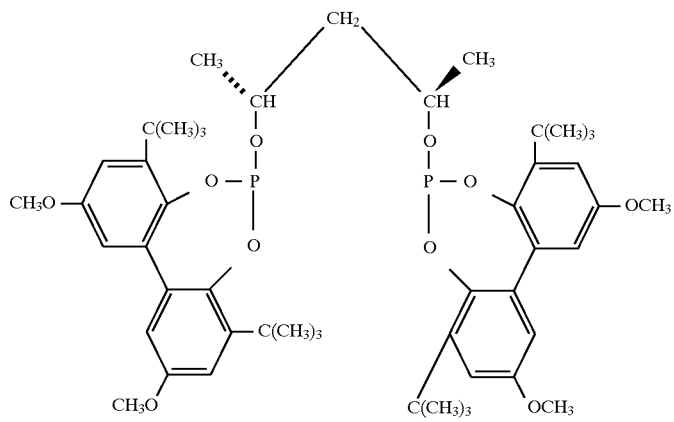

Ligand M

6-[[2'-[(4,6-bis(1,1-dimethylethyl)-1,3,2-benzodioxaphosphol-2-yl)oxy]-3,3'-bis(1,1-dimethylethyl)-5,5'-dimethoxy [1,1'-biphenyl]-2-yl]oxy]-4,8-bis(1,1-dimethylethyl)-2,10-dimethoxydibenzo[d,f][1,3,2]dioxaphosphepin having the formula:

6-[[2'-[(5,5-dimethyl-1,3,2-dioxaphosphorinan-2-yl)oxy]-3,3'-bis (1,1-dimethylethyl)-5,5'-dimethoxy[1,1'-biphenyl]-2-yl]oxy]-4,8-bis(1,1-dimethylethyl)-2,10-dimethoxydibenzo [d,f][1,3,2]dioxaphosphepin having the formula:

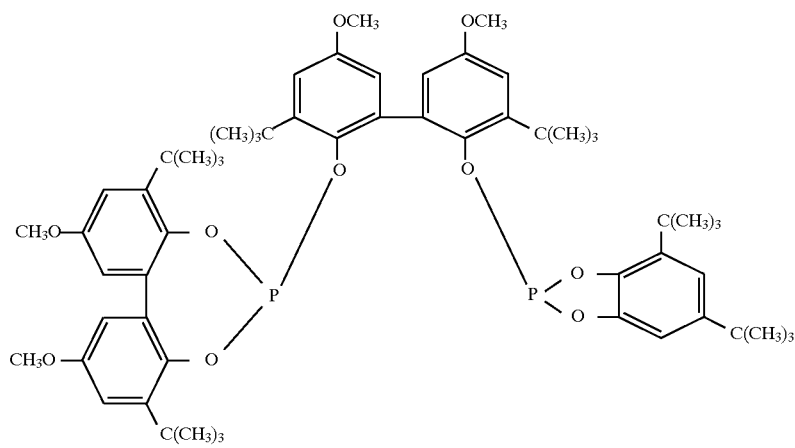

Ligand N

6-[[2'-[1,3,2-benzodioxaphosphol-2-yl)oxy]-3,3'-bis(1,1-dimethylethyl)-5,5'-dimethoxy[1,1'-biphenyl]-2-yl]oxy]-4,8-bis(1,1-dimethylethyl)-2,10-dimethoxydibenzo[d,f][1,3,2]dioxaphosphepin having the formula:

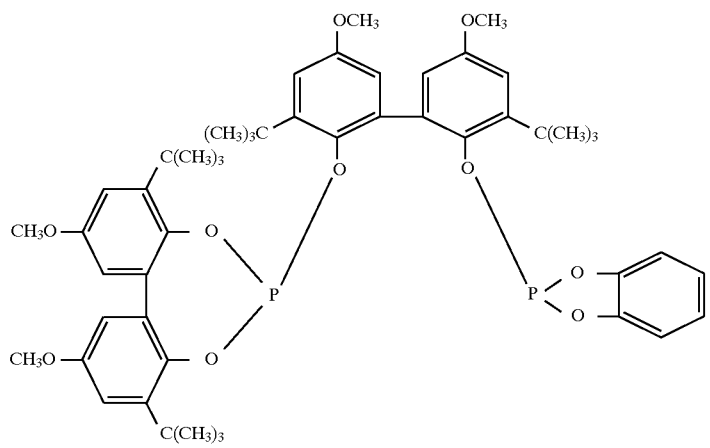

Ligand O

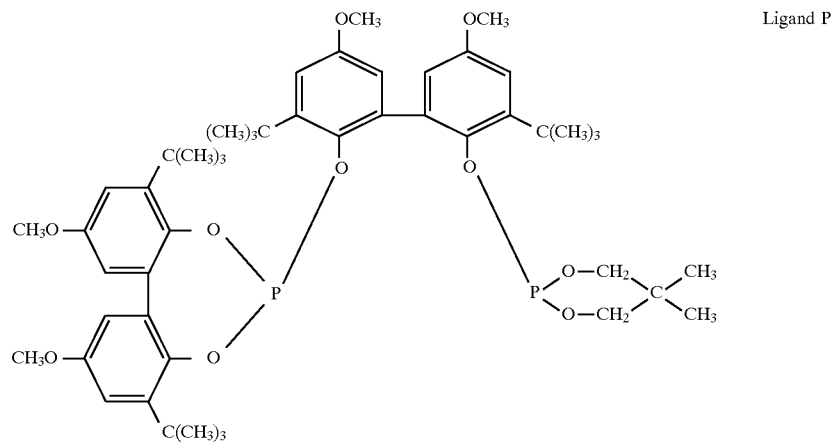

Ligand P

2'-[[4,8-bis(1,1-dimethylethyl)-2,10-dimethoxydibenzo[d,f][1,3,2]-dioxaphosphepin-6-yl]oxyl]-3,3'-bis( 1,1-dimethylethyl)-5,5'-dimethoxyl [1,1'-biphenyl]-2-yl bis(4-hexylphenyl)ester of phosphorous acid having the formula:

3-(1,1-dimethylethyl)-5-methoxyphenyl]methyl]-4-methoxy, 6-(1,1-dimethylethyl)phenyl diphenyl ester of phosphorous acid having the formula:

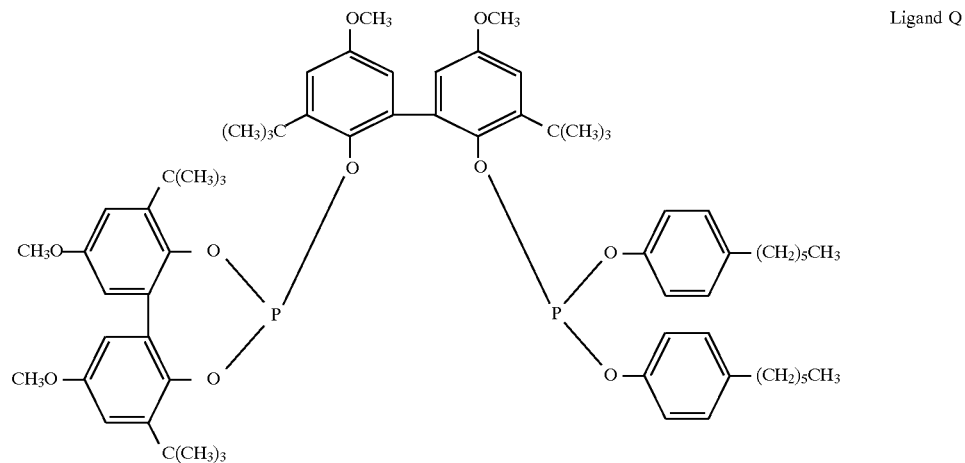

Ligand Q

2-[[2-[[4,8,-bis(1,1-dimethylethyl), 2,10-dimethoxydibenzo-[d,f][1,3,2]dioxophosphepin-6-yl]oxy]-

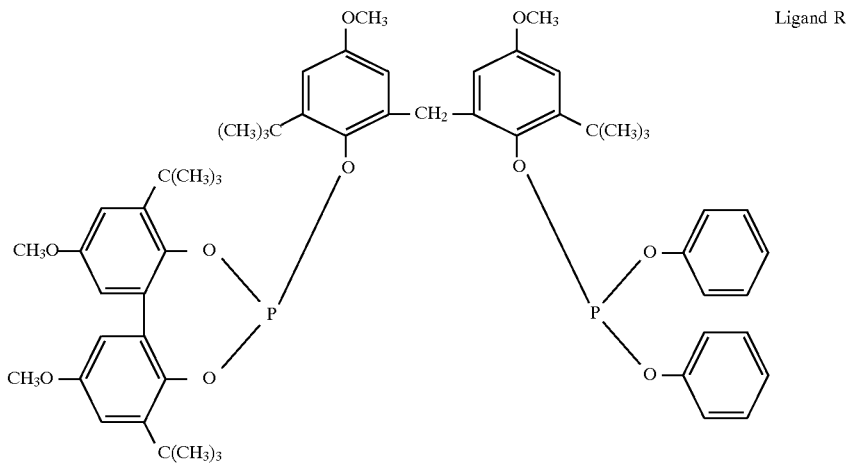

Ligand R 3-methoxy-1,3-cyclohexamethylene tetrakis[3,6-bis(1,1-dimethylethyl)-2-naphthalenyl]ester of phosphorous acid having the formula:

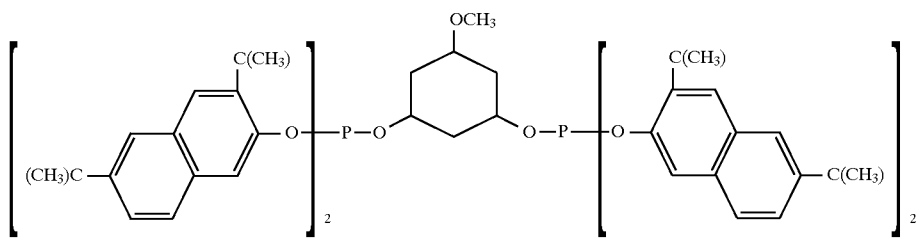

Ligand S 2,5-bis(1,1-dimethylethyl)-1,4-phenylene tetrakis[2,4-bis(1,1-dimethylethyl)phenyl]ester of phosphorous acid having the formula:

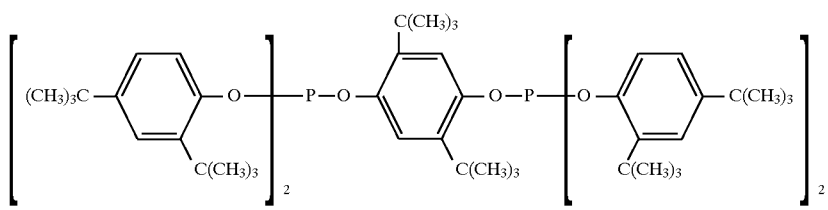

Ligand T methylenedi-2,1-phenylene tetrakis[2,4-bis(1,1-dimethylethyl)phenyl]ester of phosphorous acid having the formula:

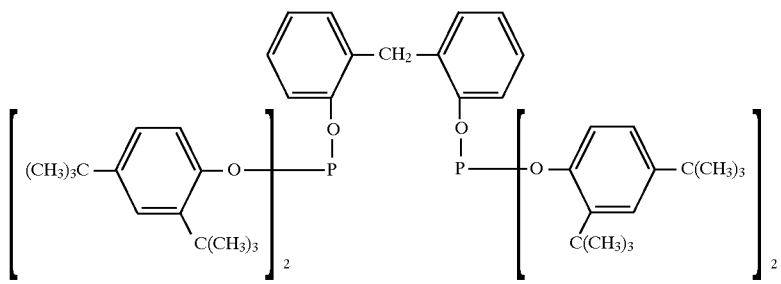

Ligand U

[1,1'-biphenyl]-2,2'-diyl tetrakis[2-(1,1-dimethylethyl)-4-methoxyphenyl]ester of phosphorous acid having the formula:

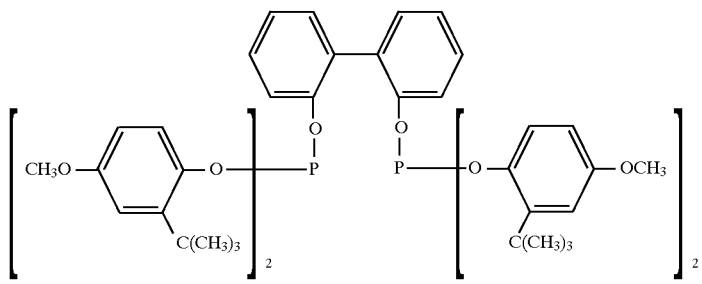

Ligand V

Still other illustrative organophosphorus ligands useful in this invention include those disclosed in U.S. patent application Ser. No. (D-17459-1), filed on an even date herewith, the disclosure of which is incorporated herein by reference.

The metal-ligand complex catalysts employable in this invention may be formed by methods known in the art. The metal-ligand complex catalysts may be in homogeneous or heterogeneous form. For instance, preformed metal hydrido-carbonyl-organophosphorus ligand catalysts may be prepared and introduced into the reaction mixture of a hydroformylation process. More preferably, the metal-organophosphorus ligand complex catalysts can be derived from a metal catalyst precursor which may be introduced into the reaction medium for in situ formation of the active catalyst. For example, rhodium catalyst precursors such as rhodium dicarbonyl acetylacetonate, $Rh_2O_3$, $Rh_4(CO)_{12}$, $Rh_6(CO)_{16}$, $Rh(NO_3)_3$ and the like may be introduced into the reaction mixture along with the organophosphorus ligand for the in situ formation of the active catalyst. In a preferred embodiment of this invention, rhodium dicarbonyl acetylacetonate is employed as a rhodium precursor and reacted in the presence of a solvent with the organophosphorus ligand to form a catalytic rhodium-organophosphorus ligand complex precursor which is introduced into the reactor along with excess free organophosphorus ligand for the in situ formation of the active catalyst. In any event, it is sufficient for the purpose of this invention that carbon monoxide, hydrogen and organophosphorus compound are all ligands that are capable of being complexed with the metal and that an active metal-ligand catalyst is present in the reaction mixture under the conditions used in the hydroformylation reaction.

More particularly, a catalyst precursor composition can be formed consisting essentially of a solubilized metal-ligand complex precursor catalyst, an organic solvent and free ligand. Such precursor compositions may be prepared by forming a solution of a metal starting material, such as a metal oxide, hydride, carbonyl or salt, e.g. a nitrate, which may or may not be in complex combination with a ligand as defined herein. Any suitable metal starting material may be employed, e.g. rhodium dicarbonyl acetylacetonate, $Rh_2O_3$, $Rh_4(CO)_{12}$, $Rh_6(CO)_{16}$, $Rh(NO_3)_3$, and organophosphorus ligand rhodium carbonyl hydrides. Carbonyl and organophosphorus ligands, if not already complexed with the initial metal, may be complexed to the metal either prior to or in situ during the hydroformylation process.

By way of illustration, the preferred catalyst precursor composition of this invention consists essentially of a solubilized rhodium carbonyl organophosphorus ligand complex precursor catalyst, a solvent and free organophosphorus ligand prepared by forming a solution of rhodium dicarbonyl acetylacetonate, an organic solvent and a ligand as defined herein. The organophosphorus ligand readily replaces one of the carbonyl ligands of the rhodium acetylacetonate complex precursor at room temperature as witnessed by the evolution of carbon monoxide gas. This substitution reaction may be facilitated by heating the solution if desired. Any suitable organic solvent in which both the rhodium dicarbonyl acetylacetonate complex precursor and rhodium organophosphorus ligand complex precursor are soluble can be employed. The amounts of rhodium complex catalyst precursor, organic solvent and organophosphorus ligand, as well as their preferred embodiments present in such catalyst precursor compositions may obviously correspond to those amounts employable in the hydroformylation process of this invention. Experience has shown that the acetylacetonate ligand of the precursor catalyst is replaced after the hydroformylation process has begun with a different ligand, e.g., hydrogen, carbon monoxide or organophosphorus ligand, to form the active complex catalyst as explained above. In a continuous process, the acetylacetone which is freed from the precursor catalyst under hydroformylation conditions is removed from the reaction medium with the product aldehyde and thus is in no way detrimental to the hydroformylation process. The use of such preferred rhodium complex catalytic precursor compositions provides a simple economical and efficient method for handling the rhodium precursor metal and hydroformylation start-up.

Accordingly, the metal-ligand complex catalysts used in the process of this invention consists essentially of the metal complexed with carbon monoxide and a ligand, said ligand being bonded (complexed) to the metal in a chelated and/or non-chelated fashion. Moreover, the terminology "consists essentially of", as used herein, does not exclude, but rather includes, hydrogen complexed with the metal, in addition to carbon monoxide and the ligand. Further, such terminology does not exclude the possibility of other organic ligands and/or anions that might also be complexed with the metal. Materials in amounts which unduly adversely poison or unduly deactivate the catalyst are not desirable and so the catalyst most desirably is free of contaminants such as metal-bound halogen (e.g., chlorine, and the like) although such may not be absolutely necessary. The hydrogen and/or carbonyl ligands of an active metal-ligand complex catalyst may be present as a result of being ligands bound to a precursor catalyst and/or as a result of in situ formation, e.g., due to the hydrogen and carbon monoxide gases employed in hydroformylation process of this invention.

As noted the hydroformylation reactions involve the use of a metal-ligand complex catalyst as described herein. Of course mixtures of such catalysts can also be employed if desired. Mixtures of hydroformylation catalysts and hydrocarbonylation catalysts may also be employed if desired. The amount of metal-ligand complex catalyst present in the reaction medium of a given hydroformylation reaction need only be that minimum amount necessary to provide the given metal concentration desired to be employed and which will furnish the basis for at least the catalytic amount of metal necessary to catalyze the particular hydroformylation reaction involved such as disclosed e.g. in the above-mentioned patents. In general, the catalyst concentration can range from several parts per million to several percent by weight. Organophosphorus ligands can be employed in the above-mentioned catalysts in a molar ratio of generally from about 0.5:1 or less to about 1000:1 or greater. The catalyst concentration will be dependent on the hydroformylation reaction conditions and solvent employed.

In general, the organophosphorus ligand concentration in hydroformylation reaction mixtures may range from between about 0.005 and 25 weight percent based on the total weight of the reaction mixture. Preferably the ligand concentration is between 0.01 and 15 weight percent, and more preferably is between about 0.05 and 10 weight percent on that basis.

In general, the concentration of the metal in the hydroformylation reaction mixtures may be as high as about 2000 parts per million by weight or greater based on the weight of the reaction mixture. Preferably the metal concentration is between about 50 and 1000 parts per million by weight based on the weight of the reaction mixture, and more preferably is between about 70 and 800 parts per million by weight based on the weight of the reaction mixture.

In addition to the metal-ligand complex catalyst, free ligand (i.e., ligand that is not complexed with the rhodium metal) may also be present in the hydroformylation reaction medium. The free ligand may correspond to any of the above-defined phosphorus-containing ligands discussed above as employable herein. It is preferred that the free ligand be the same as the ligand of the metal-ligand complex catalyst employed. However, such ligands need not be the same in any given process. The hydroformylation reaction may involve up to 100 moles, or higher, of free organophosphorus ligand per mole of metal in the hydroformylation reaction medium. Preferably the hydroformylation reaction is carried out in the presence of from about 0.25 to about 50 moles of coordinatable phosphorus, and more preferably from about 0.5 to about 30 moles of coordinatable phosphorus, per mole of metal present in the reaction medium; said amounts of coordinatable phosphorus being the sum of both the amount of coordinatable phosphorus that is bound (complexed) to the rhodium metal present and the amount of free (non-complexed) coordinatable phosphorus present. Of course, if desired, make-up or additional coordinatable phosphorus can be supplied to the reaction medium of the hydroformylation reaction at any time and in any suitable manner, e.g. to maintain a predetermined level of free ligand in the reaction medium.

As indicated above, the hydroformylation catalyst may be in heterogeneous form during the reaction and/or during the product separation. Such catalysts are particularly advantageous in the hydroformylation of olefins or alkadienes to produce high boiling or thermally sensitive aldehydes, so that the catalyst may be separated from the products by filtration or decantation at low temperatures. For example, the rhodium catalyst may be attached to a support so that the catalyst retains its solid form during both the hydroformylation and separation stages, or is soluble in a liquid reaction medium at high temperatures and then is precipitated on cooling.

As an illustration, the rhodium catalyst may be impregnated onto any solid support, such as inorganic oxides, (e.g., alumina, silica, titania, or zirconia) carbon, or ion exchange resins. The catalyst may be supported on, or intercalated inside the pores of, a zeolite or glass; the catalyst may also be dissolved in a liquid film coating the pores of said zeolite or glass. Such zeolite-supported catalysts are particularly advantageous for producing one or more regioisomeric aldehydes in high selectivity, as determined by the pore size of the zeolite. The techniques for supporting catalysts on solids, such as incipient wetness, which will be known to those skilled in the art. The solid catalyst thus formed may still be complexed with one or more of the ligands defined above. Descriptions of such solid catalysts may be found in for example: J. Mol. Cat. 1991, 70, 363–368; Catal. Lett. 1991, 8, 209–214; J. Organomet. Chem, 1991, 403, 221–227; Nature, 1989, 339, 454–455; J. Catal. 1985, 96, 563–573; J. Mol. Cat. 1987, 39, 243–259.

The rhodium catalyst may be attached to a thin film or membrane support, such as cellulose acetate or polyphenylenesulfone, as described in for example J. Mol. Cat. 1990, 63, 213–221.

The rhodium catalyst may be attached to an insoluble polymeric support through an organophosphorus-containing ligand, such as a phosphine or phosphite, incorporated into the polymer. Such polymer-supported ligands are well known, and include such commercially available species as the divinylbenzene/polystyrene-supported supported triphenylphosphine. The supported ligand is not limited by the choice of polymer or phosphorus-containing species incorporated into it. Descriptions of polymer-supported catalysts may be found in for example: J. Mol. Cat. 1993, 83, 17–35; Chemtech 1983, 46; J. Am. Chem. Soc. 1987, 109, 7122–7127.

In the heterogeneous catalysts described above, the catalyst may remain in its heterogeneous form during the entire hydroformylation and catalyst separation process. In another embodiment of the invention, the catalyst may be supported on a polymer which, by the nature of its molecular weight, is soluble in the reaction medium at elevated temperatures, but precipitates upon cooling, thus facilitating catalyst separation from the reaction mixture. Such "soluble" polymer-supported catalysts are described in for example: Polymer, 1992, 33, 161; J. Org. Chem. 1989, 54, 2726–2730.

When the rhodium catalyst is in a heterogeneous or supported form, the reaction may be carried out in the gas phase. More preferably, the reaction is carried out in the slurry phase due to the high boiling points of the products, and to avoid decomposition of the product aldehydes. The catalyst may then be separated from the product mixture by filtration or decantation.

The hydroformylation reaction conditions may include any suitable type hydroformylation conditions heretofore employed for producing aldehydes. For instance, the total gas pressure of hydrogen, carbon monoxide and olefin or alkadiene starting compound of the hydroformylation process may range from about 1 to about 10,000 psia. In general, the hydroformylation process is operated at a total gas pressure of hydrogen, carbon monoxide and olefin or alkadiene starting compound of less than about 1500 psia and more preferably less than about 1000 psia, the minimum total pressure being limited predominately by the amount of reactants necessary to obtain a desired rate of reaction. The total pressure employed in the hydroformylation reaction may range in general from about 20 to about 3000 psia, preferably from about 50 to 1500 psia. The total pressure of the hydroformylation process will be dependent on the particular catalyst system employed.

More specifically, the carbon monoxide partial pressure of the hydroformylation process in general may range from about 1 to about 3000 psia, and preferably from about 3 to about 1500 psia, while the hydrogen partial pressure in general may range from about 1 to about 3000 psia, and preferably from about 3 to about 1500 psia. In general, the molar ratio of carbon monoxide to gaseous hydrogen may range from about 100:1 or greater to about 1:100 or less, the preferred carbon monoxide to gaseous hydrogen molar ratio being from about 1:10 to about 10:1. The carbon monoxide and hydrogen partial pressures will be dependent in part on the particular catalyst system employed.

Carbon monoxide partial pressure should be sufficient for the hydroformylation reaction, e.g., of an unsaturated alcohol, to 6-hydroxyhexanal to occur at an acceptable rate. Hydrogen partial pressure must be sufficient for the hydroformylation reaction to occur at an acceptable rate, but not so high that hydrogenation of butadiene or isomerization of penten-1-ols to undesired isomers occurs. It is understood that carbon monoxide and hydrogen can be employed separately, in mixture with each other, i.e., synthesis gas, or may in part be produced in situ under reaction conditions.

Further, the hydroformylation process may be conducted at a reaction temperature from about 20° C. to about 200° C. may be employed, preferably from about 50° C. to about 150° C., and more preferably from about 65° C. to about 115° C. The temperature must be sufficient for reaction to occur (which may vary with catalyst system employed), but not so high that ligand or catalyst decomposition occurs. At high temperatures (which may vary with catalyst system employed), isomerization of penten-1-ols to undesired isomers may occur.

Of course, it is to be also understood that the hydroformylation reaction conditions employed will be governed by the aldehyde product desired.

In the penten-1-ol hydroformylation step of this invention, the penten-1-ol hydroformylation reaction can be conducted at a penten-1-ol conversion and/or carbon monoxide partial pressure sufficient to selectively produce the 6-hydroxyhexanals. In the penten-1-ol hydroformylation reaction, the penten-1-ol conversion may be complete or incomplete, and the partial pressure of carbon monoxide may be higher or lower than the partial pressure of hydrogen as described above.

The hydroformylation reaction is also conducted in the presence of water or an organic solvent for the metal-ligand complex catalyst and free ligand. Depending on the particular catalyst and reactants employed, suitable organic solvents include, for example, alcohols, alkanes, alkenes, alkynes, ethers, aldehydes, higher boiling aldehyde condensation byproducts, ketones, esters, amides, tertiary amines, aromatics and the like. Any suitable solvent which does not unduly adversely interfere with the intended hydroformylation reaction can be employed and such solvents may include those disclosed heretofore commonly employed in known metal catalyzed hydroformylation reactions. Mixtures of one or more different solvents may be employed if desired. In general, with regard to the production of aldehydes, it is preferred to employ aldehyde compounds corresponding to the aldehyde products desired to be produced and/or higher boiling aldehyde liquid condensation byproducts as the main organic solvents as is common in the art. Such aldehyde condensation byproducts can also be preformed if desired and used accordingly. Illustrative preferred solvents employable in the production of aldehydes include ketones (e.g. acetone and methylethyl ketone), esters (e.g. ethyl acetate), hydrocarbons (e.g. toluene), nitrohydrocarbons (e.g. nitrobenzene), ethers (e.g. tetrahydrofuran (THF) and glyme), 1,4-butanediols and sulfolane. Suitable solvents are disclosed in U.S. Pat. No. 5,312,996. The amount of solvent employed is not critical to the subject invention and need only be that amount sufficient to solubilize the catalyst and free ligand of the hydroformylation reaction mixture to be treated. In general, the amount of solvent may range from about 5 percent by weight up to about 99 percent by weight or more based on the total weight of the hydroformylation reaction mixture starting material.

In an embodiment of the invention, the hydroformylation reaction mixture may consist of one or more liquid phases, e.g. a polar and a nonpolar phase. Such processes are often advantageous in, for example, separating products from catalyst and/or reactants by partitioning into either phase. In addition, product selectivities dependent upon solvent properties may be increased by carrying out the reaction in that solvent. An application of this technology is the aqueous-phase hydroformylation of olefins or alkadienes employing sulfonated phosphine ligands for the rhodium catalyst. A process carried out in aqueous solvent is particularly advantageous for the preparation of aldehydes because the products may be separated from the catalyst by extraction into an organic solvent. Alternatively, aldehydes which tend to undergo self-condensation reactions, are expected to be stabilized in aqueous solution as the aldehyde hydrates.

As described herein, the phosphorus-containing ligand for the rhodium hydroformylation catalyst may contain any of a number of substituents, such as cationic or anionic substituents, which will render the catalyst soluble in a polar phase, e.g. water. Optionally, a phase-transfer catalyst may be added to the reaction mixture to facilitate transport of the catalyst, reactants, or products into the desired solvent phase. The structure of the ligand or the phase-transfer catalyst is not critical and will depend on the choice of conditions, reaction solvent, and desired products.

When the catalyst is present in a multiphasic system, the catalyst may be separated from the reactants and/or products by conventional methods such as extraction or decantation. The reaction mixture itself may consist of one or more phases; alternatively, the multiphasic system may be created at the end of the reaction by for example addition of a second solvent to separate the products from the catalyst. See, for example, U.S. Pat. No. 5,180,854, the disclosure of which is incorporated herein by reference.

In an embodiment of the process of this invention, an olefin can be hydroformylated along with an unsaturated alcohol or alkadiene using the above-described metal-ligand complex catalysts. In such cases, an aldehyde derivative of the olefin is also produced along with the hydroxyaldehydes or pentenals. It has been found that the unsaturated alcohol reacts to form a complex with the metal more rapidly than certain of the olefins and requires more forcing conditions to be hydroformylated itself than certain of the olefins.

Mixtures of different olefinic or alkadiene starting materials can be employed, if desired, in the hydroformylation reactions. More preferably the hydroformylation reactions are especially useful for the production of 6-hydroxyhexanals, by hydroformylating unsaturated alcohols in the presence of alpha olefins containing from 2 to 30, preferably 4 to 20, carbon atoms, including isobutylene, and internal olefins containing from 4 to 20 carbon atoms as well as starting material mixtures of such alpha olefins and internal olefins. Commercial alpha olefins containing four or more carbon atoms may contain minor amounts of corresponding internal olefins and/or their corresponding saturated hydrocarbon and that such commercial olefins need not necessarily be purified from same prior to being hydroformylated.

Illustrative of other olefinic starting materials include alpha-olefins, internal olefins, 1,3-dienes, alkyl alkenoates, alkenyl alkanoates, alkenyl alkyl ethers, alkenols, alkenals, and the like, e.g., ethylene, propylene, 1-butene, 1-pentene, 1-hexene, 1-octene, 1-nonene, 1-decene, 1-undecene, 1-dodecene, 1-tridecene, 1-tetradecene, 1-pentadecene, 1-hexadecene, 1-heptadecene, 1-octadecene, 1-nonadecene, 1-eicosene, 2-butene, 2-methyl propene (isobutylene), 2-methylbutene, 2-pentene, 2-hexene, 3-hexane, 2-heptene, cyclohexene, propylene dimers, propylene trimers, propylene tetramers, piperylene, isoprene, 2-ethyl-1-hexene, 2-octene, styrene, 3-phenyl-1-propene, 1,4-hexadiene, 1,7-octadiene, 3-cyclohexyl-1-butene, allyl alcohol, allyl butyrate, hex-1-en-4-ol, oct-1-en-4-ol, vinyl acetate, allyl acetate, 3-butenyl acetate, vinyl propionate, allyl propionate, methyl methacrylate, vinyl ethyl ether, vinyl methyl ether, vinyl cyclohexene, allyl ethyl ether, methyl pentenoate, n-propyl-7-octenoate, pentenals, e.g., 2-pentenal, 3-pentenal and 4-pentenal; penten-1-ols, e.g., 2-penten-1-ol, 3-penten-1-ol and 4-penten-1-ol; 3-butenenitrile, 3-pentenenitrile, 5-hexenamide, 4-methyl styrene, 4-isopropyl styrene, 4-tert-butyl styrene, alpha-methyl styrene, 4-tert-butyl-alpha-methyl styrene, 1,3-diisopropenylbenzene, eugenol, iso-eugenol, safrole, iso-safrole, anethol, 4-allylanisole, indene, limonene, beta-pinene, dicyclopentadiene, cyclooctadiene, camphene, linalool, and the like. Other illustrative olefinic compounds may include, for example, p-isobutylstyrene, 2-vinyl-6-methoxynaphthylene, 3-ethenylphenyl phenyl ketone, 4-ethenylphenyl-2-thienylketone, 4-ethenyl-2-fluorobiphenyl, 4-(1,3-dihydro-1-oxo-2H-isoindol-2-yl) styrene, 2-ethenyl-5-benzoylthiophene, 3-ethenylphenyl phenyl ether, propenylbenzene, isobutyl-4-propenylbenzene, phenyl vinyl ether and the like. Other olefinic compounds include substituted aryl ethylenes as described in U.S. Pat. No. 4,329,507, the disclosure of which is incorporated herein by reference.

As indicated above, it is generally preferred to carry out the hydroformylation process of this invention in a continuous manner. In general, continuous hydroformylation processes are well known in the art and may involve: (a) hydroformylating the unsaturated alcohol or alkadiene starting material(s) with carbon monoxide and hydrogen in a liquid homogeneous reaction mixture comprising a solvent, the metal-ligand complex catalyst, and free ligand; (b) maintaining reaction temperature and pressure conditions favorable to the hydroformylation of the unsaturated alcohol or alkadiene starting material(s); (c) supplying make-up quantities of the unsaturated alcohol or alkadiene starting material(s), carbon monoxide and hydrogen to the reaction medium as those reactants are used up; and (d) recovering the desired aldehyde hydroformylation product(s) in any manner desired. The continuous process can be carried out in a single pass mode, i.e., wherein a vaporous mixture comprising unreacted unsaturated alcohol or alkadiene starting material(s) and vaporized aldehyde product is removed from the liquid reaction mixture from whence the aldehyde product is recovered and make-up unsaturated alcohol or alkadiene starting material(s), carbon monoxide and hydrogen are supplied to the liquid reaction medium for the next single pass through without recycling the unreacted unsaturated alcohol or alkadiene starting material(s). However, it is generally desirable to employ a continuous process that involves either a liquid and/or gas recycle procedure. Such types of recycle procedure are well known in the art and may involve the liquid recycling of the metal-ligand complex catalyst solution separated from the desired aldehyde reaction product(s), such as disclosed e.g., in U.S. Pat. No. 4,148,830 or a gas cycle procedure such as disclosed e.g., in U.S. Pat. No. 4,247,486, as well as a combination of both a liquid and gas recycle procedure if desired. The disclosures of said U.S. Pat. Nos. 4,148,830 and 4,247,486 are incorporated herein by reference thereto. The most preferred hydroformylation process of this invention comprises a continuous liquid catalyst recycle process.

Illustrative substituted and unsubstituted hydroxyaldehydes that can be prepared by the processes of this invention include, for example, 6-hydroxyhexanals such as 6-hydroxyhexanal and substituted 6-hydroxyhexanals (e.g., 2-methyl-6-hydroxyhexanal and 3,4-dimethyl-6-hydroxyhexanal) and the like, including mixtures of one or more of the above 6-hydroxyhexanals. Illustrative of suitable substituted and unsubstituted hydroxyaldehydes (including derivatives of hydroxyaldehydes) include those permissible substituted and unsubstituted hydroxyaldehydes which are described in Kirk-Othmer, Encyclopedia of Chemical Technology, Fourth Edition, 1996, the pertinent portions of which are incorporated herein by reference. As used herein, the term "hydroxyaldehydes" is contemplated to include, but is not limited to, 6-hydroxyhexanals and its cyclic lactols, hydrates or oligomers.

As indicated above, the hydroformylation reactions may involve a liquid catalyst recycle procedure. Such liquid catalyst recycle procedures are known as seen disclosed, e.g., in U.S. Pat. Nos. 4,668,651; 4,774,361; 5,102,505 and 5,110,990. For instance, in such liquid catalyst recycle procedures it is common place to continuously or intermittently remove a portion of the liquid reaction product medium, containing, e.g., the aldehyde product, the solubilized metal-ligand complex catalyst, free ligand, and organic solvent, as well as byproducts produced in situ by the hydroformylation, e.g., aldehyde condensation byproducts etc., and unreacted unsaturated alcohol or alkadiene starting material, carbon monoxide and hydrogen (syn gas) dissolved in said medium, from the hydroformylation reactor, to a distillation zone, e.g., a vaporizer/separator wherein the desired aldehyde product is distilled in one or more stages under normal, reduced or elevated pressure, as appropriate, and separated from the liquid medium. The vaporized or distilled desired aldehyde product so separated may then be condensed and recovered in any conventional manner as discussed above. The remaining non-volatilized liquid residue which contains metal-ligand complex catalyst, solvent, free ligand and usually some undistilled aldehyde product is then recycled back, with or without further treatment as desired, along with whatever by-product and non-volatilized gaseous reactants that might still also be dissolved in said recycled liquid residue, in any conventional manner desired, to the hydroformylation reactor, such as disclosed e.g., in the above-mentioned patents. Moreover the reactant gases so removed by such distillation from the vaporizer may also be recycled back to the reactor if desired.

In an embodiment of this invention, the hydroxyaldehyde mixtures may be separated from the other components of the crude reaction mixtures in which the aldehyde mixtures are produced by any suitable method. Suitable separation methods include, for example, solvent extraction, crystallization, distillation, vaporization, phase separation, wiped film evaporation, falling film evaporation and the like. It may be desired to remove the aldehyde products from the crude reaction mixture as they are formed through the use of trapping agents as described in published Patent Cooperation Treaty Patent Application WO 88/08835. A method for separating the aldehyde mixtures from the other components of the crude reaction mixtures is by membrane separation. Such membrane separation can be achieved as set out in U.S. Pat. No. 5,430,194 and copending U.S. patent application Ser. No. 08/430,790, filed May 5, 1995, both incorporated herein by reference.

As indicated above, at the conclusion of (or during) the process of this invention, the desired hydroxyaldehydes may be recovered from the reaction mixtures used in the process of this invention. For example, the recovery techniques disclosed in U.S. Pat. Nos. 4,148,830 and 4,247,486 can be used. For instance, in a continuous liquid catalyst recycle process the portion of the liquid reaction mixture (containing 6-hydroxyhexanal product, catalyst, etc.) removed from the reactor can be passed to a vaporizer/separator wherein the desired aldehyde product can be separated via distillation, in one or more stages, under normal, reduced or elevated pressure, from the liquid reaction solution, condensed and collected in a product receiver, and further purified if desired. The remaining non-volatilized catalyst containing liquid reaction mixture may then be recycled back to the reactor as may, if desired, any other volatile materials, e.g., unreacted olefin or alkadiene, together with any hydrogen and carbon monoxide dissolved in the liquid reaction after separation thereof from the condensed 6-hydroxyhexanal product, e.g., by distillation in any conventional manner. It is generally desirable to employ an organophosphorus ligand whose molecular weight exceeds that of the higher boiling aldehyde oligomer byproduct corresponding to the hydroxyhexanals being produced in the hydroformylation process. Another suitable recovery technique is solvent extraction or crystallization. In general, it is preferred to separate the desired hydroxyhexanals from the catalyst-containing reaction mixture under reduced pressure and at low temperatures so as to avoid possible degradation of the organophosphorus ligand and reaction products. When an alpha-mono-olefin reactant is also employed, the aldehyde derivative thereof can also be separated by the above methods.

More particularly, distillation and separation of the desired aldehyde product from the metal-ligand complex catalyst containing product solution may take place at any suitable temperature desired. In general, it is recommended that such distillation take place at relatively low temperatures, such as below 150° C., and more preferably at a temperature in the range of from about 50° C. to about 130° C. It is also generally recommended that such aldehyde distillation take place under reduced pressure, e.g., a total gas pressure that is substantially lower than the total gas pressure employed during hydroformylation when low boiling aldehydes (e.g., $C_5$ and $C_6$) are involved or under vacuum when high boiling aldehydes (e.g. $C_7$ or greater) are involved. For instance, a common practice is to subject the liquid reaction product medium removed from the hydroformylation reactor to a pressure reduction so as to volatilize a substantial portion of the unreacted gases dissolved in the liquid medium which now contains a much lower synthesis gas concentration than was present in the hydroformylation reaction medium to the distillation zone, e.g. vaporizer/separator, wherein the desired aldehyde product is distilled. In general, distillation pressures ranging from vacuum pressures on up to total gas pressure of about 50 psig should be sufficient for most purposes.

Particularly when conducting the process of this invention in a continuous liquid recycle mode employing an organophosphite ligand, undesirable acidic byproducts (e.g., a hydroxy alkyl phosphonic acid) may result due to reaction of the organophosphite ligand and the hydroxyaldehydes over the course of the process. The formation of such byproducts undesirably lowers the concentration of the ligand. Such acids are often insoluble in the reaction mixture and such insolubility can lead to precipitation of an undesirable gelatinous byproduct and may also promote the autocatalytic formation of further acidic byproducts. The organopolyphosphite ligands used in the process of this invention have good stability against the formation of such acids. However, if this problem does occur, the liquid reaction effluent stream of a continuous liquid recycle process may be passed, prior to (or more preferably after) separation of the desired hydroxyhexanal product therefrom, through any suitable weakly basic anion exchange resin, such as a bed of amine Amberlyst® resin, e.g., Amberlyst® A-21, and the like, to remove some or all of the undesirable acidic byproducts prior to its reincorporation into the hydroformylation reactor. If desired, more than one such basic anion exchange resin bed, e.g. a series of such beds, may be employed and any such bed may be easily removed and/or replaced as required or desired. Alternatively if desired, any part or all of the acid-contaminated catalyst recycle stream may be periodically removed from the continuous recycle operation and the contaminated liquid so removed treated in the same fashion as outlined above, to eliminate or reduce the amount of acidic by-product prior to reusing the catalyst containing liquid in the hydroformylation process. Likewise, any other suitable method for removing such acidic byproducts from the hydroformylation process of this invention may be employed herein if desired such as by extraction of the acid with a weak base (e.g., sodium bicarbonate).

The processes useful in this invention may involve improving the catalyst stability of any organic solubilized rhodium-organopolyphosphite complex catalyzed, liquid recycle hydroformylation process directed to producing aldehydes from olefinic unsaturated compounds which may experience deactivation of the catalyst due to recovery of the aldehyde product by vaporization separation from a reaction product solution containing the organic solubilized rhodium-organopolyphosphite complex catalyst and aldehyde product, the improvement comprising carrying out said vaporization separation in the presence of a heterocyclic nitrogen compound. See, for example, copending U.S. patent application Ser. No. 08/756,789, filed Nov. 26, 1996, the disclosure of which is incorporated herein by reference.

The processes useful in this invention may involve improving the hydrolytic stability of the organophosphite ligand and thus catalyst stability of any organic solubilized rhodium-organophosphite ligand complex catalyzed hydroformylation process directed to producing aldehydes from olefinic unsaturated compounds, the improvement comprising treating at least a portion of an organic solubilized rhodium-organophosphite ligand complex catalyst solution derived from said process and which also contains phosphorus acidic compounds formed during the hydroformylation process, with an aqueous buffer solution in order to neutralize and remove at least some amount of said phosphorus acidic compounds from said catalyst solution, and then returning the treated catalyst solution to the hydroformylation reactor. See, for example, copending U.S. patent application Ser. Nos. 08/756,501 and 08/753,505, both filed Nov. 26, 1996, the disclosures of which are incorporated herein by reference.

In an embodiment of this invention, deactivation of metal-organopolyphosphorus ligand complex catalysts caused by an inhibiting or poisoning organomonophosphorus compound can be reversed or at least minimized by carrying out hydroformylation processes in a reaction region where the hydroformylation reaction rate is of a negative or inverse order in carbon monoxide and optionally at one or more of the following conditions: at a temperature such that the temperature difference between reaction product fluid temperature and inlet coolant temperature is sufficient to prevent and/or lessen cycling of carbon monoxide partial pressure, hydrogen partial pressure, total reaction pressure, hydroformylation reaction rate and/or temperature during said hydroformylation process; at a carbon monoxide conversion sufficient to prevent and/or lessen cycling of carbon monoxide partial pressure, hydrogen partial pressure, total reaction pressure, hydroformylation reaction rate and/or temperature during said hydroformylation process; at a hydrogen conversion sufficient to prevent and/or lessen cycling of carbon monoxide partial pressure, hydrogen partial pressure, total reaction pressure, hydroformylation reaction rate and/or temperature during said hydroformylation process; and at an olefinic unsaturated compound conversion sufficient to prevent and/or lessen cycling of carbon monoxide partial pressure, hydrogen partial pressure, total reaction pressure, hydroformylation reaction rate and/or temperature during said hydroformylation process. See, for example, copending U.S. patent application Ser. No. 08/756, 499, filed Nov. 26, 1996, the disclosure of which is incorporated herein by reference.

As indicated above, the substituted and unsubstituted penten-1-ols and 6-hydroxyhexanals produced by the hydroformylation step of this invention can be separated by conventional techniques such as distillation, extraction, precipitation, crystallization, membrane separation, phase separation or other suitable means. For example, a crude reaction product can be subjected to a distillation-separation at atmospheric or reduced pressure through a packed distillation column. Reactive distillation may be useful in conducting the hydroformylation reaction step.

A one-step process involving the reductive hydroformylation of one or more substituted or unsubstituted alkadienes to produce one or more substituted or unsubstituted 6-hydroxyhexanals is disclosed in copending U.S. patent application Ser. No. (D-17488-1), filed on an even date herewith, the disclosure of which is incorporated herein by reference. Another process involving the production of one or more substituted or unsubstituted hydroxyhexanals by reductive hydroformylation/hydroformylation is disclosed in copending U.S. patent application Ser. No. (D-17477-1), filed on an even date herewith, the disclosure of which is incorporated herein by reference.

An embodiment of this invention relates to a process for producing one or more substituted or unsubstituted 6-hydroxyhexanals which comprises:

(a) subjecting one or more substituted or unsubstituted alkadienes, e.g., butadiene, to hydrocarbonylation in the presence of a hydrocarbonylation catalyst, e.g., a metal-organophosphorus ligand complex catalyst, and a promoter to produce one or more substituted or unsubstituted unsaturated alcohols comprising 3-penten-1-ols, 4-penten-1-ol and/or 2-penten-1-ols;

(b) optionally separating the 3-penten-1-ols, 4-penten-1-ol and/or 2-penten-1-ols from the hydrocarbonylation catalyst; and (c) subjecting said one or more substituted or unsubstituted unsaturated alcohols comprising 3-penten-1-ols, 4-penten-1-ol and/or 2-penten-1-ols to hydroformylation in the presence of a hydroformylation catalyst, e.g., a metal-organophosphorus ligand complex catalyst, to produce one or more substituted or unsubstituted 6-hydroxyhexanals. The reaction conditions in steps (a) and (c) may be the same or different, and the hydrocarbonylation catalyst in step (a) and the hydroformylation catalyst in step (c) may be the same or different.

Yet another embodiment of this invention relates to a process for producing one or more substituted or unsubstituted 6-hydroxyhexanals which comprises:

(a) subjecting one or more substituted or unsubstituted alkadienes, e.g., butadiene, to hydrocarbonylation in the presence of a hydrocarbonylation catalyst, e.g., a metal-organophosphorus ligand complex catalyst, and a promoter to produce one or more substituted or unsubstituted unsaturated alcohols comprising 3-penten-1-ols, 4-penten-1-ol and/or 2-penten-1-ols;

(b) optionally separating the 3-penten-1-ols, 4-penten-1-ol and/or 2-penten-1-ols from the hydrocarbonylation catalyst;

(c) optionally subjecting the 2-penten-1-ols and/or 3-penten-1-ols to isomerization in the presence of a heterogeneous or homogeneous olefin isomerization catalyst to partially or completely isomerize the 2-penten-1-ols and/or 3-penten-1-ols to 3-penten-1-ols and/or 4-penten-1-ol; and (d) subjecting said one or more substituted or unsubstituted unsaturated alcohols comprising 2-penten-1-ols, 3-penten-1-ols and/or 4-penten-1-ol to hydroformylation in the presence of a hydroformylation catalyst, e.g., a metal-organophosphorus ligand complex catalyst, to produce one or more substituted or unsubstituted 6-hydroxyhexanals. The reaction conditions in steps (a) and (d) may be the same or different, and the hydrocarbonylation catalyst in step (a) and the hydroformylation catalyst in step (d) may be the same or different.

The olefin isomerization catalyst in step (c) may be any of a variety of homogeneous or heterogeneous transition metal-based catalysts (particularly Ni, Rh, Pd, Pt, Co, Ru, or Ir), or may be a heterogeneous or homogeneous acid catalyst (particularly any acidic zeolite, polymeric resin, or source of $H^+$, any of which may be modified with one or more transition metals). Such olefin isomerization catalysts are known in the art and the isomerization can be conducted by conventional procedures known in the art. As used herein, the term "isomerization" is contemplated to include, but are not limited to, all permissible isomerization processes which involve converting one or more substituted or unsubstituted 2-penten-1-ols and/or 3-penten-1-ols to one or more substituted or unsubstituted 4-penten-1-ols.

When the processes of this invention are conducted in two stages (i.e., first producing 2-penten-1-ols, 3-penten-1-ols and/or 4-penten-1-ol under one set of conditions and then producing a 6-hydroxyhexanal from the 2-penten-1-ols, 3-penten-1-ols and/or 4-penten-1-ol under another set of conditions), it is preferred to conduct the first stage at a temperature from 75° C. to 110° C. and at a total pressure from 250 psi to 1000 psi and to conduct the second stage at a temperature from 60° C. to 120° C. and at a pressure from 5 psi to 500 psi. The same or different catalysts can be used in the first and second stages. The other conditions can be the same or different in both stages.

The processes of this invention can be operated over a wide range of reaction rates (m/L/h=moles of product/liter of reaction solution/hour). Typically, the reaction rates are at least 0.01 m/L/h or higher, preferably at least 0.1 m/L/h or higher, and more preferably at least 0.5 m/L/h or higher. Higher reaction rates are generally preferred from an economic standpoint, e.g., smaller reactor size, etc.

The substituted and unsubstituted hydroxyaldehyde products (e.g., 6-hydroxyhexanals) have a wide range of utilities that are well known in the art, e.g., they are useful as intermediates in the production of epsilon caprolactone, epsilon caprolactam, adipic acid and 1,6-hexanediol.

A one-step process involving the preparation of one or more substituted or unsubstituted 6-hydroxyhexanals from one or more substituted or unsubstituted alkadienes is disclosed in copending U.S. patent application Ser. No. (D-17477), filed Apr. 24, 1996, the disclosure of which is incorporated herein by reference.

The processes of this invention may be carried out using, for example, a fixed bed reactor, a fluid bed reactor, a continuous stirred tank reactor (CSTR) or a slurry reactor. The optimum size and shape of the catalysts will depend on the type of reactor used. In general, for fluid bed reactors, a small, spherical catalyst particle is preferred for easy fluidization. With fixed bed reactors, larger catalyst particles are preferred so the back pressure within the reactor is kept reasonably low.

The processes of this invention can be conducted in a batch or continuous fashion, with recycle of unconsumed starting materials if required. The reaction can be conducted in a single reaction zone or in a plurality of reaction zones, in series or in parallel or it may be conducted batchwise or continuously in an elongated tubular zone or series of such zones. The materials of construction employed should be inert to the starting materials during the reaction and the fabrication of the equipment should be able to withstand the reaction temperatures and pressures. Means to introduce and/or adjust the quantity of starting materials or ingredients introduced batchwise or continuously into the reaction zone during the course of the reaction can be conveniently utilized in the processes especially to maintain the desired molar ratio of the starting materials. The reaction steps may be effected by the incremental addition of one of the starting materials to the other. Also, the reaction steps can be combined by the joint addition of the starting materials. When complete conversion is not desired or not obtainable, the starting materials can be separated from the product, for example by distillation, and the starting materials then recycled back into the reaction zone.

The processes may be conducted in either glass lined, stainless steel or similar type reaction equipment. The reaction zone may be fitted with one or more internal and/or external heat exchanger(s) in order to control undue temperature fluctuations, or to prevent any possible "runaway" reaction temperatures.

The processes of this invention may be conducted in one or more steps or stages. The exact number of reaction steps or stages will be governed by the best compromise between achieving high catalyst selectivity, activity, lifetime and ease of operability, as well as the intrinsic reactivity of the starting materials in question and the stability of the starting materials and the desired reaction product to the reaction conditions.

In an embodiment, the processes useful in this invention may be carried out in a multistaged reactor such as described, for example, in copending U.S. patent application Ser. No.08/757,743, filed on Nov. 26, 1996, the disclosure of which is incorporated herein by reference. Such multistaged reactors can be designed with internal, physical barriers that create more than one theoretical reactive stage per vessel. In effect, it is like having a number of reactors inside a single continuous stirred tank reactor vessel. Multiple reactive stages within a single vessel is a cost effective way of using the reactor vessel volume. It significantly reduces the number of vessels that otherwise would be required to achieve the same results. Fewer vessels reduces the overall capital required and maintenance concerns with separate vessels and agitators.

The substituted and unsubstituted hydroxyaldehydes, e.g., 6-hydroxyhexanals, produced by the processes of this invention can undergo further reaction(s) to afford desired derivatives thereof. Such permissible derivatization reactions can be carried out in accordance with conventional procedures known in the art. Illustrative derivatization reactions include, for example, hydrogenation, esterification, etherification, amination, alkylation, dehydrogenation, reduction, acylation, condensation, carboxylation, carbonylation, oxidation, cyclization, silylation and the like, including permissible combinations thereof. Preferred derivatization reactions and derivatives of 6-hydroxyhexanal include, for example, reductive amination to give hexamethylenediamine, oxidation to give adipic acid, oxidation and cyclization to give epsilon caprolactone, oxidation, cyclization and amination to give epsilon caprolactam, and hydrogenation or reduction to give 1,6-hexanediols. This invention is not intended to be limited in any manner by the permissible derivatization reactions or permissible derivatives of substituted and unsubstituted 6-hydroxyhexanals.

For purposes of this invention, the term "hydrocarbon" is contemplated to include all permissible compounds having at least one hydrogen and one carbon atom. Such permissible compounds may also have one or more heteroatoms. In a broad aspect, the permissible hydrocarbons include acyclic (with or without heteroatoms) and cyclic, branched and unbranched, carbocyclic and heterocyclic, aromatic and nonaromatic organic compounds which can be substituted or unsubstituted.

As used herein, the term "substituted" is contemplated to include all permissible substituents of organic compounds unless otherwise indicated. In a broad aspect, the permissible substituents include acyclic and cyclic, branched and unbranched, carbocyclic and heterocyclic, aromatic and nonaromatic substituents of organic compounds. Illustrative substituents include, for example, alkyl, alkyloxy, aryl, aryloxy, hydroxy, hydroxyalkyl, amino, aminoalkyl, halogen and the like in which the number of carbons can range from 1 to about 20 or more, preferably from 1 to about 12. The permissible substituents can be one or more and the same or different for appropriate organic compounds. This invention is not intended to be limited in any manner by the permissible substituents of organic compounds.

For purposes of this invention, the chemical elements are identified in accordance with the Periodic Table of the Elements reproduced in "Basic Inorganic Chemistry" by F. Albert Cotton, Geoffrey Wilkinson and Paul L. Gaus, published by John Wiley and Sons, Inc., 3rd Edition, 1995.

Certain of the following examples are provided to further illustrate this invention.

EXAMPLES 1–19

Into a 100 milliliter overhead stirred high pressure reactor was charged 0.25 mmol of dicarbonylacetylacetonato rhodium (I), 0.9 mmol of a trialkylphosphine defined in Table A below, 3 milliliters of butadiene, 26 milliliters of a solvent as defined in Table A, and 1 milliliter of diglyme as internal standard. The reactor was pressurized with 5–10 psi of hydrogen/carbon monoxide in 1/1 ratio and heated to the desired temperature set out in Table A. At the desired temperature, the reactor was pressurized to the desired hydrogen/carbon monoxide ratio set out in Table A and the gas uptake was monitored. After a decrease in pressure of 10%, the reactor was re-pressurized to the initial value with hydrogen/carbon monoxide in 1/1 ratio. Samples of the reaction mixture were taken in dry ice cooled vials via the sampling line at scheduled intervals and analyzed by gas chromatography. At the end of the reaction period of 90 minutes, the gases were vented and the reaction mixture drained. Further details and results of analyses are set out in Table A.

TABLE A

| Ex. No. | Solvent/Promoter | Phosphine | Temp. (°C.) | $H_2$/CO (psi) | Butadiene Conv. (%) | Rate m/L/h | Selectivity (%) 3 & 4 Pentenols |
|---|---|---|---|---|---|---|---|
| 1 | Ethanol | Triethylphosphine | 60 | 300/300 | 27 | 0.2 | 92 |
| 2 | Ethanol | Triethylphosphine | 80 | 300/300 | 90 | 1.6 | 87 |
| 3 | Ethanol | Triethylphosphine | 80 | 500/500 | 87 | 1.3 | 91 |
| 4 | Ethanol | Triethylphosphine | 80 | 75/75 | 75 | 0.3 | 71 |
| 5 | Octanol | Trioctylphosphine | 80 | 600/200 | 98 | 1.9 | 88 |
| 6 | 3-Pentenol | Trioctylphosphine | 80 | 600/200 | 89 | nd | 90 |
| 7 | Hexanediol | Trioctylphosphine | 80 | 300/300 | 65 | nd | 93 |
| 8 | Pyrrole | Trioctylphosphine | 80 | 600/200 | 90 | 1.4 | 88 |
| 9 | Ethanol | Tributylphosphine | 80 | 300/300 | 55 | 1.0 | 70 |
| 10 | Phenol/THF | Trioctylphosphine | 80 | 600/200 | 84 | 2.0 | 55 |
| 11 | t-Butanol | Triethylphosphine | 120 | 250/250 | 99 | nd | 38 (15 min rxn. time) |
| 12 | Ethanol | Trimethylphosphine | 120 | 250/250 | 97 | nd | 42 (2 h rxn. time) |
| 13 | Ethanol | Diethyl-para-N,N-dimethylphenylphosphine | 80 | 600/200 | 70 | 1.2 | 64 |
| 14 | Ethanol/Acetonitrile | Triethylphosphine | 80 | 300/300 | 68 | 1.1 | 82 |
| 15 | Ethanol/Tetraglyme | Triethylphosphine | 80 | 300/300 | 64 | 1.0 | 91 |
| 16 | Diphenylamine | Trioctylphosphine | 80 | 600/200 | 80 | 0.8 | 54 |
| 17 | Acetamide | Trioctylphosphine | 80 | 600/200 | 85 | 0.9 | 34 |
| 18 | Methylacetamide | Trioctylphosphine | 80 | 600/200 | 73 | 0.8 | 59 |
| 19 | N-Methylformamide | Trioctylphosphine | 80 | 600/200 | 33 | 0.1 | 19 | nd = not determined

EXAMPLES 20–26

Into a 100 milliliter overhead stirred high pressure reactor was charged 0.25 mmol of dicarbonylacetylacetonato rhodium mmol of a trialkylphosphine defined in Table B below, 3 milliliters of butadiene, 26 milliliters of ethanol, and 1 milliliter of diglyme as internal standard. The reactor was pressurized with 5–10 psi of hydrogen/carbon monoxide in 1/1 ratio and heated to 80° C. At the desired temperature, the reactor was pressurized to the desired hydrogen/carbon monoxide ratio set out in Table B and the gas uptake was monitored. After a decrease in pressure of 10%, the reactor was re-pressurized to the initial value with hydrogen/carbon monoxide in 1/1 ratio. Samples of the reaction mixture were taken in dry ice cooled vials via the sampling line at scheduled intervals and analyzed by gas chromatography. At the end of the reaction period of 120 minutes, the gases were vented and the reaction mixture drained. Further details and results of analyses are set out in Table B.

TABLE B

| Ex. No. | Phosphine | H₂/CO (psi) | Butadiene Conv (%) | Rate (m/L/h) | Selectivity (%) 3 & 4 Pentenols |
|---|---|---|---|---|---|
| 20 | t-butyldiethyl phosphine | 300/300 | 60 | 0.8 | 13 |
| 21 | t-butyldiethyl phosphine | 800/200 | 69 | 1.1 | 19 |
| 22 | cyclohexyldiethyl phosphine | 300/300 | 76 | 0.7 | 75 |
| 23 | cyclohexyldiethyl phosphine | 800/200 | 82 | 1.4 | 80 |
| 24 | n-butyldiethyl phosphine | 300/300 | 77 | 1.1 | 82 |
| 25 | diethylphenyl phosphine | 200/800 | 53 | 0.9 | 77 |
| 26 | ethyldiphenyl phosphine | 200/806 | 38 | 0.6 | 27 |

EXAMPLE 27

A 160 milliliter magnetically stirred autoclave was purged with 1:1 H₂/CO and charged with a catalyst solution consisting of 0.1125 grams (0.44 mmol) dicarbonylacetylacetonato rhodium (I), 0.3515 grams (2.94 mmol) P(CH₂CH₂CH₂OH)₃, and 44.1 grams tetrahydrofuran. The autoclave was pressurized with 40 psig 1:1 H₂/CO and heated to 80° C. 6 milliliters (3.73 grams) of 1,3-butadiene was charged with a metering pump and the reactor was pressurized to 1000 psig with 1:1 H2/CO. The reaction mixture was maintained at 80° C. under 1000 psi 1:1 H₂/CO. Samples of the reaction mixture taken after 90 minutes and 170 minutes provided the following results:

| Time (minutes) | Temperature (°C.) | H₂/CO (psig) | Butadiene Conversion (%) | Rate (m/L/h) | Selectivity (%) 3 & 4 Pentenols |
|---|---|---|---|---|---|
| 90 | 80 | 500/500 | 81 | 0.7 | 66 |
| 170 | 80 | 500/500 | 96 | 0.4 | 72 |

EXAMPLE 28

A 160 milliliter magnetically stirred autoclave was purged with 1:1 H₂/CO and charged with a catalyst solution consisting of 0.1126 grams (0.44 minol) dicarbonylacetylacetonato rhodium (I), 0.6120 grams (1.69 mmol) P(CH₂CH₂CH₂OH)₃, and 39.9 grams of ethanol. The autoclave was pressurized with 40 psig 1:1 H₂/CO and heated to 80° C. 6 milliliters (3.73 grams) of 1,3-butadiene was charged with a metering pump and the reactor pressurized to 1000 psig with 1:1 H₂/CO. The reaction mixture was maintained at 80° C. under 1000 psi 1:1 H₂/CO. Samples of the reaction mixture taken after 15 and 43 minutes provided the following results:

| Time (minutes) | Temperature (°C.) | H₂/CO (psig) | Butadiene Conversion (%) | Rate (m/L/h) | Selectivity (%) 3 & 4 Pentenols |
|---|---|---|---|---|---|
| 15 | 80 | 500/500 | 53 | 2.6 | 70 |
| 43 | 80 | 500/500 | 89 | 1.5 | 78 |

EXAMPLE 29

A 100 milliliter overhead stirred high pressure reactor was charged with 0.12 mmol rhodium(I) dicarbonyl acetylacetonate, 2.2 mmol triphenylphosphine, 1.5 milliliters of cis-3-pentenol, 26 milliliters of ethyl alcohol, and 1 milliliter of diglyme as internal standard. The reactor was pressurized with 5 psi carbon monoxide and hydrogen in a 1:1 ratio, heated to 105° C., and then pressurized to 30 psi carbon monoxide and hydrogen. A sample of the reaction mixture was after 0.5 hours, and then analyzed by gas chromatography. Details of the reaction are set out in Table C below.

EXAMPLE 30

A 100 milliliter overhead stirred high pressure reactor was charged with 0.25 mmol rhodium(I) dicarbonyl acetylacetonate, 4.9 mmol triphenylphosphine, 1.5 milliliters of cis-3-pentenol, 26 milliliters of tetrahydrofuran, and 1 milliliter of diglyme as internal standard. The reactor was pressurized with 10 psi carbon monoxide and hydrogen in a 1:1 ratio, heated to 75° C., and then pressurized to 50 psi carbon monoxide and hydrogen. Samples of the reaction mixture were taken at time zero and after 5.5 hours, and then analyzed by gas chromatography. At the end of the reaction (5.5 hours), the gases were vented and the reaction mixture drained. Details of the reaction are set out in Table C.

EXAMPLE 31

A 100 milliliter overhead stirred high pressure reactor was charged with 0.22 mmol rhodium(I) dicarbonyl acetylacetonate, 4.4 mmol triphenylphosphine, 1.5 milliliters of cis-3-pentenol, 26 milliliters of ethyl alcohol, and 1 milliliter of diglyme as internal standard. The reactor was pressurized with 10 psi carbon monoxide and hydrogen in a 1:1 ratio, heated to 75° C., and then pressurized to 50 psi carbon monoxide and hydrogen. Samples of the reaction mixture were taken at time zero and after 20 hours, and then analyzed by gas chromatography. At the end of the reaction (20 hours), the gases were vented and the reaction mixture drained. Details of the reaction are set out in Table C.

EXAMPLE 32

A 100 milliliter overhead stirred high pressure reactor was charged with 0.25 mmol rhodium(I) dicarbonyl acetylacetonate, 4.9 mmol triphenylphosphine, 1.5 milliliters of cis-3-pentenol, 26 milliliters of tetrahydrofuran, and 1 milliliter of diglyme as internal standard. The reactor was pressurized with 5 psi carbon monoxide and hydrogen in a 1:1 ratio, heated to 100° C., and then pressurized to 30 psi carbon monoxide and hydrogen. Samples of the reaction mixture were taken at time zero and after 1.5 hours, and then analyzed by gas chromatography. At the end of the reaction (1.5 hours), the gases were vented and the reaction mixture drained. Details of the reaction are set out in Table C.

EXAMPLE 33

A 100 milliliter overhead stirred high pressure reactor was charged with 0.27 mmol rhodium(I) dicarbonyl acetylacetonate, 0.29 mmol (R)-(+)-2,2'-bis (diphenylphosphino)-1, 1'-binaphthyl, 1.5 milliliters of cis-3-pentenol, 26 milliliters of tetrahydrofuran, and 1 milliliter of diglyme as internal standard. The reactor was pressurized with 10 psi carbon monoxide and hydrogen in a 1:1 ratio, heated to 75° C., and then pressurized to 120 psi carbon monoxide and hydrogen. Samples of the reaction mixture were taken at time zero and after 2 hours, and then analyzed by gas chromatography. At the end of the reaction (2 hours), the gases were vented and the reaction mixture drained. Details of the reaction are set out in Table C.

TABLE C

| Ex. No. | Metal | Ligand | Solvent | Temp. (°C.) | $CO/H_2$ (psi) | Pent. Con. (%) | Rate (M/l-h) | $C5^a$ (%) | $C5^b$ (%) | Et5L (%) | Me6L (%) | 6-HH (%) |
|---|---|---|---|---|---|---|---|---|---|---|---|---|
| 29 | Rh | TPP | EtOH | 105 | 15/15 | 18 | n.d. | 14 | 37 | 7 | 15 | 25 |
| 30 | Rh | TPP | THF | 75 | 25/25 | 63 | 0.06 | 1 | 7 | 34 | 47 | 10 |
| 31 | Rh | TPP | EtOH | 75 | 25/25 | 40 | 0.01 | 2 | 12 | 36 | 34 | 14 |
| 32 | Rh | TPP | THF | 100 | 15/15 | 40 | 0.15 | 13 | 47 | 3 | 11 | 15 |
| 33 | Rh | BINAP | THF | 75 | 60/60 | 35 | 0.10 | 6 | 83 | 0 | 9 | 1 |

Pent. Conv. = cis-3-pentenol conversion; $C5^a$ = 1-pentanol + valeraldehyde + 2-pentenol; $C5^b$ = trans-3-pentenol + 4-pentenol; Et5L = 2-ethylbutyrolactol; Me6L = 2-methylvalerolactol; 6-HH = 6-hydroxyhexanal; TPP = triphenylphosphine; BINAP = (R)-(+)-2,2'-bis(diphenylphosphino)-1,1'-binaphthyl; EtOH = ethyl alcohol; THF = tetrahydrofuran.

EXAMPLE 34

A 100 milliliter overhead stirred high pressure reactor was charged with 0.10 mmol of dicarbonylacetylacetonato rhodium (I), about 0.20 mmol of 2,2'-(bisdiphenylphosphinomethyl)1,1'-biphenyl, 1 milliliter of 4-pentenol, 26 milliliters of ethanol, and 1 milliliter of diglyme as internal standard. The reactor was pressurized with 5–10 psi of 1/1 hydrogen/carbon monoxide, and heated to 90° C. At 90° C., the reactor was pressurized to 250 psi with 1/1 hydrogen/carbon monoxide at stirred for 1 hour. The reactor gases were vented and the reaction mixture drained and analyzed by gas chromatography. 6-Hydroxyhexanal was formed in 97% selectivity.

EXAMPLES 35–38

Into a 100 milliliter overhead stirred high pressure reactor was charged 0.07 mmol of dicarbonylacetylacetonato rhodium (I), 0.35 mmol of a bisphosphite ligand as identified in Table D below and depicted in the above specification, 25 milliliters of tetrahydrofuran, and 0.5 milliliter of diglyme as internal standard. The reactor was pressurized with 50 psi of hydrogen/carbon monoxide in 1/1 ratio and heated to the temperature in Table D. At the desired temperature, 1.0 milliliter of 3-pentenol was added and the reactor was pressurized to the desired hydrogen/carbon monoxide pressures set out in Table D. After a 5% drop in the reactor pressure, the reactor was re-pressurized to the initial value with hydrogen/carbon monoxide in 1/1 ratio. At the end of the reaction period of 120 minutes, the gases were vented and the reaction mixture drained and analyzed by gas chromatography. Further details and results of analyses are set out in Table D.

TABLE D

| Ex. No. | Bisphosphite ligand | Temp. (°C.) | $H_2/CO$ (psi) | 3-Pentenol Conv. (%) | Selectivity to 6-hydroxyhexanal (%) |
|---|---|---|---|---|---|
| 35 | Ligand F | 85 | 100/100 | 68 | 60 |
| 36 | Ligand F | 95 | 200/50 | 94 | 59 |
| 37 | Ligand D | 85 | 100/100 | 44 | 65 |
| 38 | Ligand D | 95 | 333/167 | 52 | 58 |

EXAMPLES 39–43

Into a 100 milliliter overhead stirred high pressure reactor was charged 0.07 mmol of dicarbonylacetylacetonato rhodium 0.35 mmol of a bisphosphite ligand as identified in Table E below and depicted below or in the above specification, 25 milliliters of tetrahydrofuran, and 0.5 milliliter of digylme as internal standard. The reactor was pressurized with 50 psi of hydrogen/carbon monoxide in 1/1 ratio and heated to 95° C. At the desired temperature, 1.0 milliliter of 3-pentenol was added and the reactor was pressurized to 500 psi with hydrogen/carbon monoxide in 1/1 ratio. After a 5% drop in the reactor pressure, the reactor was re-pressurized to the initial value with hydrogen/carbon monoxide in 1/1 ratio. At the end of the reaction period of 120 minutes, the gases were vented and the reaction mixture drained and analyzed by gas chromatography. Further details and results of analyses are set out in the Table E.

TABLE E

| Ex. No. | Bisphosphite ligand | 3-Pentenol Conv. (%) | Selectivity to 6-hydroxyhexanal (%) |
|---|---|---|---|
| 39 | Ligand W | 20 | 59 |
| 40 | Ligand X | 50 | 59 |
| 41 | Ligand E | 67 | 55 |
| 42 | Ligand Y | 92 | 44 |
| 43 | ethylidene bis(di-t-butyl) phenyl (phenylene glycol-P)2 | 54 | 29 |

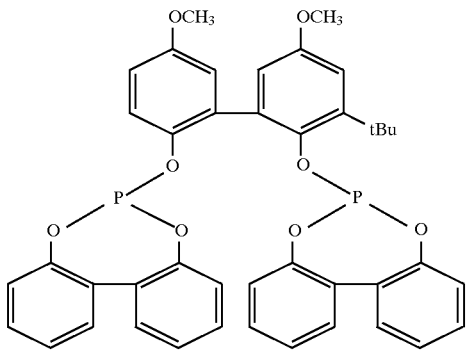

Ligand W

TABLE E-continued

| Ex. No. | Bisphosphite ligand | 3-Pentenol Conv. (%) | Selectivity to 6-hydroxyhexanal (%) |
|---|---|---|---|

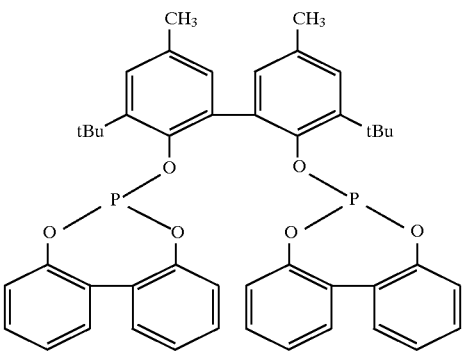

Ligand X

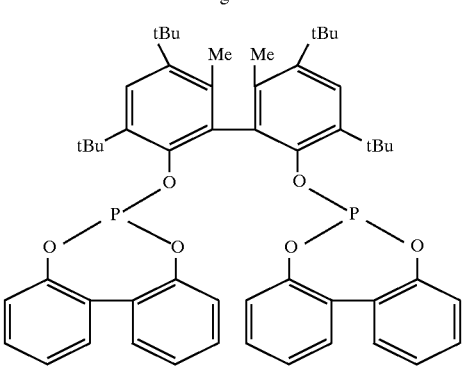

Ligand Y

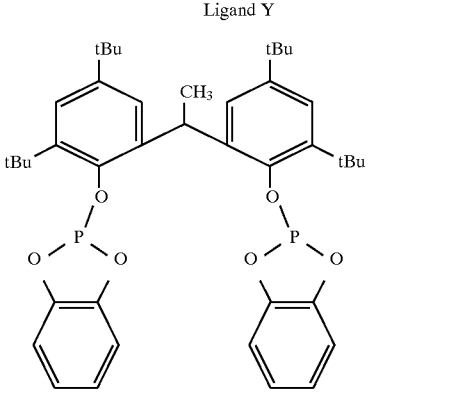

ethylene bis(di-t-butyl)
phenol(phenylene glycol-P)$_2$

Example 44–47

A 100 milliliter magnetically stirred autoclave was urged with N$_2$ for 30 minutes and charged with a solution consisting of 3 milliliters of 3-pentenol, 26 milliliters of tetrahydrofuran, Ligand Z identified below and dicarbonylacetylacetonato Rh (I) in amounts listed in Table F below. The autoclave was pressurized with 60–80% of the total amount of 1:1 hydrogen/carbon monoxide and heated to the temperature listed in Table F. The total amount of 1:1 hydrogen/carbon monoxide was as follows: Ex. 44–100 psi hydrogen and 100 psi carbon monoxide; Ex. 45–100 psi hydrogen and 100 psi carbon monoxide; Ex. 46–50 psi hydrogen and 50 psi carbon monoxide; and Ex. 47–100 psi hydrogen and 100 psi carbon monoxide. After the appropriate temperature was reached, the autoclave was pressurized to the total amount of 1:1 hydrogen/carbon monoxide described above. The reaction mixture was maintained isothermally under 1:1 hydrogen/carbon monoxide. Samples of the reaction mixture taken after 150 minutes gave the results listed in Table F. Selectivities were determined by gas chromatography and referenced to standard response factors. 0.94 grams (7.02 mmol) of diglyme was used as an internal gas chromatography standard in the reaction mixture.

TABLE F

| Ex. No. | Temp (°C.) | Ligand Z (g) | Rh(CO)$_2$ (acac) (g) | 3-pentenol Conversion | Rate (m/L/h) | 6-Hydroxyhexanal Selectivity (%) |
|---|---|---|---|---|---|---|
| 44 | 85 | 0.355 | 0.02 | 13% | 0.5 | 46.7 |
| 45 | 90 | 1.07 | 0.07 | 74% | 0.70 | 54.3 |
| 46 | 105 | 0.14 | 0.02 | 96% | 0.96 | 61.2 |
| 47 | 95 | 0.35 | 0.02 | 38% | 0.41 | 54.4 |

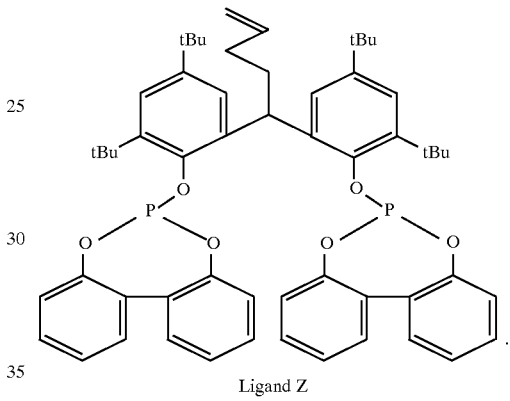

Ligand Z

EXAMPLE 48

Tetrarhodium dodecacarbonyl (52.3 milligrams) and Ligand F (1.17 grams) was dissolved in tetraglyme (80 milliliters). To this was added nonane (1.07 grams) as gas chromatograph internal standard, and cis-3-pentenol (25.8 grams). The mixture was charged to a 300 milliliter stirred Parr autoclave and 200 psig of synthesis gas was added (1:1 carbon monoxide:hydrogen). The reactor temperature was raised to 95° C., synthesis gas was added to the reactor to bring the pressure to 500 psig. The reaction was run for 157 minutes, before being stopped. Gas chromatograph analysis of the reaction mixture showed the following composition: valeraldehyde (23.7%), trans-3-pentenol (8.7%), cis-3-pentenol (13.6%), branched hydroxyaldehyde (5.6%), and 6-hydroxyhexanal (52.2%). The identity of the linear and branched aldehydes was confirmed by gas chromatograph mass spectrometry/infrared spectroscopy.

Although the invention has been illustrated by certain of the preceding examples, it is not to be construed as being limited thereby; but rather, the invention encompasses the generic area as hereinbefore disclosed. Various modifications and embodiments can be made without departing from the spirit and scope thereof.

We claim:

1. A process for producing one or more substituted or unsubstituted hydroxyaldehydes which comprises subjecting one or more substituted or unsubstituted alkadienes to hydrocarbonylation in the presence of a hydrocarbonylation catalyst and a promoter and hydroformylation in the presence of a hydroformylation catalyst to produce said one or more substituted or unsubstituted hydroxyaldehydes.

2. A process for producing one or more substituted or unsubstituted hydroxyaldehydes which comprises subjecting one or more substituted or unsubstituted pentenals to a hydrocarbonylation in the presence of a hydrocarbonylation catalyst and a promoter to produce said one or more substituted or unsubstituted hydroxyaldehydes.

3. A process for producing one or more substituted or unsubstituted hydroxyaldehydes which comprises: (a) subjecting one or more substituted or unsubstituted alkadienes to hydrocarbonylation in the presence of a hydrocarbonylation catalyst and a promoter to produce one or more substituted or unsubstituted unsaturated alcohols, and (b) subjecting said one or more substituted or unsubstituted unsaturated alcohols to hydroformylation in the presence of a hydroformylation catalyst to produce said one or more substituted or unsubstituted hydroxyaldehydes.

4. The process of claim 3 wherein the substituted or unsubstituted alkadiene comprises butadiene, the substituted or unsubstituted alcohols comprise cis-3-penten-1-ol, trans-3-penten-1-ol, 4-penten-1-ol, cis-2-penten-1-ol and/or trans-2-penten-1-ol and the substituted or unsubstituted hydroxyaldehydes comprise 6-hydroxyhexanal.

5. The process of claim 3 wherein the hydrocarbonylation reaction conditions in step (a) and the hydroformylation reaction conditions in step (b) may be the same or different, and the hydrocarbonylation catalyst in step (a) and the hydroformylation catalyst in step (b) may be the same or different.

6. The process of claim 3 wherein said hydrocarbonylation catalyst comprises a metal selected from a Group 8, 9 and 10 metal complexed with an organophosphine ligand selected from a mono-, di-, tri- and poly-(organophosphine) ligand.

7. The process of claim 3 wherein said hydrocarbonylation catalyst comprises a metal selected from a Group 8, 9 and 10 metal complexed with an organophosphine ligand selected from a triorganophosphine ligand represented by the formula:

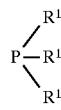

wherein each $R^1$ is the same or different and is a substituted or unsubstituted monovalent hydrocarbon radical.

8. The process of claim 7 wherein each $R^1$ is the same or different and is selected from primary alkyl, secondary alkyl, tertiary alkyl and aryl.

9. The process of claim 7 wherein the ligand in step (a) has a basicity greater than or equal to the basicity of triphenylphosphine (pKb=2.74) and a steric bulk lower than or equal to a Tolman cone angle of 210°.

10. The process of claim 6 wherein the promoter is incorporated into the ligand structure either as the metal-ligand complex catalyst or as free ligand.

11. The process of claim 1 wherein the promoter has a pKa of about 1–35 and comprises a protic solvent, organic and inorganic acid, alcohol, water, phenol, thiol, selenol, nitroalkane, ketone, nitrile, amine, amide, or a mono-, di- or trialkylammonium salt or mixtures thereof.

12. The process of claim 1 wherein the hydroformylation catalyst comprises a metal-organophosphorus ligand complex catalyst.

13. The process of claim 12 wherein said metal-organophosphorus ligand complex catalyst comprises a metal selected from a Group 8, 9 and 10 metal complexed with an organophosphorus ligand selected from a mono-, di-, tri- and poly-(organophosphine) ligand.

14. The process of claim 12 wherein said metal-organophosphorus ligand complex catalyst comprises a metal selected from a Group 8, 9 and 10 metal complexed with an organophosphorus ligand selected from:

(i) a triorganophosphine ligand represented by the formula:

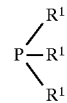

wherein each $R^1$ is the same or different and is a substituted or unsubstituted monovalent hydrocarbon radical;

(ii) a monoorganophosphite represented by the formula:

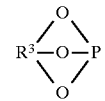

wherein $R^3$ represents a substituted or unsubstituted trivalent hydrocarbon radical containing from 4 to 40 carbon atoms or greater;

(iii) a diorganophosphite represented by the formula:

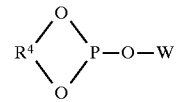

wherein $R^4$ represents a substituted or unsubstituted divalent hydrocarbon radical containing from 4 to 40 carbon atoms or greater and W represents a substituted or unsubstituted monovalent hydrocarbon radical containing from 1 to 18 carbon atoms or greater;

(iv) a triorganophosphite represented by the formula:

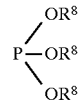

wherein each $R^8$ is the same or different and is a substituted or unsubstituted monovalent hydrocarbon radical; and (v) an organopolyphosphite containing two or more tertiary (trivalent) phosphorus atoms represented by the formula:

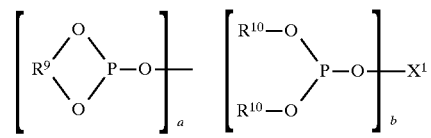

wherein $X^1$ represents a substituted or unsubstituted n-valent hydrocarbon bridging radical containing from 2 to 40 carbon atoms, each $R^9$ is the same or different and is a divalent hydrocarbon radical containing from 4 to 40 carbon atoms, each $R^{10}$ is the same or different and is a substituted or unsubstituted monovalent hydrocarbon radical containing from 1 to 24 carbon atoms, a and b can be the same or different and each have a value of 0 to 6, with the proviso that the sum of a+b is 2 to 6 and n equals a+b.

15. The process of claim 12 wherein said metal-organophosphorus ligand complex catalyst comprises a metal selected from a Group 8, 9 and 10 metal complexed with an organophosphorus ligand having the formula:

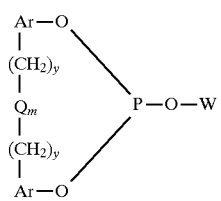

wherein W represents a substituted or unsubstituted monovalent hydrocarbon radical containing from 1 to 18 carbon atoms or greater, each Ar is the same or different and represents a substituted or unsubstituted aryl radical, each y is the same or different and is a value of 0 or 1, Q represents a divalent bridging group selected from $-C(R^5)_2-$, $-O-$, $-S-$, $-NR^{6-}$, $Si(R^7)_2-$ and $-CO-$, wherein each $R^5$ is the same or different and represents hydrogen, alkyl radicals having from 1 to 12 carbon atoms, phenyl, tolyl, and anisyl, $R^6$ represents hydrogen or a methyl radical, each $R^7$ is the same or different and represents hydrogen or a methyl radical, and m is a value of 0 or 1.

16. The process of claim 12 wherein said metal-organophosphorus ligand complex catalyst comprises a metal selected from a Group 8, 9 and 10 metal complexed with an organophosphorus ligand having the formula selected from:

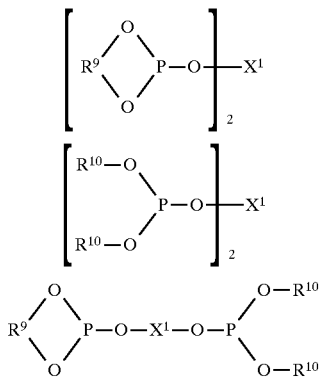

wherein $X^1$ represents a substituted or unsubstituted n-valent hydrocarbon bridging radical containing from 2 to 40 carbon atoms, each $R^9$ is the same or different and is a divalent hydrocarbon radical containing from 4 to 40 carbon atoms, and each $R^{10}$ is the same or different and is a substituted or unsubstituted monovalent hydrocarbon radical containing from 1 to 24 carbon atoms.

17. The process of claim 12 wherein said metal-organophosphorus ligand complex catalyst comprises a metal selected from a Group 8, 9 and 10 metal complexed with an organophosphorus ligand having the formula selected from:

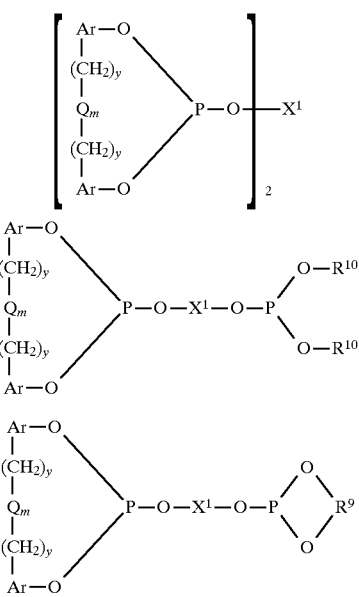

wherein $X^1$ represents a substituted or unsubstituted n-valent hydrocarbon bridging radical containing from 2 to 40 carbon atoms, each $R^9$ is the same or different and is a divalent hydrocarbon radical containing from 4 to 40 carbon atoms, each $R^{10}$ is the same or different and is a substituted or unsubstituted monovalent hydrocarbon radical containing from 1 to 24 carbon atoms, each Ar is the same or different and represents a substituted or unsubstituted aryl radical, each y is the same or different and is a value of 0 or 1, Q represents a divalent bridging group selected from $-C(R^5)_2-$, $-O-$, $-S-$, $-NR^{6-}$, $Si(R^7)_2-$ and $-CO-$, wherein each $R^5$ is the same or different and represents hydrogen, alkyl radicals having from 1 to 12 carbon atoms, phenyl, tolyl, and anisyl, $R^6$ represents hydrogen or a methyl radical, each $R^7$ is the same or different and represents hydrogen or a methyl radical, and m is a value of 0 or 1.

18. The process of claim 1 which is conducted at a temperature from about 50° C. to 150° C. and at a total pressure from about 20 psig to about 3000 psig.

19. A process for producing a batchwise or continuously generated reaction mixture comprising:

(1) one or more substituted or unsubstituted 6-hydroxyhexanals;

(2) optionally one or more substituted or unsubstituted penten-1-ols;

(3) optionally one or more substituted or unsubstituted 5-hydroxypentanals and/or cyclic lactol derivatives thereof;

(4) optionally one or more substituted or unsubstituted 4-hydroxybutanals and/or cyclic lactol derivatives thereof;

(5) optionally one or more substituted or unsubstituted pentan-1-ols;

(6) optionally one or more substituted or unsubstituted valeraldehydes;

(7) optionally one or more substituted or unsubstituted pentenals;

(8) optionally one or more substituted or unsubstituted 1,6-hexanedials;

(9) optionally one or more substituted 1,5-pentanedials;

(10) optionally one or more substituted 1,4-butanedials; and

(11) one or more substituted or unsubstituted butadienes; wherein the weight ratio of component (1) to the sum of components (2), (3), (4), (5), (6), (7), (8), (9) and (10) is greater than about 0.1; and the weight ratio of component (11) to the sum of components (1), (2), (3), (4), (5), (6), (7), (8), (9) and (10) is about 0 to about 100; which process comprises reacting one or more substituted or unsubstituted butadienes with carbon monoxide and hydrogen in the presence of a metal-ligand complex catalyst and a promoter and optionally free ligand to produce one or more substituted or unsubstituted penten-1-ols, and reacting said one or more substituted or unsubstituted penten-1-ols with carbon monoxide and hydrogen in the presence of a metal-ligand complex catalyst and optionally free ligand to produce said batchwise or continuously generated reaction mixture.

20. A process for producing a reaction mixture comprising one or more substituted or unsubstituted hydroxyaldehydes which process comprises reacting one or more substituted or unsubstituted alkadienes with carbon monoxide and hydrogen in the presence of a metal-ligand complex catalyst and a promoter and optionally free ligand to produce one or more substituted or unsubstituted unsaturated alcohols, and reacting said one or more substituted or unsubstituted unsaturated alcohols with carbon monoxide and hydrogen in the presence of a metal-ligand complex catalyst and optionally free ligand to produce said reaction mixture comprising one or more substituted or unsubstituted hydroxyaldehydes.

21. A process for producing one or more substituted or unsubstituted 6-hydroxyhexanals which comprises:
    (a) subjecting one or more substituted or unsubstituted alkadienes to hydrocarbonylation in the presence of a hydrocarbonylation catalyst and a promoter to produce one or more substituted or unsubstituted unsaturated alcohols comprising 3-penten-1-ols, 4-penten-1-ol and/or 2-penten-1-ols;
    (b) optionally separating the 3-penten-1-ols, 4-penten-1-ol and/or 2-penten-1-ols from the hydrocarbonylation catalyst; and
    (c) subjecting said one or more substituted or unsubstituted unsaturated alcohols comprising 3-penten-1-ols, 4-penten-1-ol and/or 2-penten-1-ols to hydroformylation in the presence of a hydroformylation catalyst to produce one or more substituted or unsubstituted 6-hydroxyhexanals.

22. A process for producing one or more substituted or unsubstituted 6-hydroxyhexanals which comprises:
    (a) subjecting one or more substituted or unsubstituted alkadienes to hydrocarbonylation in the presence of a hydrocarbonylation catalyst to produce one or more substituted or unsubstituted unsaturated alcohols comprising 3-penten-1-ols, 4-penten-1-ol and/or 2-penten-1-ols;
    (b) optionally separating the 3-penten-1-ols, 4-penten-1-ol and/or 2-penten-1-ols from the hydrocarbonylation catalyst;
    (c) optionally subjecting the 2-penten-1-ols and/or 3-penten-1-ols to isomerization in the presence of a heterogeneous or homogeneous olefin isomerization catalyst to partially or completely isomerize the 2-penten-1-ols and/or 3-penten-1-ols to 3-penten-1-ols and/or 4-penten-1-ol; and
    (d) subjecting said one or more substituted or unsubstituted unsaturated alcohols comprising 2-penten-1-ols, 3-penten-1-ols and/or 4-penten-1-ol to hydroformylation in the presence of a hydroformylation catalyst to produce one or more substituted or unsubstituted 6-hydroxyhexanals.

23. A batchwise or continuously generated reaction mixture comprising:
    (1) one or more substituted or unsubstituted 6-hydroxyhexanals;
    (2) optionally one or more substituted or unsubstituted penten-1-ols;
    (3) optionally one or more substituted or unsubstituted 5-hydroxypentanals and/or cyclic lactol derivatives thereof;
    (4) optionally one or more substituted or unsubstituted 4-hydroxybutanals and/or cyclic lactol derivatives thereof;
    (5) optionally one or more substituted or unsubstituted pentan-1-ols;
    (6) optionally one or more substituted or unsubstituted valeraldehydes;
    (7) optionally one or more substituted or unsubstituted pentenals;
    (8) optionally one or more substituted or unsubstituted 1,6-hexanedials;
    (9) optionally one or more substituted 1,5-pentanedials;
    (10) optionally one or more substituted 1,4-butanedials; and
    (11) one or more substituted or unsubstituted butadienes; wherein the weight ratio of component (1) to the sum of components (2), (3), (4), (5), (6), (7), (8), (9) and (10) is greater than about 0.1; and the weight ratio of component (11) to the sum of components (1), (2), (3), (4), (5), (6), (7), (8), (9) and (10) is about 0 to about 100.

24. A batchwise or continuously generated reaction mixture comprising:
    (1) one or more substituted or unsubstituted 6-hydroxyhexanals;
    (2) optionally one or more substituted or unsubstituted penten-1-ols;
    (3) optionally one or more substituted or unsubstituted 5-hydroxypentanals and/or cyclic lactol derivatives thereof;
    (4) optionally one or more substituted or unsubstituted 4-hydroxybutanals and/or cyclic lactol derivatives thereof, (5) optionally one or more substituted or unsubstituted pentan-1-ols;
    (6) optionally one or more substituted or unsubstituted valeraldehydes; and
    (7) one or more substituted or unsubstituted pentenals; wherein the weight ratio of component (1) to the sum of components (2), (3), (4), (5) and (6) is greater than about 0.1; and the weight ratio of component (7) to the sum of components (1), (2), (3), (4), (5) and (6) is about 0 to about 100.

25. A reaction mixture comprising one or more substituted or unsubstituted hydroxyaldehydes in which said reaction mixture is prepared by a process which comprises reacting one or more substituted or unsubstituted alkadienes with carbon monoxide and hydrogen in the presence of a metal-ligand complex catalyst and a promoter and optionally free ligand to produce one or more substituted or unsubstituted unsaturated alcohols, and reacting said one or more substituted or unsubstituted unsaturated alcohols with carbon monoxide and hydrogen in the presence of a metal-ligand complex catalyst and optionally free ligand to produce said reaction mixture comprising one or more substituted or unsubstituted hydroxyaldehydes.

26. The reaction mixture of claim 25 in which the process further comprises derivatizing the one or more substituted or unsubstituted 6-hydroxyhexanals.

27. The reaction mixture of claim 26 in which the derivatizing reaction comprises hydrogenation, esterification, etherification, amination, alkylation, dehydrogenation, reduction, acylation, condensation, carboxylation, carbonylation, oxidation, cyclization, silylation and permissible combinations thereof.

* * * * *